(12) United States Patent
Cha et al.

(10) Patent No.: US 11,279,693 B2
(45) Date of Patent: Mar. 22, 2022

(54) ORGANIC HETEROCYCLIC COMPOUND AND LIGHT-EMITTING DIODE COMPRISING SAME

(71) Applicant: SFC CO., LTD., Cheongju-si (KR)

(72) Inventors: Soon-Wook Cha, Goyang-si (KR); Jung-Ho Yoo, Seosan-si (KR); Ji-Hwan Kim, Anyang-si (KR); Sang-Woo Park, Seoul (KR); Yoona Shin, Seoul (KR); Jea-Geon Lim, Cheongju-si (KR)

(73) Assignee: SFC CO., LTD., Cheongju-si (KR)

( * ) Notice: Subject to any disclaimer, the term of this patent is extended or adjusted under 35 U.S.C. 154(b) by 416 days.

(21) Appl. No.: 15/772,122

(22) PCT Filed: Nov. 1, 2016

(86) PCT No.: PCT/KR2016/012476
§ 371 (c)(1),
(2) Date: Apr. 30, 2018

(87) PCT Pub. No.: WO2017/082574
PCT Pub. Date: May 18, 2017

(65) Prior Publication Data
US 2018/0319776 A1    Nov. 8, 2018

(30) Foreign Application Priority Data
Nov. 13, 2015   (KR) .................. 10-2015-0159666

(51) Int. Cl.
*C07D 405/04*   (2006.01)
*C07D 405/10*   (2006.01)
(Continued)

(52) U.S. Cl.
CPC ......... *C07D 405/04* (2013.01); *C07D 307/77* (2013.01); *C07D 405/10* (2013.01);
(Continued)

(58) Field of Classification Search
CPC ... C07B 59/002; C07D 311/82; C07D 335/12; C07D 409/04; C07D 471/14; C07D 487/04; C07D 491/052; C07D 491/20; C07D 493/10; C07D 495/04; C07D 495/10; C07D 498/04; C07D 498/14; C07D 513/04; C07D 513/14; C07D 519/00; C07F 7/0816; C09K 11/025; H01L 51/0067;
(Continued)

(56) References Cited

U.S. PATENT DOCUMENTS

2016/0308147 A1* 10/2016 Parham ............... C07D 409/04

FOREIGN PATENT DOCUMENTS

| CN | 105051035 A | 11/2015 |
|---|---|---|
| JP | 2010168363 A | 8/2010 |

(Continued)

OTHER PUBLICATIONS

International Search Report of PCT/KR2016/012476, dated Feb. 13, 2017, English Translation.

*Primary Examiner* — Tae-Sik Kang
(74) *Attorney, Agent, or Firm* — STIR Law Group, LLC

(57) ABSTRACT

The present disclosure relates to an organic compound represented by Chemical Formula A or B, and an organic light-emitting diode comprising the same.

14 Claims, 1 Drawing Sheet

(51) Int. Cl.
*C09K 11/06* (2006.01)
*C07D 307/77* (2006.01)
*C07D 405/14* (2006.01)
*C07D 495/12* (2006.01)
*C07D 517/20* (2006.01)
*C07D 493/20* (2006.01)
*C07D 409/14* (2006.01)
*C07D 409/04* (2006.01)
*C07D 409/10* (2006.01)
*C07D 491/048* (2006.01)
*C07D 491/153* (2006.01)
*C07D 493/04* (2006.01)
*C07D 493/14* (2006.01)
*H01L 51/00* (2006.01)
*H01L 51/50* (2006.01)
*H01L 51/52* (2006.01)

(52) U.S. Cl.
CPC ......... *C07D 405/14* (2013.01); *C07D 409/04* (2013.01); *C07D 409/10* (2013.01); *C07D 409/14* (2013.01); *C07D 491/048* (2013.01); *C07D 491/153* (2013.01); *C07D 493/04* (2013.01); *C07D 493/14* (2013.01); *C07D 493/20* (2013.01); *C07D 495/12* (2013.01); *C07D 517/20* (2013.01); *C09K 11/06* (2013.01); *H01L 51/0067* (2013.01); *H01L 51/0073* (2013.01); *H01L 51/0074* (2013.01); *H01L 51/5024* (2013.01); *H01L 51/5056* (2013.01); *H01L 51/5092* (2013.01); *H01L 51/5072* (2013.01); *H01L 51/5206* (2013.01); *H01L 51/5221* (2013.01)

(58) Field of Classification Search
CPC .............. H01L 51/0068; H01L 51/0073; H01L 51/0074
See application file for complete search history.

(56) References Cited

FOREIGN PATENT DOCUMENTS

| KR | 100691543 | B1 | 3/2007 |
|----|-----------|----|--------|
| KR | 1020120104204 | A | 9/2012 |
| KR | 101429035 | B1 | 8/2014 |
| KR | 1020140145456 | A | 12/2014 |
| KR | 20150034390 | A | 4/2015 |
| KR | 20150045809 | A | 4/2015 |
| KR | 1020150034390 | A | 4/2015 |
| KR | 1020150045809 | A | 4/2015 |
| KR | 20150113642 | A | 10/2015 |

* cited by examiner

| 80 |
|----|
| 70 |
| 60 |
| 50 |
| 40 |
| 30 |
| 20 |
| 10 |

ORGANIC HETEROCYCLIC COMPOUND AND LIGHT-EMITTING DIODE COMPRISING SAME

CROSS-REFERENCE TO RELATED APPLICATIONS

This application is the U.S. National Phase under 35 U.S.C. § 371 of International Application No. PCT/KR2016/012476 filed on Nov. 1, 2016, which in turn claims the benefit of Korean Application No. 10-2015-0159666, filed on Nov. 13, 2015, the disclosures of which are incorporated by reference into the present application.

TECHNICAL FIELD

The present invention relates to a novel heterocyclic compound and an organic light-emitting diode comprising the same and, more particularly, to a heterocyclic compound which can lower a driving voltage and exhibit the diode characteristic of excellent luminance efficiency and an organic light-emitting diode comprising the same.

BACKGROUND ART

Organic light-emitting diodes (OLEDs), based on self-luminescence, enjoy the advantage of having a wide viewing angle and being able to be made thinner and lighter than liquid crystal displays. In addition, an OLED display exhibits a very fast response time. Accordingly, OLEDs find applications in the full color display field or the illumination field.

In general, the term "organic light-emitting phenomenon" refers to a phenomenon in which electrical energy is converted to light energy by means of an organic material.

An OLED using the organic light phenomenon has a structure usually comprising an anode, a cathode, and an organic material layer interposed therebetween. In this regard, the organic material layer may be, for the most part, of a multilayer structure consisting of different materials, for example, a hole injection layer, a hole transport layer, a light-emitting layer, an electron transport layer, and an electron injection layer, in order to improve the efficiency and stability of the organic light-emitting diode. In the organic light-emitting diode having such a structure, when a voltage is applied between the two electrodes, a hole injected from the anode migrates to the organic layer while an electron is released from the cathode and moves toward the organic layer. In the luminescence zone, the hole and the electron recombine to produce an exciton. When the exciton returns to the ground state from the excited state, the molecule of the organic layer emits light. Such an organic light-emitting diode is known to have characteristics such as self-luminescence, high luminescence, high efficiency, a low driving voltage, a wide viewing angle, high contrast, and high-speed response.

Materials used as the organic layers in OLEDs may be divided into luminescent materials and charge transport materials, for example, a hole injection material, a hole transport material, an electron injection material, and an electron transport material. As for the luminescent materials, there are two main families of OLED: those based on small molecules and those employing polymers. The light-emitting mechanism forms the basis for classification of the luminescent materials as fluorescent or phosphorescent materials, which use excitons in singlet and triplet states, respectively.

Meanwhile, when a single material is employed as the luminescent material, intermolecular actions cause the wavelength of maximum luminescence to shift toward a longer wavelength, decreasing color purity or attenuating light with the consequent reduction in efficiency of the diode. In this regard, a host-dopant system may be used as a luminescent material so as to increase the color purity and the light emission efficiency through energy transfer. This is based on the principle whereby, when a dopant is smaller in energy band gap than a host accounting for the light-emitting layer, the addition of a small amount of the dopant to the host generates excitons from the light-emitting layer so that the excitons are transported to the dopant, emitting light at high efficiency. Here, light of desired wavelengths can be obtained depending on the kinds of dopant because the wavelength of the host moves to the wavelength range of the dopant.

A prerequisite for an OLED to sufficiently exhibit the outstanding above-mentioned properties is that stability and effectiveness should be backed for the materials of the organic layers in the diode, for example, hole injection materials, hole transport materials, light-emitting materials, electron transport materials, electron injection materials, etc.

Of them, materials for electron transport layers are found in Korean Patent No: 10-0691543 (Mar. 9, 2007), disclosing an organic compound which has one or two hetero-functional groups introduced at four substitution positions of the anthracene moiety thereof to excellent electron transport and hole blocking capability and emission efficiency and guarantees high stability in a thin film state. Further, Korean Patent No. 10-2012-0104204 A (Sep. 20, 2012) describes an organic compound having a substituted anthracene ring structure linked with a pyridoindole derivative, and Japanese Patent No. 2010-168363 A (Aug. 5, 2010) addresses an anthracene derivative having a pyridine naphthyl group, which allows for excellent external quantum efficiency and driving voltage properties.

Despite enormous efforts to prepare electron transport layer materials for use in organic light-emitting diodes, materials allowing for low driving voltages or high luminance efficiency have not yet been sufficiently developed and there is thus still the continued need to develop electron transport layer materials for use in organic light-emitting diodes that exhibit higher light emission efficiency and which can be driven at low voltages.

DETAILED DESCRIPTION OF THE INVENTION

Technical Problem

Accordingly, a first purpose to be accomplished by the present disclosure is to provide an organic compound for organic light-emitting diodes, which is available for an electron transport layer and exhibits more improved characteristics.

A second purpose to be accomplished by the present disclosure is to provide an organic light-emitting diode comprising the organic compound.

Technical Solution

In order to accomplish the first purpose, the present disclosure provides an organic compound for use in an electron transport layer of an organic light-emitting diode, represented by the following Chemical Formula A or B:

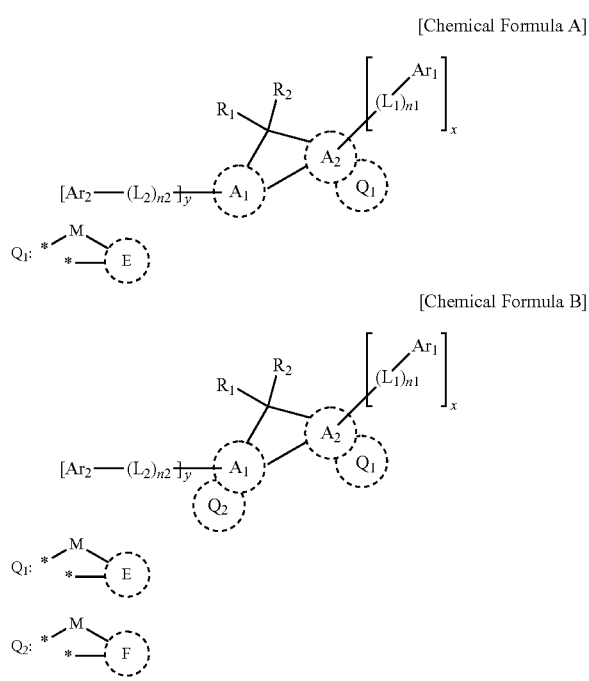

[Chemical Formula A]

[Chemical Formula B]

wherein, $A_1$, $A_2$, E, and F may be the same or different and are each independently a substituted or unsubstituted aromatic hydrocarbon ring of 6 to 50 carbon atoms or a substituted or unsubstituted heteroaromatic ring of 2 to 40 carbon atoms, wherein two adjacent carbon atoms of the aromatic ring $A_1$ and two adjacent carbon atoms of the aromatic ring $A_2$ form a 5-membered fused ring together with a carbon atom connected to both substituents $R_1$ and $R_2$;

linkers $L_1$ and $L_2$ may be the same or different and are each independently selected from among a direct bond, a substituted or unsubstituted alkylene of 1 to 60 carbon atoms, a substituted or unsubstituted alkenylene of 2 to 60 carbon atoms, a substituted or unsubstituted alkynylene of 2 to 60 carbon atoms, a substituted or unsubstituted cycloalkylene of 3 to 60 carbon atoms, a substituted or unsubstituted heterocycloalkylene of 2 to 60 carbon atoms, a substituted or unsubstituted arylene of 6 to 60 carbon atoms, and a substituted or unsubstituted heteroarylene of 2 to 60 carbon atoms;

M is any one selected from among N—$R_3$, $CR_4R_5$, $SiR_6R_7$, $GeR_8R_9$, O, S, and Se;

$Ar_1$ and $Ar_2$ may be the same or different and are each independently a substituted or unsubstituted heteroaryl of 2 to 50 carbon atoms bearing at least one nitrogen atom, n1 and n2 are each independently an integer of 1 to 3, with the proviso that when each of them is two or greater, the corresponding respective $L_1$'s and $L_2$'s are the same or different, x and y are each an integer of 0 or 1, with the proviso that x+y=1 or x+y=2, $R_1$ to $R_9$ may be the same or different and are each independently any one selected from among a hydrogen atom, a deuterium atom, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted alkylsilyl of 1 to 30 carbon atoms, a substituted or unsubstituted arylsilyl of 6 to carbon atoms, a substituted or unsubstituted alkylgermanium of 1 to 30 carbon atoms, a substituted or unsubstituted arylgermanium of 6 to 30 carbon atoms, a cyano, a nitro, and a halogen, with the proviso that $R_1$ and $R_2$ in Chemical Formula B may be bonded to each other to form a mono- or polycyclic aliphatic or aromatic ring, which may be a heterocyclic ring bearing at least one heteroatom selected from among N, O, P, Si, S, Ge, Se, and Te as a ring member;

two adjacent carbon atoms of the $A_2$ ring moiety of Chemical Formula A may occupy respective positions * of Structural Formula $Q_1$ to form a fused ring, and two adjacent carbon atoms of the $A_1$ ring moiety of Chemical Formula B may occupy respective positions * of structural Formula $Q_2$ to form a fused ring, and two adjacent carbon atoms of the $A_2$ ring moiety of Chemical Formula B may occupy respective positions * of Structural Formula $Q_1$ to form a fused ring;

wherein the term "substituted" in the expression "substituted or unsubstituted" used for Chemical Formulas A and B means having at least one substituent selected from the group consisting of a deuterium atom, a cyano, a halogen, a hydroxy, a nitro, an alkyl of 1 to 24 carbon atoms, a halogenated alkyl of to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, a heteroaryl of 2 to 24 carbon atoms or a heteroarylalkyl of 2 to 24 carbon atoms, an alkoxy of 1 to 24 carbon atoms, an alkylamino of 1 to 24 carbon atoms, an arylamino of 6 to 24 carbon atoms, a heteroarylamino of 1 to 24 carbon atoms, an alkylsilyl of 1 to 24 carbon atoms, an arylsilyl of 6 to 24 carbon atoms, and an aryloxy of 6 to 24 carbon atoms.

In order to accomplish the second purpose, the present disclosure provides an organic light-emitting diode, comprising: a first electrode; a second electrode facing the first electrode; and an organic layer interposed between the first electrode and the second electrode, wherein the organic layer includes at least one of the organic compounds represented by Chemical Formula A or B.

Advantageous Effects

According to the present disclosure, the organic compound represented by Chemical Formula A or B exhibits more improved device characteristics and thus is applicable for the fabrication of stable and excellent devices.

BRIEF DESCRIPTION OF THE DRAWINGS

FIG. 1 is a schematic view of an organic light-emitting diode according to an embodiment of the present disclosure.

MODE FOR CARRYING OUT THE INVENTION

Hereinafter, some embodiments which can be easily performed by those skilled in the art will be described with reference to the accompanying drawings. In the drawings of the disclosure, sizes and dimensions of structures are illustrated by enlarging or reducing as compared with the actual sizes and dimensions to clarify the disclosure, the known configurations are not illustrated to exhibit characteristic configurations, and the disclosure is not limited to the drawings.

When describing the principle of the embodiments of the present disclosure in detail, details of well-known functions and features may be omitted to avoid unnecessarily obscuring the presented embodiments.

In addition, the size and thickness of each configuration illustrated in the drawings are arbitrarily illustrated for the sake of convenience of explanation, and thus the present disclosure may not be necessarily limited to the illustration. Further, in the drawings, the thickness of layers and regions are illustrated in enlargement for clarity. For the sake of explanation, thicknesses of certain layers and regions are exaggerated.

Throughout the specification, when a portion may "include" a certain constituent element, unless explicitly described to the contrary, it may not be construed to exclude another constituent element but may be construed to further include other constituent elements. Further, throughout the specification, the word "on" means positioning on or below the object portion, but does not essentially mean positioning on the lower side of the object portion based on a gravity direction.

The present disclosure provides an organic compound for use in an electron transport layer of an organic light-emitting diode, represented by the following Chemical Formula A or B:

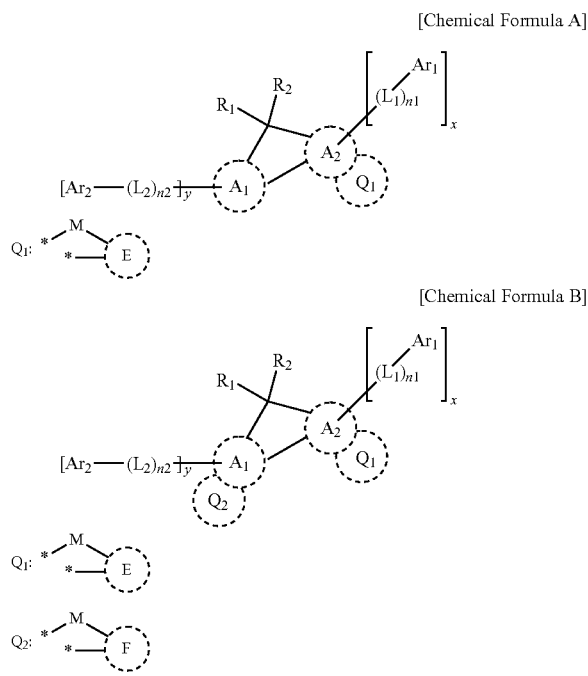

[Chemical Formula A]

[Chemical Formula B]

wherein, $A_1$, $A_2$, E, and F may be the same or different and are each independently a substituted or unsubstituted aromatic hydrocarbon ring of 6 to 50 carbon atoms or a substituted or unsubstituted heteroaromatic ring of 2 to 40 carbon atoms, wherein two adjacent carbon atoms of the aromatic ring $A_1$ and two adjacent carbon atoms of the aromatic ring $A_2$ form a 5-membered fused ring together with a carbon atom connected to both substituents $R_1$ and $R_2$;

linkers $L_1$ and $L_2$ may be the same or different and are each independently selected from among a direct bond, a substituted or unsubstituted alkylene of 1 to 60 carbon atoms, a substituted or unsubstituted alkenylene of 2 to 60 carbon atoms, a substituted or unsubstituted alkynylene of 2 to 60 carbon atoms, a substituted or unsubstituted cycloalkylene of 3 to 60 carbon atoms, a substituted or unsubstituted heterocycloalkylene of 2 to 60 carbon atoms, a substituted or unsubstituted arylene of 6 to 60 carbon atoms, and a substituted or unsubstituted heteroarylene of 2 to 60 carbon atoms;

M is any one selected from among N—$R_3$, $CR_4R_5$, $SiR_6R_7$, $GeR_8R_9$, O, S, and Se;

$Ar_1$ and $Ar_2$ may be the same or different and are each independently a substituted or unsubstituted heteroaryl of 2 to 50 carbon atoms bearing at least one nitrogen atom, n1 and n2 are each independently an integer of 1 to 3, with the proviso that when each of them is two or greater, the corresponding respective $L_1$'s and $L_2$'s are the same or different, x and y are each an integer of 0 or 1, with the proviso that x+y=1 or x+y=2, $R_1$ to $R_9$ may be the same or different and are each independently any one selected from among a hydrogen atom, a deuterium atom, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted alkylsilyl of 1 to 30 carbon atoms, a substituted or unsubstituted arylsilyl of 6 to 30 carbon atoms, a substituted or unsubstituted alkylgermanium of 1 to 30 carbon atoms, a substituted or unsubstituted arylgermanium of 6 to 30 carbon atoms, a cyano, a nitro, and a halogen, with the proviso that $R_1$ and $R_2$ in Chemical Formula B may be bonded to each other to form a mono- or polycyclic aliphatic or aromatic ring, which may be a heterocyclic ring bearing at least one heteroatom selected from among N, O, P, Si, S, Ge, Se, and Te as a ring member;

two adjacent carbon atoms of the $A_2$ ring moiety of Chemical Formula A may occupy respective positions * of Structural Formula $Q_1$ to form a fused ring, and two adjacent carbon atoms of the $A_1$ ring moiety of Chemical Formula B may occupy respective positions * of structural Formula $Q_2$ to form a fused ring, and two adjacent carbon atoms of the $A_2$ ring moiety of Chemical Formula B may occupy respective positions * of Structural Formula $Q_1$ to form a fused ring;

wherein the term "substituted" in the expression "substituted or unsubstituted" used for Chemical Formulas A and B means having at least one substituent selected from the group consisting of a deuterium atom, a cyano, a halogen, a hydroxy, a nitro, an alkyl of 1 to 24 carbon atoms, a halogenated alkyl of to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, a heteroaryl of 2 to 24 carbon atoms or a heteroarylalkyl of 2 to 24 carbon atoms, an alkoxy of 1 to 24 carbon atoms, an alkylamino of 1 to 24 carbon atoms, an arylamino of 6 to 24 carbon atoms, a heteroarylamino of 1 to 24 carbon atoms, an alkylsilyl of 1 to 24 carbon atoms, an arylsilyl of 6 to 24 carbon atoms, and an aryloxy of 6 to 24 carbon atoms.

As used herein, the term "aryl" as a substituent used in the compounds of the present disclosure means an organic radical derived from an aromatic hydrocarbon by removing a hydrogen atom and may further include a fused ring that is formed by adjacent substituents on the organic radical.

Concrete examples of the aryl include aromatic radicals such as phenyl, naphthyl, tetrahydronaphthyl, etc. at least one hydrogen atom of which may be substituted by a deuterium atom, a halogen atom, a hydroxy, a nitro, a cyano, a silyl, an amino (—$NH_2$, —NH(R), or —N(R') (R'') wherein R' and R'' are each independently an alkyl of 1 to 10 carbon atoms, in this case, called "alkylamino"), an amidino, a hydrazine, a hydrazone, a carboxyl, a sulfonic acid, a phosphoric acid, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, a heteroaryl of 2 to 24 carbon atoms, or a heteroarylalkyl of 2 to 24 carbon atoms.

The substituent heteroaryl used in the compound of the present disclosure refers to a cyclic aromatic system of 2 to 24 carbon atoms bearing one to three heteroatoms selected from among N, O, P, and S. In the aromatic system, two or more rings may be fused. One or more hydrogen atoms on the heteroaryl may be substituted with the same substituents as in the aryl.

Examples of the substituent alkyl useful in the present disclosure include methyl, ethyl, propyl, isopropyl, isobutyl, sec-butyl, tert-butyl, pentyl, iso-amyl, and hexyl. At least one hydrogen atom of the alkyl may be substituted with the same substituent as in the aryl.

Examples of the substituent alkoxy useful in the present disclosure include methoxy, ethoxy, propoxy, isobutyloxy, sec-butyloxy, pentyloxy, iso-amyloxy, and hexyloxy. At least one hydrogen atom of the alkoxy may be substituted with the same substituent as in the aryl.

Representative among examples of the substituent silyl useful in the present disclosure are trimethylsilyl, triethylsilyl, triphenylsilyl, trimethoxysilyl, dimethoxyphenylsilyl, diphenylmethylsilyl, diphenylvinylsilyl, methylcyclobutylsilyl, and dimethylfurylsilyl. One or more hydrogen atoms of the silyl may be substituted with the same substituent as in the aryl.

The organic compound, represented by Chemical Formula A or B, of the present invention is: 1) a compound in which the heteroaryl $Ar_1$ is linked only to the $A_2$ ring moiety via the linker $L_1$ (x+y=1 wherein x is 1 and y is zero) or in which the heteroaryl $Ar_2$ is linked only to the $A_1$ ring moiety via the linker $L_2$ (x+y=1 wherein x is zero and y is 1), or 2) a compound in which the heteroaryl $Ar_1$ is linked to the $A_2$ ring moiety via the linker $L_1$ and the heteroaryl $Ar_2$ is linked to the $A_1$ ring moiety via the linker $L_2$ (x+y=2 wherein x and y are each 1).

When used in an electron transport layer of an organic light-emitting diode, the compound according to the present disclosure can exhibit improved diode characteristics including luminance efficiency, low-voltage driving, etc.

The heterocyclic compound according to one embodiment of the present disclosure may be a compound represented by Chemical Formula A wherein Structural Formula $Q_1$ is coupled with the $A_2$ ring moiety, and x is 1 and y is zero such that only the linker $L_1$ including $Ar_1$ is bonded to the $A_2$ ring moiety.

The heterocyclic compound according to another embodiment of the present disclosure may be a compound represented by Chemical Formula A wherein Structural Formula $Q_1$ is coupled with the $A_2$ ring moiety, and x is zero and y is 1 such that only the linker $L_2$ including $Ar_2$ is bonded to the $A_1$ ring moiety.

The heterocyclic compound according to another embodiment of the present disclosure may be a compound represented by Chemical Formula A wherein Structural Formula $Q_1$ is coupled with the $A_2$ ring moiety, and x is 1 and y is 1 such that the linker $L_1$ including $Ar_1$ and the linker $L_2$ including $Ar_2$ are bonded to $A_2$ and $A_1$ ring moieties, respectively.

The heterocyclic compound according to another embodiment of the present disclosure may be a compound represented by Chemical Formula B wherein Structural Formulas $Q_1$ and $Q_2$ are respectively coupled with the $A_2$ and $A_1$ ring moieties, and x is 1 and y is zero such that only the linker $L_1$ including $Ar_1$ is bonded to the $A_2$ ring moiety.

The heterocyclic compound according to another embodiment of the present disclosure may be a compound represented by Chemical Formula B wherein Structural Formulas $Q_1$ and $Q_2$ are respectively coupled with the $A_2$ and $A_1$ ring moieties, and x is zero and y is 1 such that only the linker $L_2$ including $Ar_2$ is bonded to the $A_1$ ring moiety.

The heterocyclic compound according to another embodiment of the present disclosure may be a compound represented by Chemical Formula B wherein Structural Formulas $Q_1$ and $Q_2$ are respectively coupled with the $A_2$ and $A_1$ ring moieties, and x is 1 and y is 1 such that the linker $L_1$ including $Ar_1$ and the linker $L_2$ including $Ar_2$ are bonded to $A_2$ and $A_1$ ring moieties, respectively.

In Chemical Formula A or B, $A_1$, $A_2$, E, and F may be the same or different, and are each independently substituted or unsubstituted aromatic hydrocarbon rings of 6 to 50 carbon atoms.

As stated above, when $A_1$, $A_2$, E, and F in Chemical Formula A or B are each independently substituted or unsubstituted aromatic hydrocarbon rings of 6 to 50 carbon atoms, the substituted or unsubstituted aromatic hydrocarbon rings of 6 to 50 carbon atoms may be the same or different and each be independently selected from among compounds represented by Structural Formulas 10 to 21:

[Structural Formula 10]

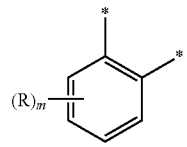

[Structural Formula 11]

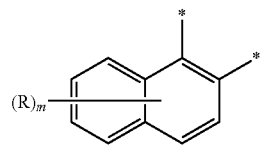

[Structural Formula 12]

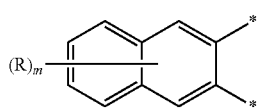

[Structural Formula 13]

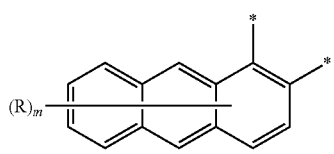

[Structural Formula 14]

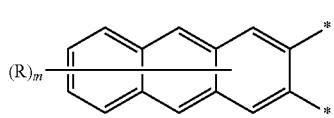

[Structural Formula 15]

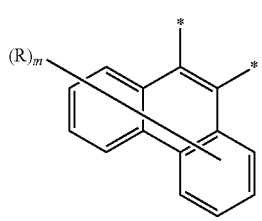

[Structural Formula 16]

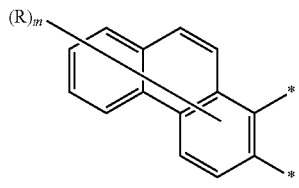

[Structural Formula 17]

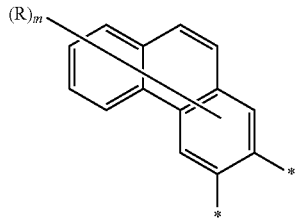

[Structural Formula 18]

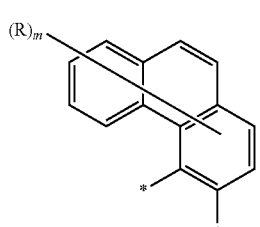

[Structural Formula 19]

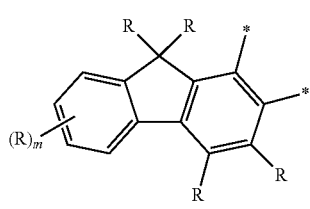

[Structural Formula 20]

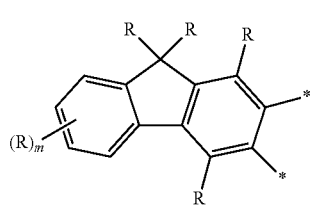

[Structural Formula 21]

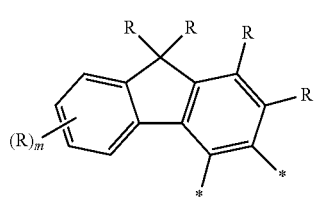

wherein,

"-*" denotes a bonding site for forming a 5-membered ring bearing the carbon atom connected to the substituents $R_1$ and $R_2$ or a bonding site for forming a 5-membered ring bearing M of Structural Formulas $Q_1$ and $Q_2$;

when one of the aromatic hydrocarbon rings of [Structural Formula 10] to [Structural Formula 21] for $A_1$ or $A_2$ is bonded to Structural Formula $Q_1$ or $Q_2$, two adjacent carbon atoms of the aromatic hydrocarbon ring occupy respective positions * of Structural Formula $Q_1$ or $Q_2$ to form a fused ring;

R's are the same as defined above for $R_1$ and $R_2$, and m is an integer of 1 to 8, with the proviso that when m is 2 or greater or two or more R's exist, the corresponding R's may be the same or different.

According to one embodiment of the present disclosure, the linkers $L_1$ and $L_2$ in Chemical Formula A or B may be a single bond or one selected from among compounds represented by the following Structural Formulas 22 to 30, and n1 and n2 may each be 1 or 2:

[Structural Formula 22]

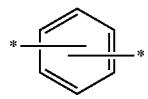

[Structural Formula 23]

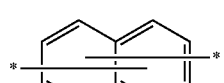

[Structural Formula 24]

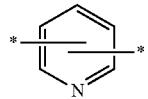

[Structural Formula 25]

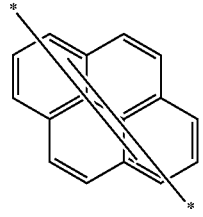

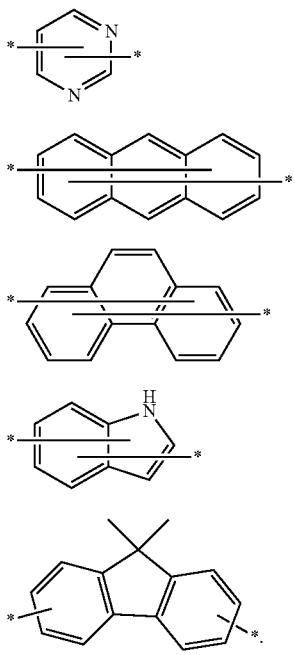

[Structural Formula 26]

[Structural Formula 27]

[Structural Formula 28]

[Structural Formula 29]

[Structural Formula 30]

In the linkers $L_1$ and $L_2$, each of the unsubstituted carbon atoms of the aromatic ring moiety is bound with a hydrogen atom or a deuterium atom.

In Chemical Formulas A and B, which account for the compounds according to the present disclosure, the following condition may be satisfied: $x+y=1$.

In Chemical Formulas A and B, when substituents $Ar_1$ and $Ar_2$ are a substituted or unsubstituted heteroaryl of 2 to 50 carbon atoms bearing at least one nitrogen atoms, the heteroaryl may be any one selected from among the following Structural Formulas 1 to 3:

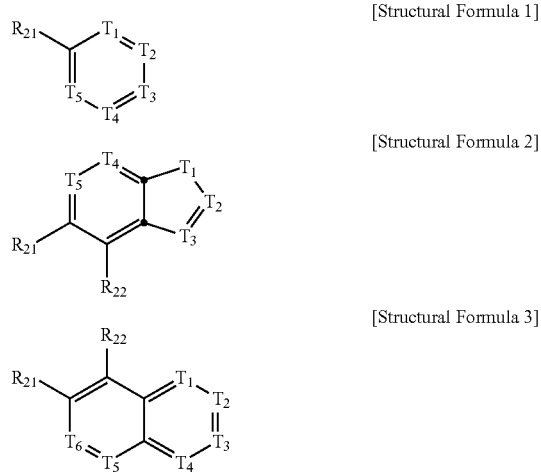

[Structural Formula 1]

[Structural Formula 2]

[Structural Formula 3]

wherein $T_1$ to $T_6$ may be the same or different and are each independently one selected from among $C(R_{11})$, $C(R_{11})(R_{11})$, N, $N(R_{13})$, O, and S; and $R_{11}$ to $R_{13}$, $R_{21}$, and $R_{22}$ may be the same or different and are each independently one selected from among a hydrogen atom, a deuterium atom, a substituted or unsubstituted alkyl of 1 to 30 carbon atoms, a substituted or unsubstituted aryl of 6 to 50 carbon atoms, a substituted or unsubstituted cycloalkyl of 3 to 30 carbon atoms, a substituted or unsubstituted aryl of 6 to 50 carbon atoms, and a substituted or unsubstituted heteroaryl of 2 to 50 carbon atoms bearing O, N, or S as a heteroatom, with the proviso that one of $R_{11}$ to $R_{13}$, $R_{21}$, and $R_{22}$ represents a single bond to the linker $L_1$ or $L_2$ in Chemical Formulas A and B.

In addition, the substituents represented by Structural Formulas 1 to 3 may be heteroaryl radicals wherein one to three nitrogen atoms, instead of carbon atoms, exist in the aromatic ring moiety.

Here, the compound of Structural Formula 2 may include the compound represented by the following Structural Formula 2-1 due to a resonance structure based on delocalized electrons:

[Structural Formula 2-1]

Here, the substituents represented by Structural Formulas 1 to 3 may be heteroaryl radicals wherein one to three nitrogen atoms, instead of carbon atoms, exist in the aromatic ring moiety.

Further, $Ar_1$ and $Ar_2$ in Chemical Formulas A and B may each be one of the following substituents 201 to 413:

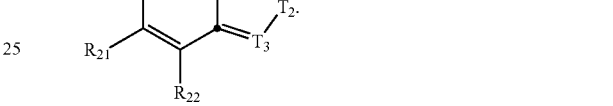

[Substituent 201]

[Substituent 202]

[Substituent 203]

[Substituent 204]

[Substituent 205]

[Substituent 206]

[Substituent 301]

[Substituent 302]

[Substituent 303]

[Substituent 304]

[Substituent 305]

[Substituent 306]

[Substituent 307]

[Substituent 308]

[Substituent 401]

[Substituent 402]

[Substituent 403]

[Substituent 404]

[Substituent 405]

[Substituent 406]

[Substituent 407]

[Substituent 408]

[Substituent 409]

[Substituent 410]

[Substituent 411]

[Substituent 412]

[Substituent 413]

wherein,

R's may be the same or different and are each independently selected from among a hydrogen atom, a deuterium atom, a halogen atom, a hydroxyl, a cyano, a nitro, an amino, an amidino, a hydrazine, a hydrazone, a carboxyl or a salt thereof, a sulfonic acid or a salt thereof, a phosphoric acid or a salt thereof, a substituted or unsubstituted alkyl of 1 to 20 carbon atoms, a substituted or unsubstituted akenyl of 2 to 20 carbon atoms, a substituted or unsubstituted alkynyl of 2 to 20 carbon atoms, a substituted or unsubstituted alkoxy of 1 to 20 carbon atoms, a substituted or unsubstituted alkylthio of 1 to 20 carbon atoms, a substituted or unsubstituted cycloalkyl of 3 to 20 carbon atoms, a substituted or unsubstituted aryl of 6 to 30 carbon atoms, a substituted or unsubstituted aryloxy of 6 to 30 carbon atoms, a substituted or unsubstituted arylthio of 6 to 30 carbon atoms, a substituted or unsubstituted heteroaryl of 2 to 30 carbon atoms, a substituted or unsubstituted (alkyl)amino of 1 to 20 carbon atoms, a di(substituted or unsubstituted alkyl)amino of 1 to 20 carbon atoms, a substituted or unsubstituted arylamino of 6 to 30 carbon atoms, a di(substituted or unsubstituted aryl)amino of 6 to 30 carbon atoms, a substituted or unsubstituted alkylsilyl of 1 to 30 carbon atoms, a substituted or unsubstituted arylsilyl of 6 to 30 carbon atoms, geramanium, phosphorous, and boron, wherein the substitutents may form a fused ring with adjacent groups;

n is an integer of 0 to 9;

the aromatic ring moieties within the heteroaryl radicals of Substituents 201 to 413 each have a hydrogen atom on the carbon members to which the substituent R is not bonded; and one of R's represents a single bond to $L_1$ or $L_2$ in Chemical Formula A or B.

Concrete examples of the heteroaryl radicals for $Ar_1$ and $Ar_2$ of the present disclosure include a substituted or unsubstituted imidazolyl, a substituted or unsubstituted triazolyl, a substituted or unsubstituted tetrazolyl, a substituted or unsubstituted carbazolyl, a substituted or unsubstituted oxadiazolyl, a substituted or unsubstituted oxatriazolyl, a substituted or unsubstituted thiatriazolyl, a substituted or unsubstituted benzimidazolyl, a substituted or unsubstituted benzotriazolyl, a substituted or unsubstituted pyridinyl, a substituted or unsubstituted pyrimidinyl, a substituted or unsubstituted triazinyl, a substituted or unsubstituted pyrazinyl, a substituted or unsubstituted pyridazinyl, a substituted or unsubstituted purinyl, a substituted or unsubstituted quinolinyl, a substituted or unsubstituted isoquinolinyl, a substituted or unsubstituted phthalazinyl, a substituted or unsubstituted naphpyridinyl, a substituted or unsubstituted quinoxalinyl, a substituted or unsubstituted quinazolinyl, a substituted or unsubstituted acridinyl, a substituted or unsubstituted phenanthrolinyl, a substituted or unsubstituted phenazinyl, and a combination thereof, but are not limited thereto.

Concrete examples of the organic compound represented by Chemical Formula A or B include, but are not limited to, compounds represented by the following Chemical Formulas 1 to 101:

<Chemical Formula 1>

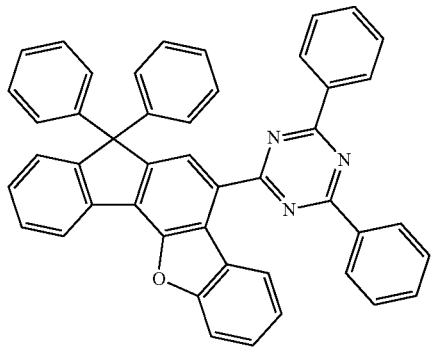

<Chemical Formula 2>

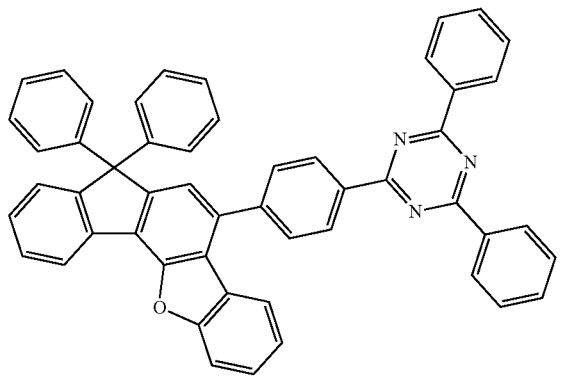

<Chemical Formula 3>

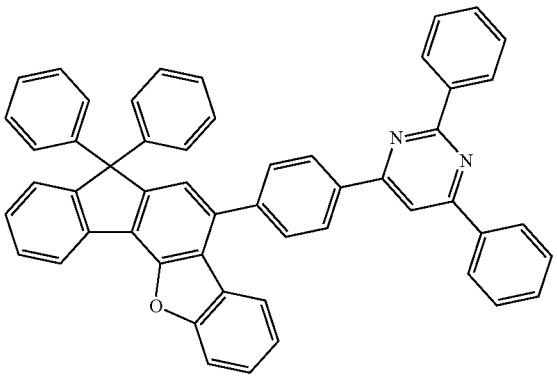

<Chemical Formula 4>

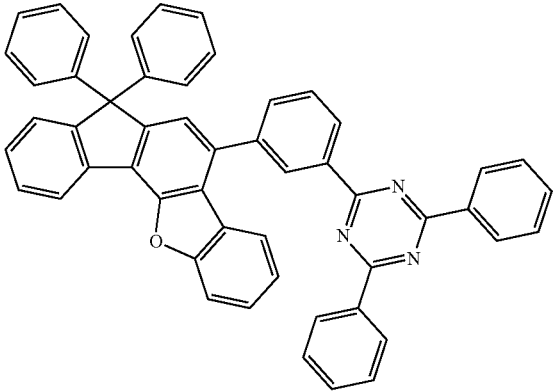

<Chemical Formula 5>

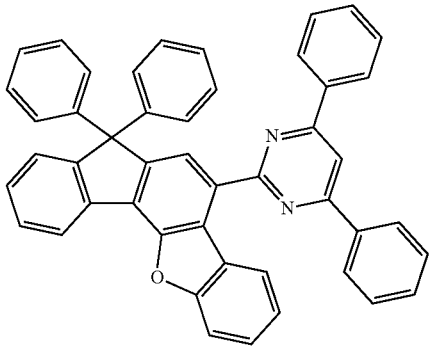

<Chemical Formula 6>

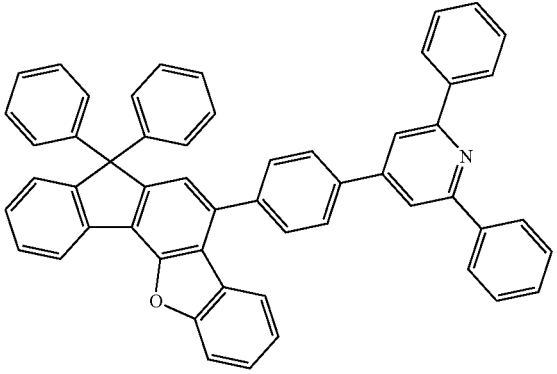

<Chemical Formula 7>
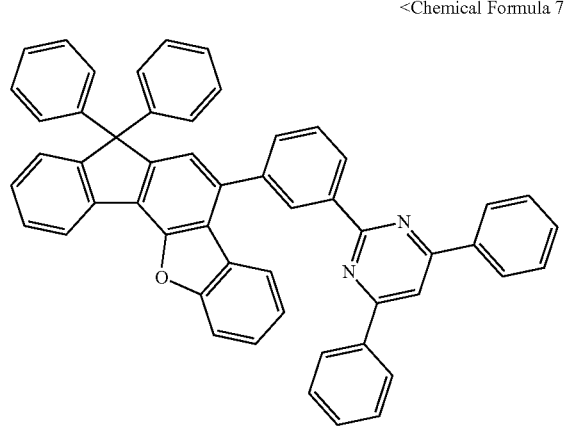
<Chemical Formula 8>
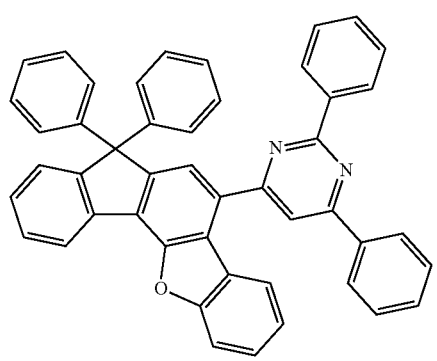
<Chemical Formula 9>
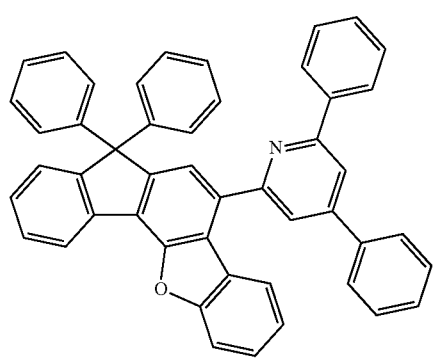
<Chemical Formula 10>
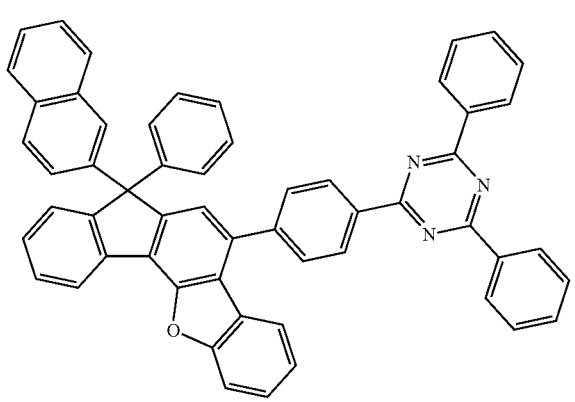
<Chemical Formula 11>
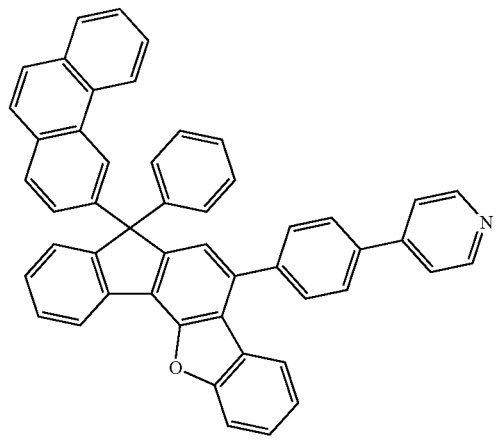
<Chemical Formula 12>
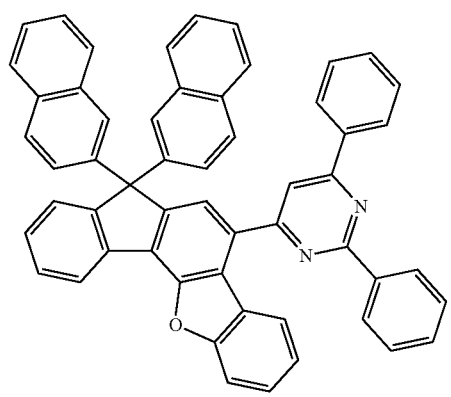
<Chemical Formula 13>
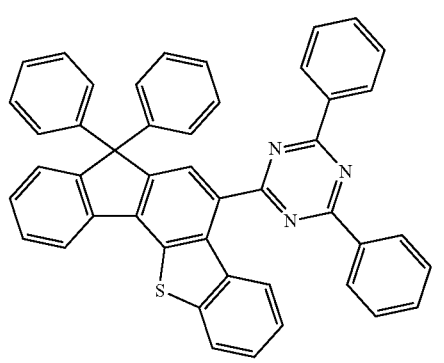
<Chemical Formula 14>
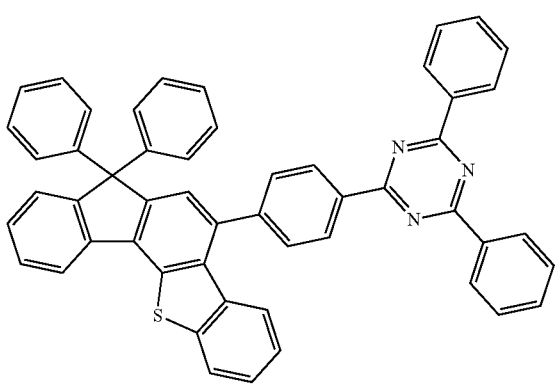

<Chemical Formula 15>
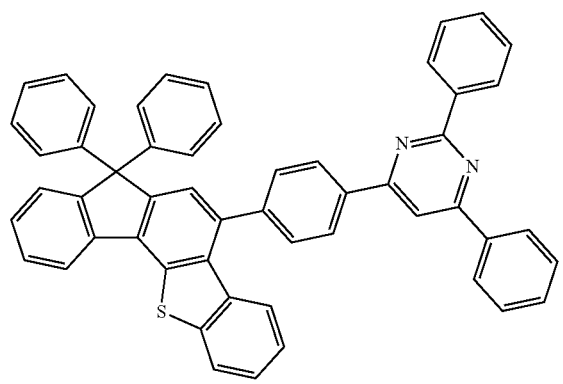
<Chemical Formula 16>
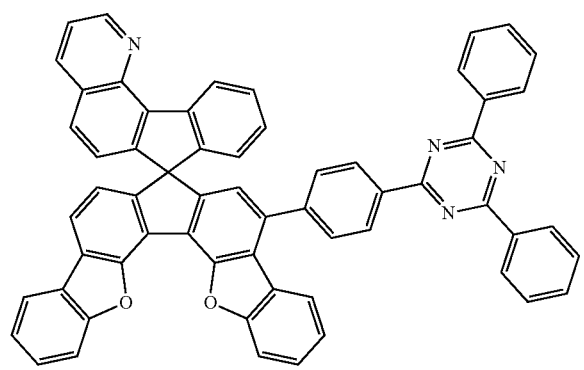
<Chemical Formula 17>
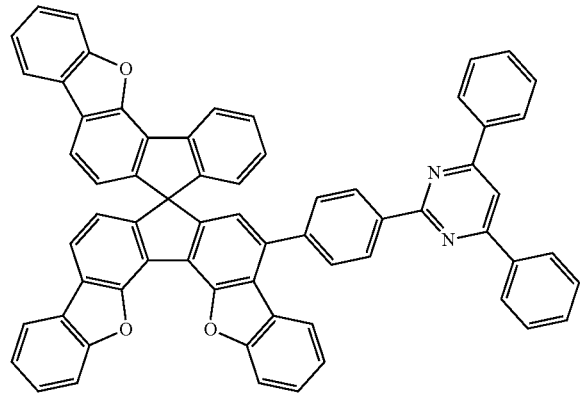
<Chemical Formula 18>
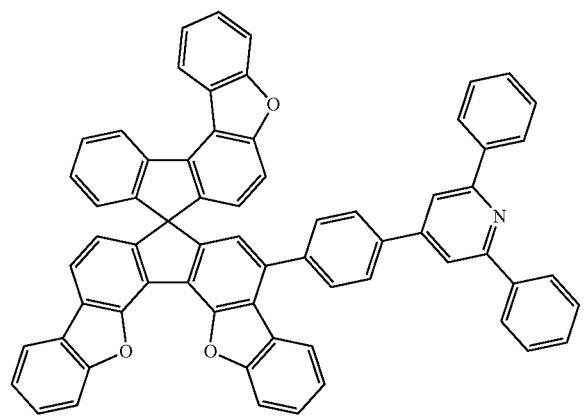
<Chemical Formula 19>
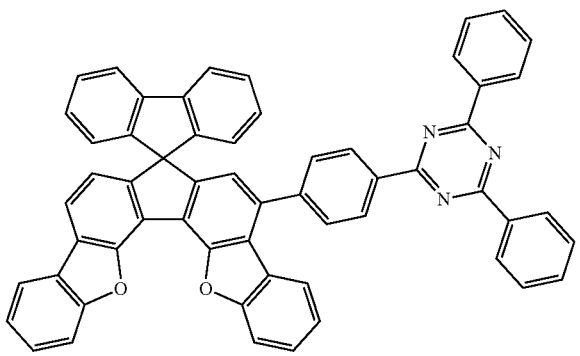
<Chemical Formula 20>
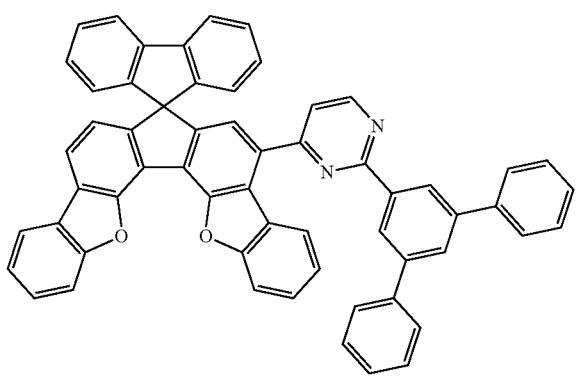
<Chemical Formula 21>
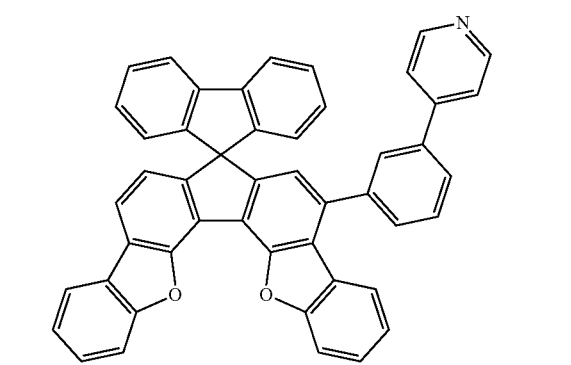
<Chemical Formula 22>
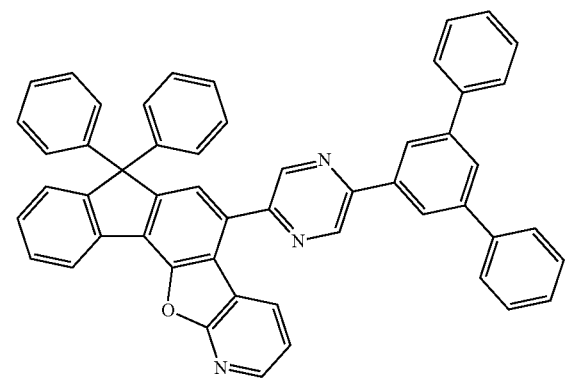

<Chemical Formula 23>
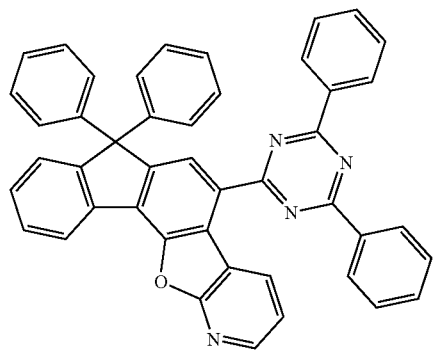
<Chemical Formula 24>
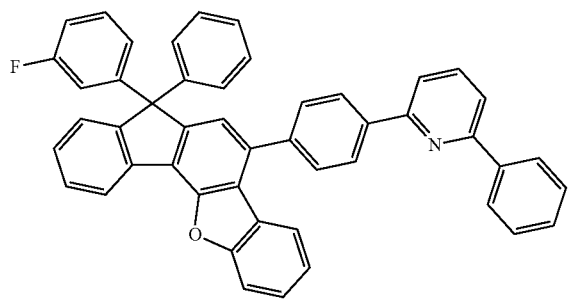
<Chemical Formula 25>
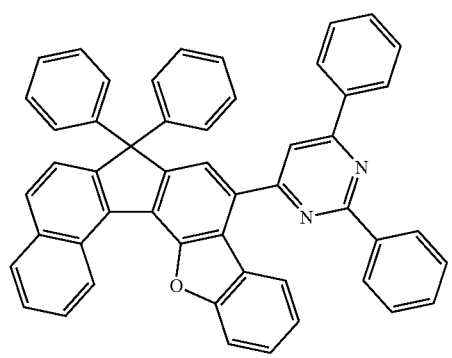
<Chemical Formula 26>
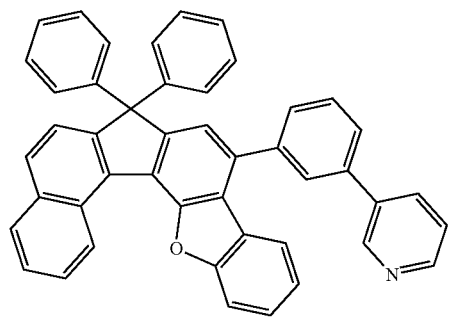
<Chemical Formula 27>
<Chemical Formula 28>
<Chemical Formula 29>
<Chemical Formula 30>
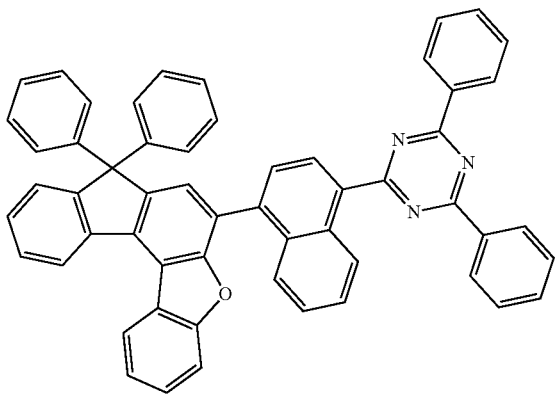

<Chemical Formula 31>
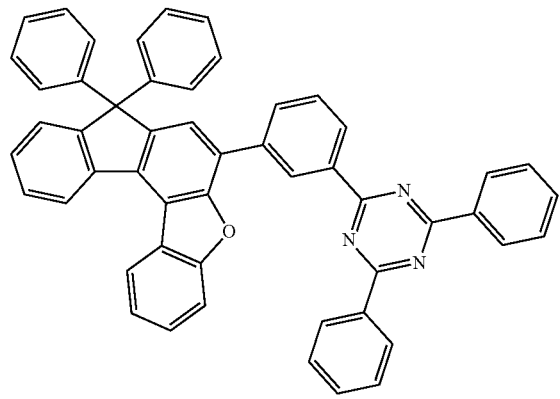
<Chemical Formula 32>
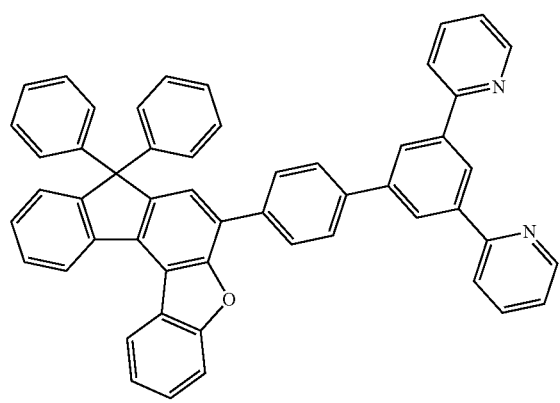
<Chemical Formula 33>
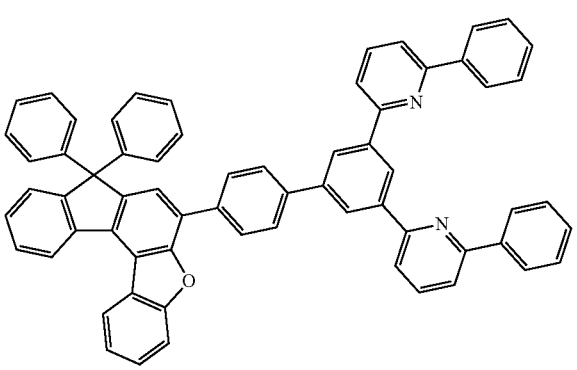
<Chemical Formula 34>
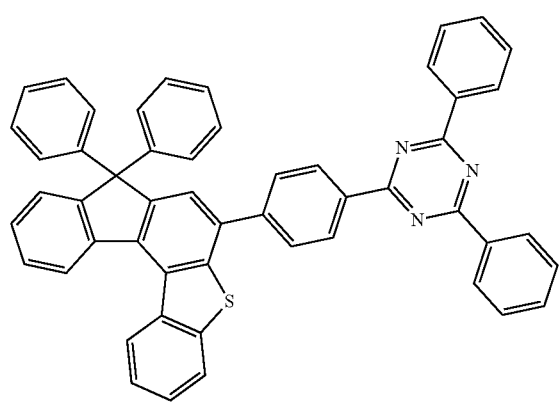
<Chemical Formula 35>
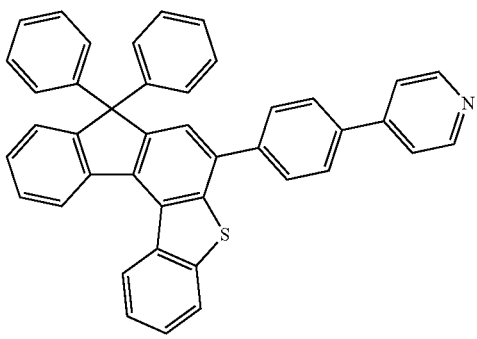
<Chemical Formula 36>
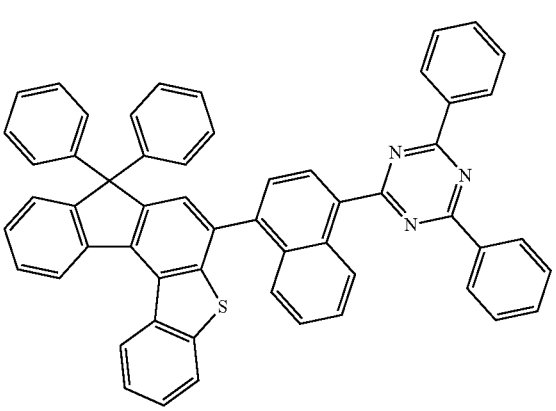
<Chemical Formula 37>
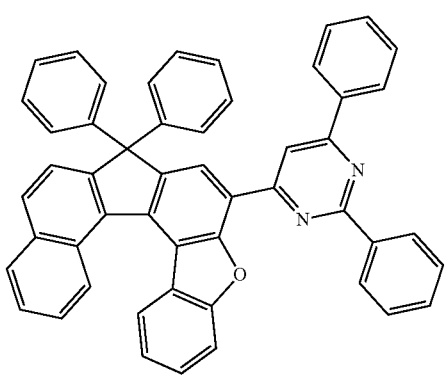
<Chemical Formula 38>
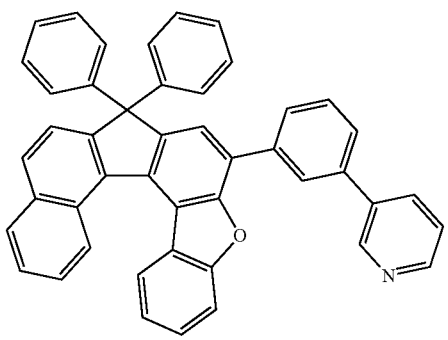

<Chemical Formula 39>
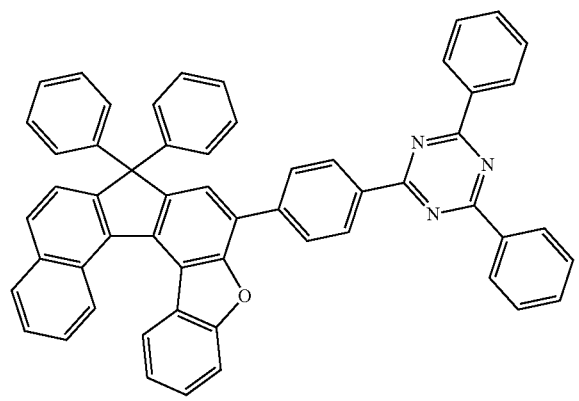
<Chemical Formula 40>
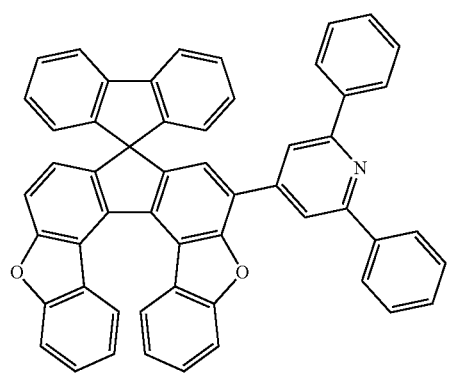
<Chemical Formula 41>
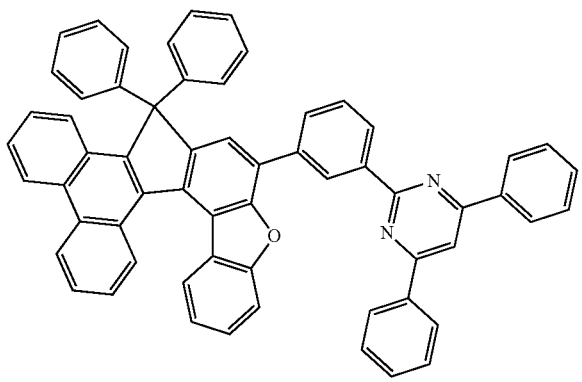
<Chemical Formula 42>
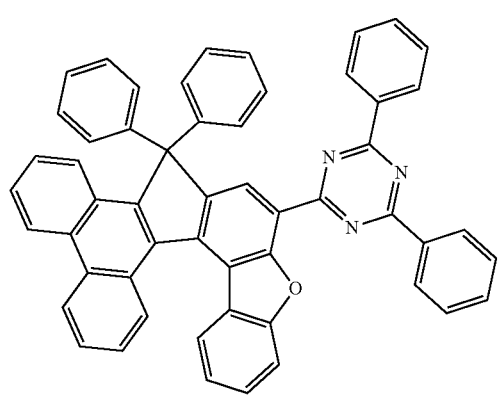
<Chemical Formula 43>
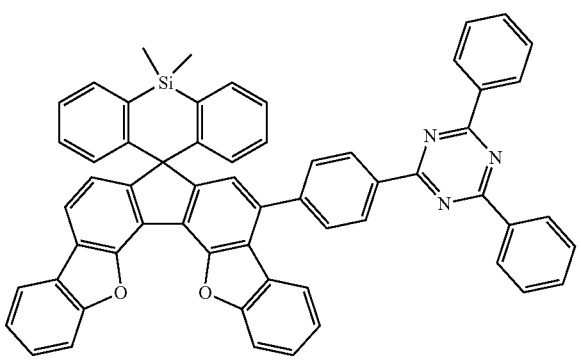
<Chemical Formula 44>
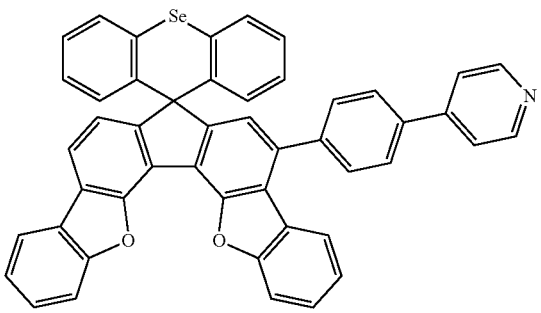
<Chemical Formula 45>
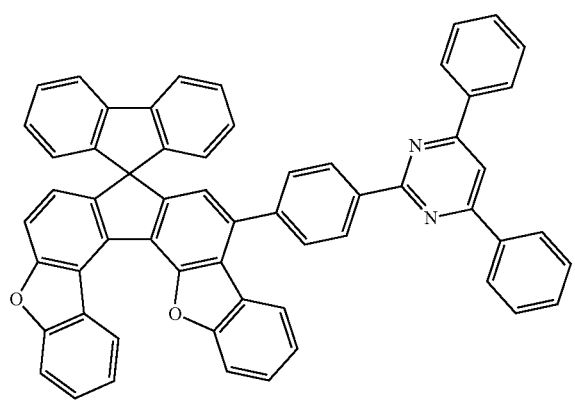
<Chemical Formula 46>

<Chemical Formula 47>
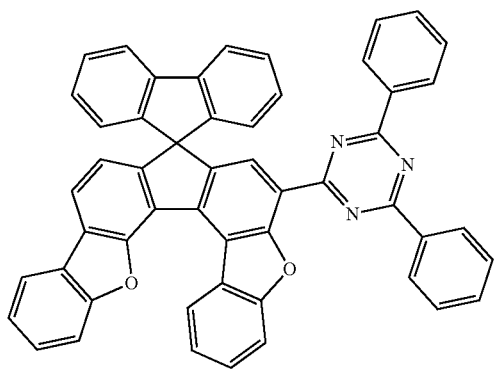
<Chemical Formula 48>
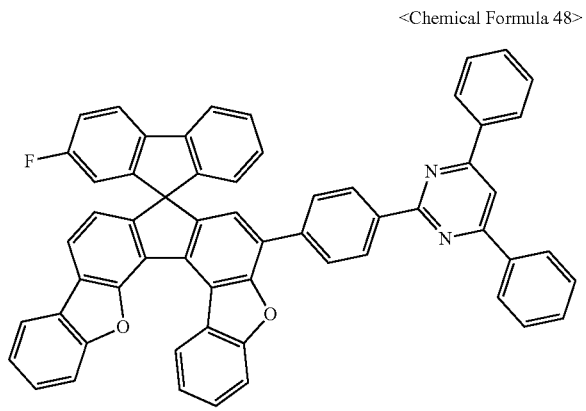
<Chemical Formula 49>
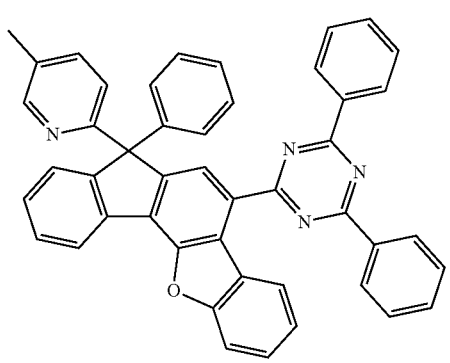
<Chemical Formula 50>
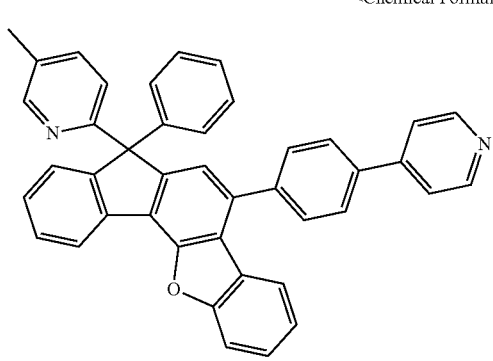
<Chemical Formula 51>
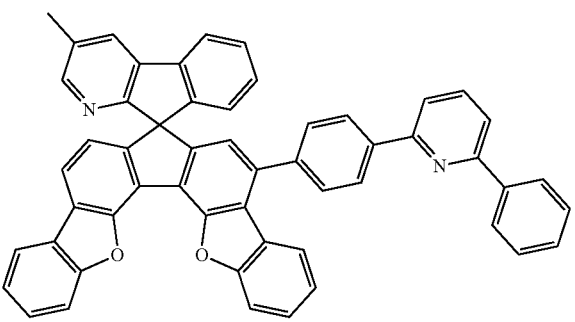
<Chemical Formula 52>
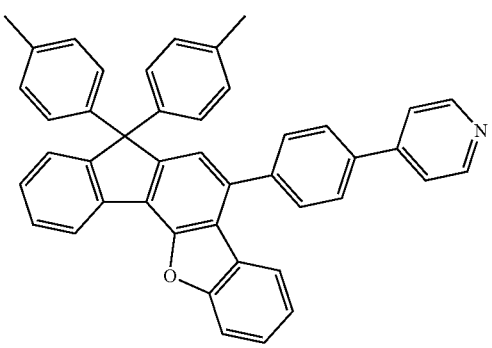
<Chemical Formula 53>
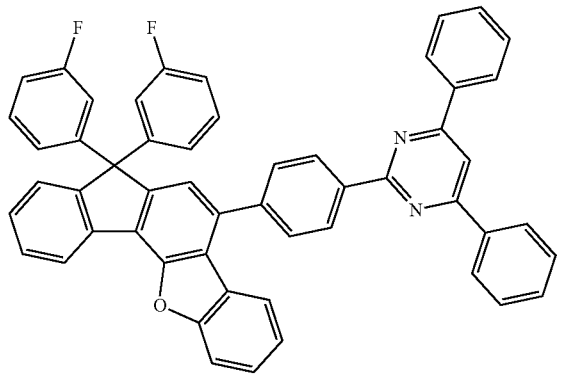
<Chemical Formula 54>
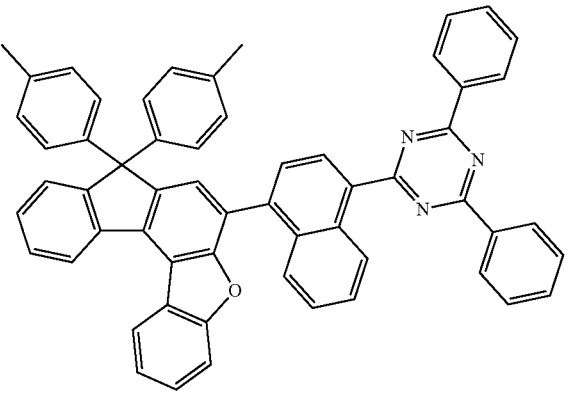

<Chemical Formula 55>
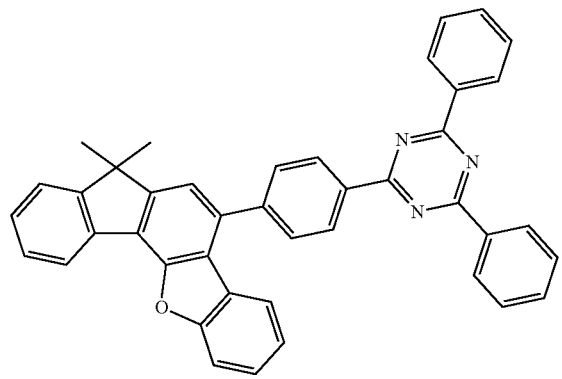
<Chemical Formula 56>
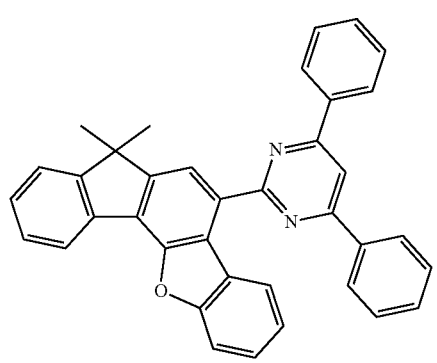
<Chemical Formula 57>
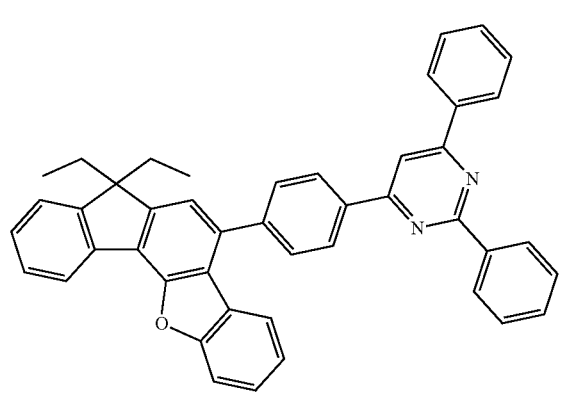
<Chemical Formula 58>
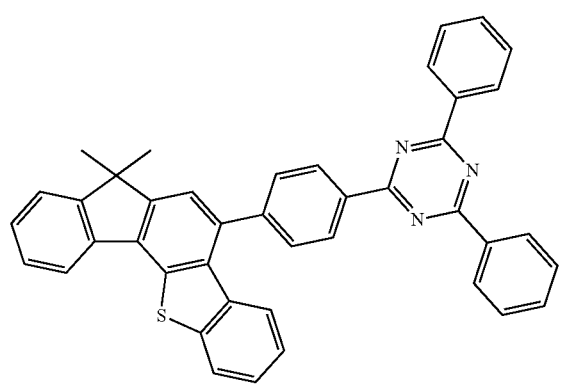
<Chemical Formula 59>
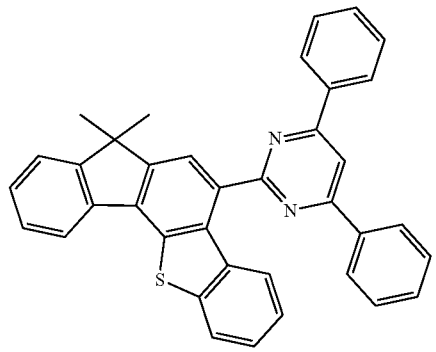
<Chemical Formula 60>
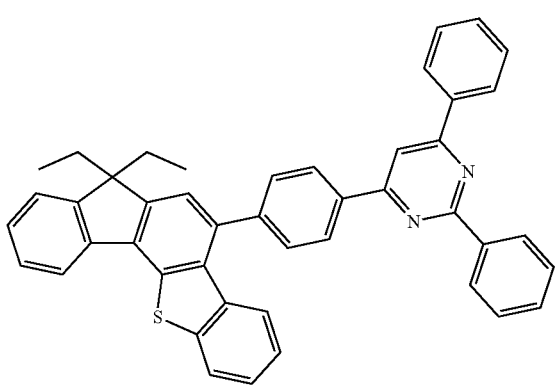
<Chemical Formula 61>
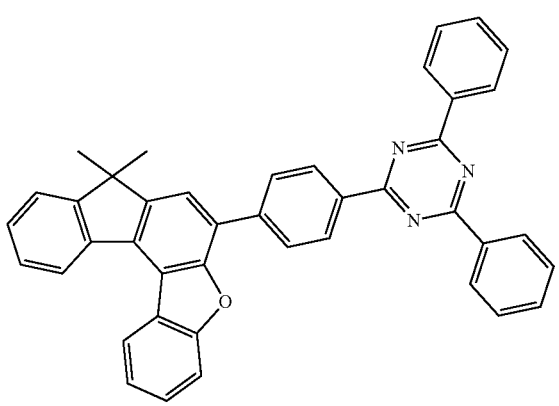
<Chemical Formula 62>
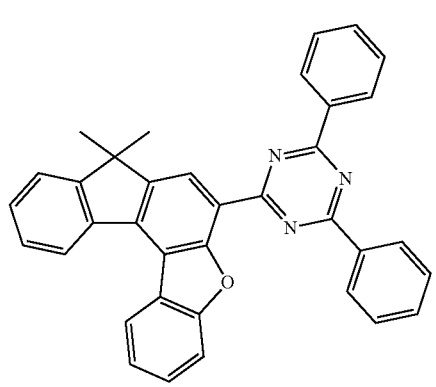

<Chemical Formula 63>
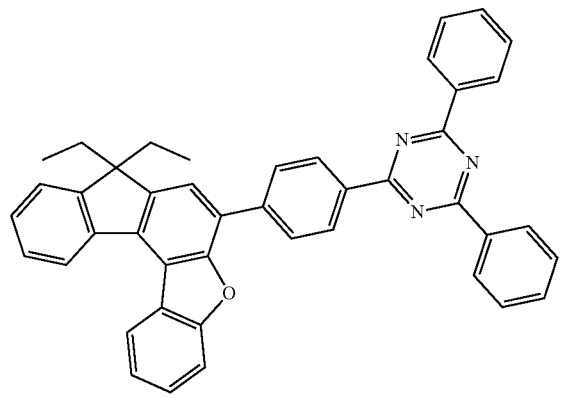
<Chemical Formula 64>
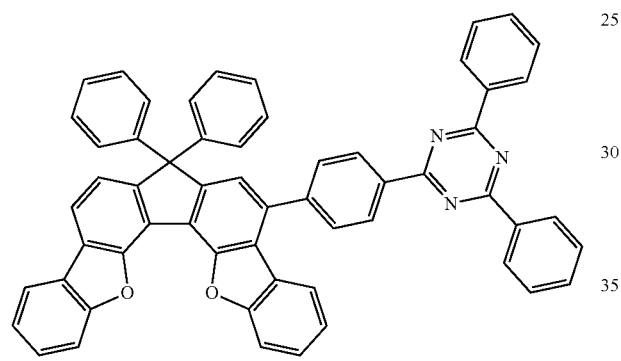
<Chemical Formula 65>
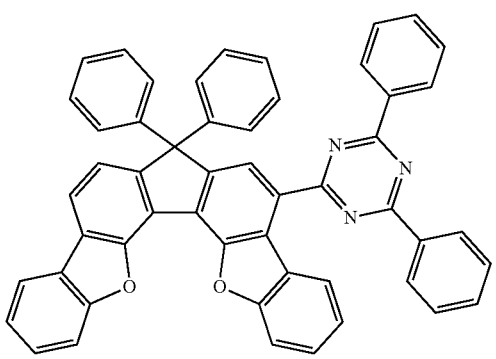
<Chemical Formula 66>
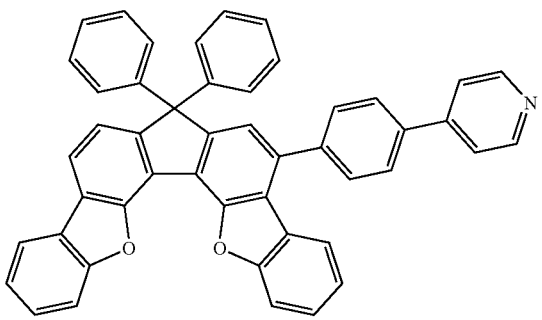
<Chemical Formula 67>
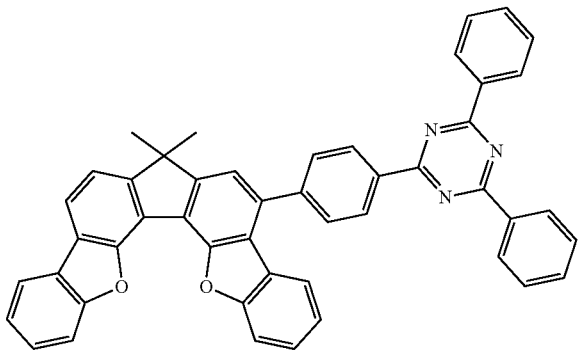
<Chemical Formula 68>
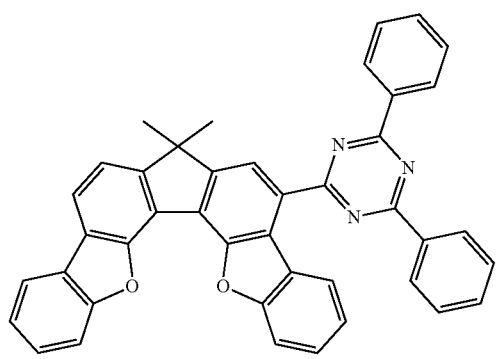
<Chemical Formula 69>
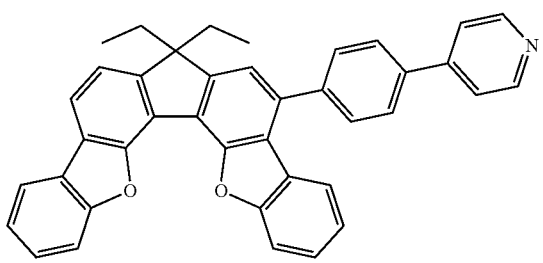
<Chemical Formula 70>
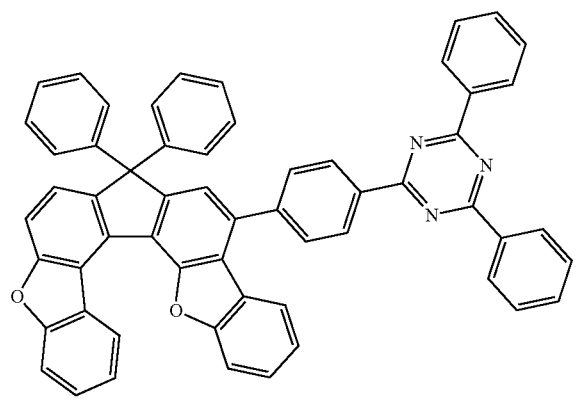

<Chemical Formula 71>
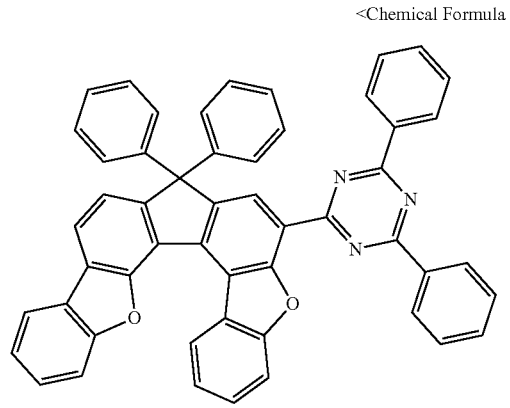
<Chemical Formula 72>
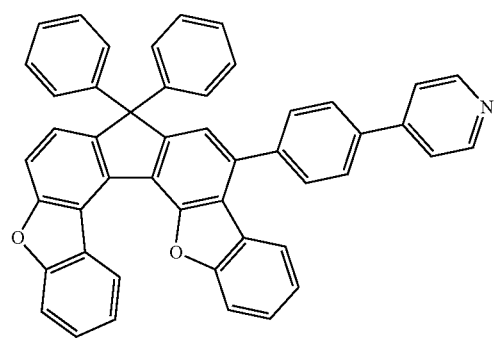
<Chemical Formula 73>
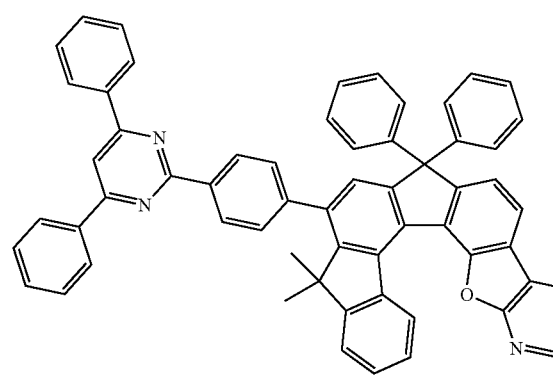
<Chemical Formula 74>
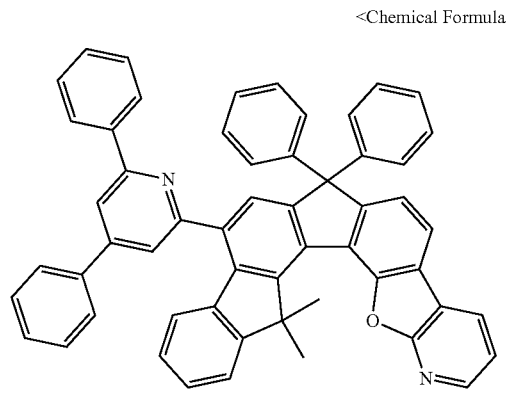
<Chemical Formula 75>
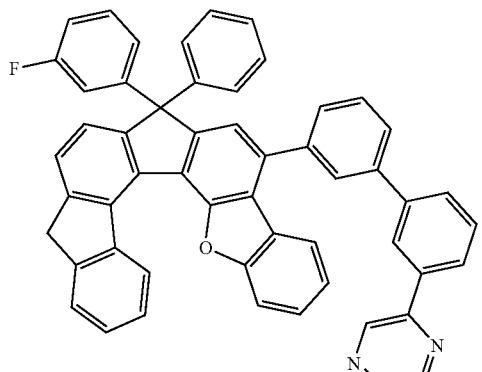
<Chemical Formula 76>
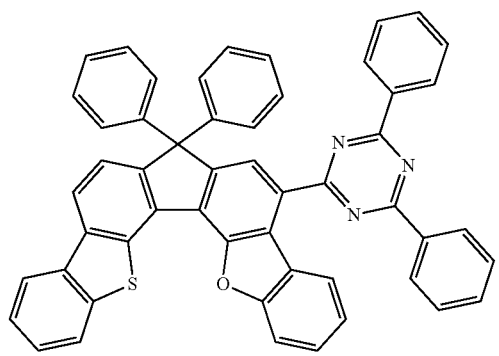
<Chemical Formula 77>
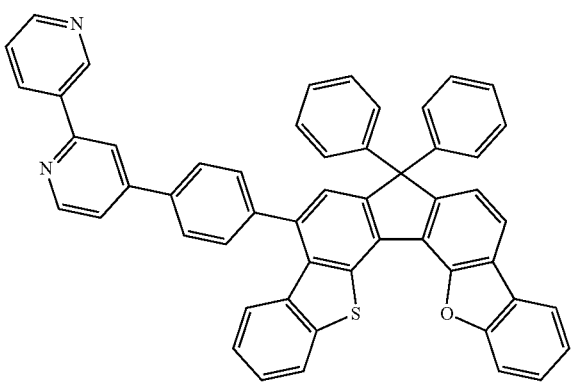
<Chemical Formula 78>
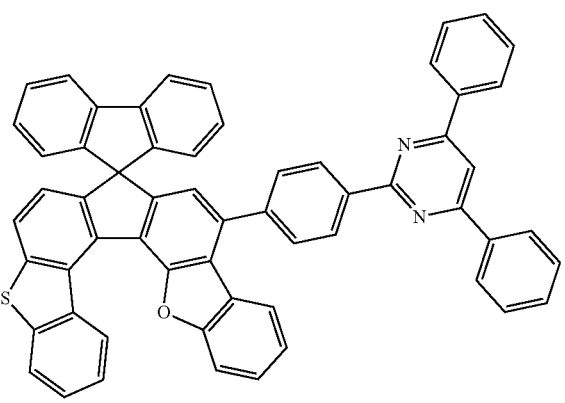

<Chemical Formula 79>
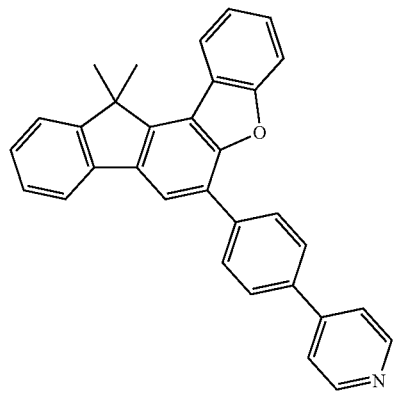
<Chemical Formula 80>
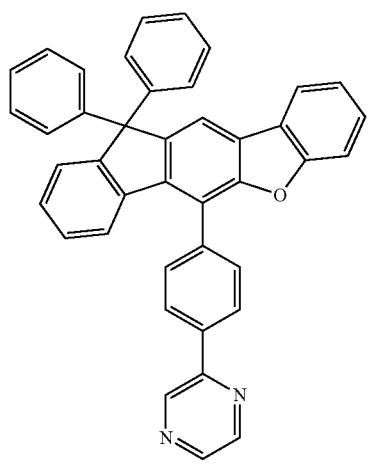
<Chemical Formula 81>
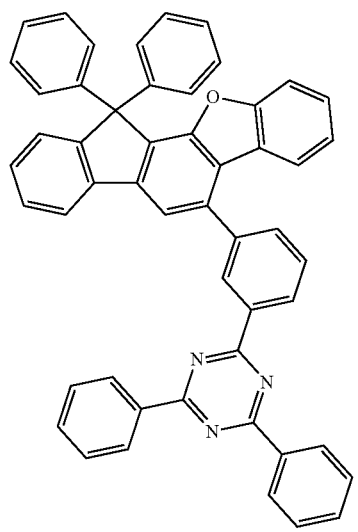
<Chemical Formula 82>
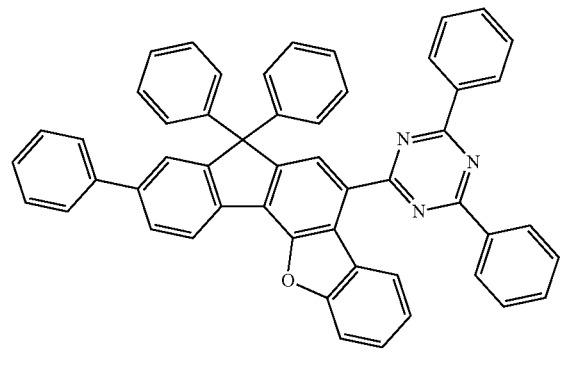
<Chemical Formula 83>
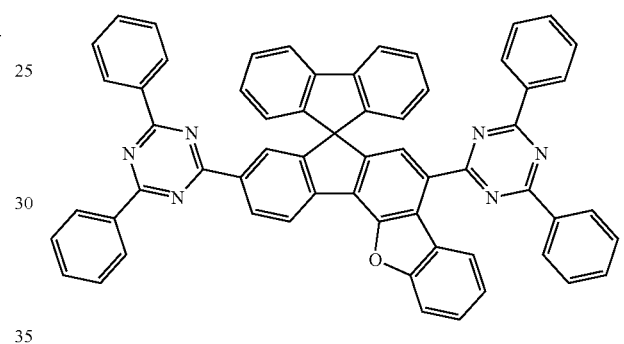
<Chemical Formula 84>
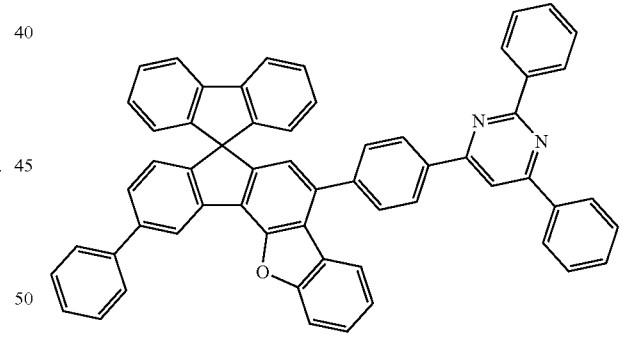
<Chemical Formula 85>
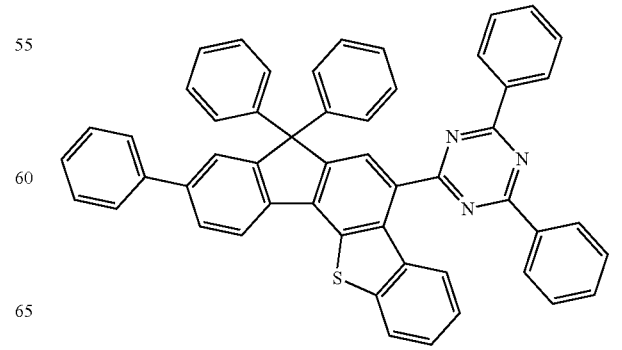

<Chemical Formula 86>
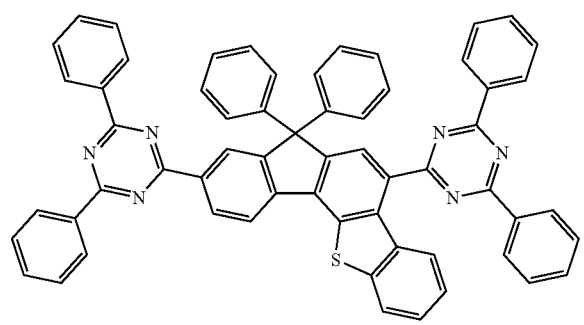
<Chemical Formula 87>
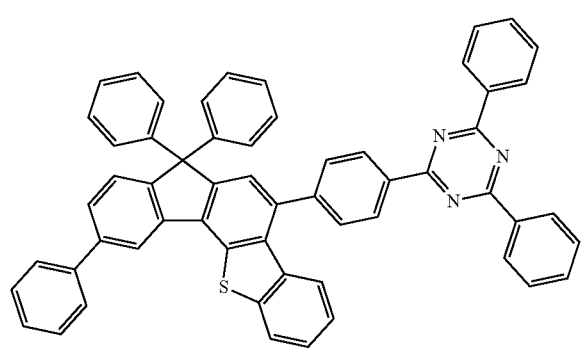
<Chemical Formula 88>
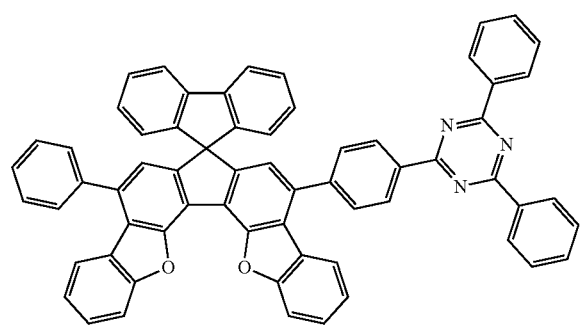
<Chemical Formula 89>
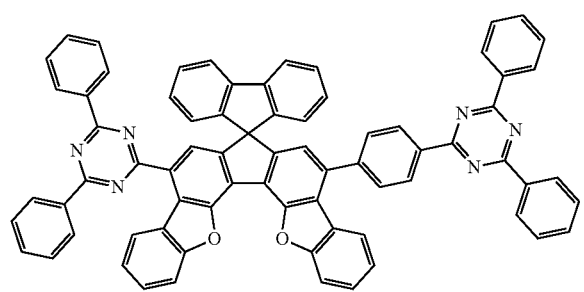
<Chemical Formula 90>
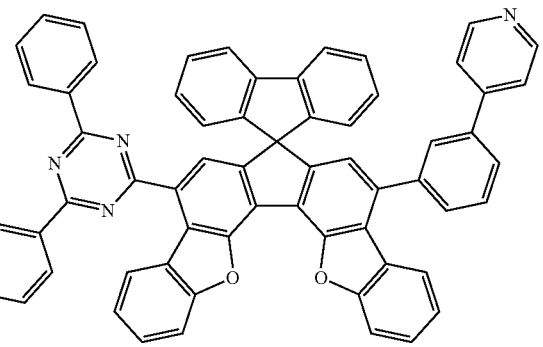
<Chemical Formula 91>
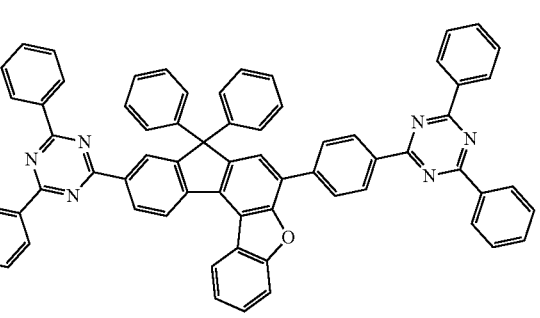
<Chemical Formula 92>
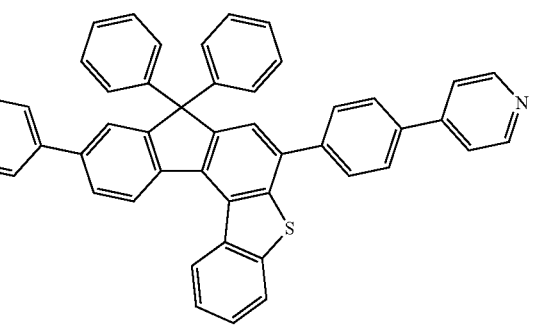
<Chemical Formula 93>
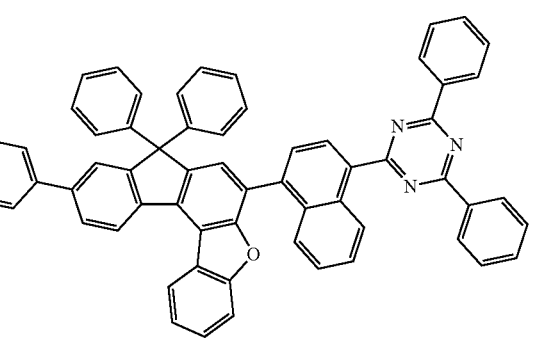

<Chemical Formula 94>

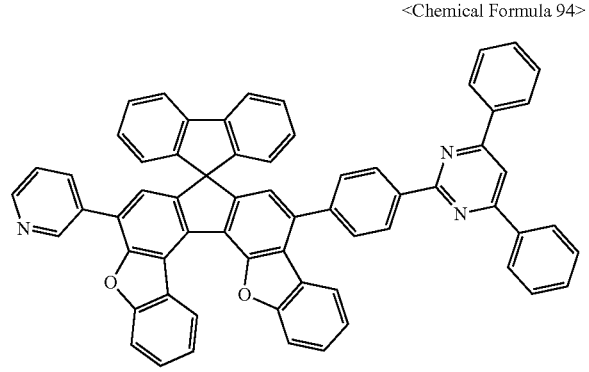

<Chemical Formula 95>

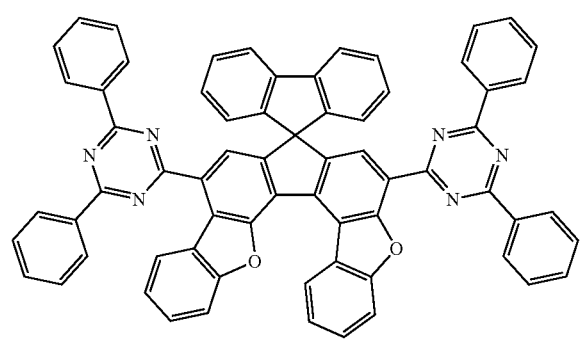

<Chemical Formula 96>

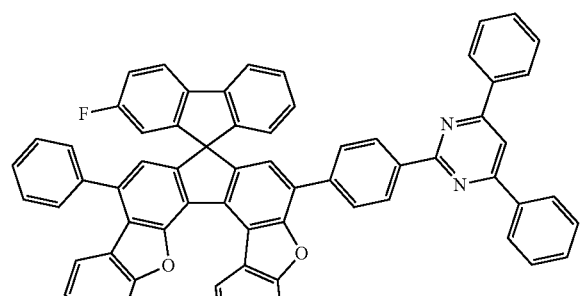

<Chemical Formula 97>

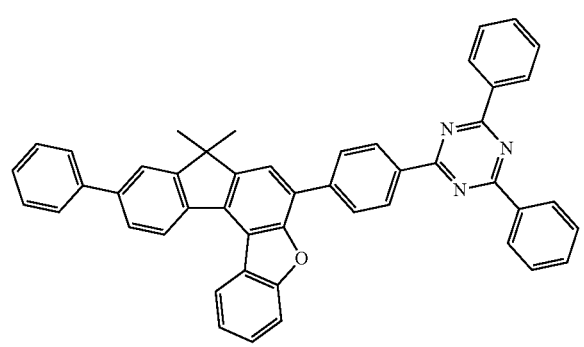

<Chemical Formula 98>

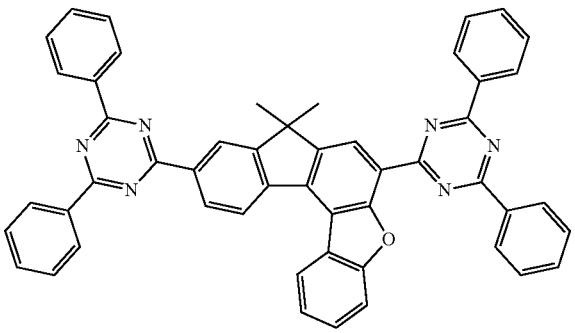

<Chemical Formula 99>

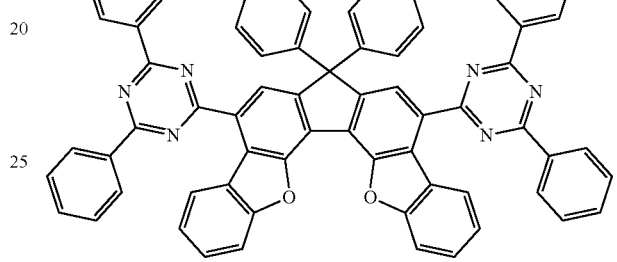

<Chemical Formula 100>

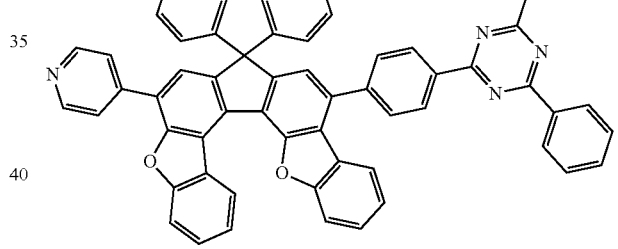

<Chemical Formula 101>

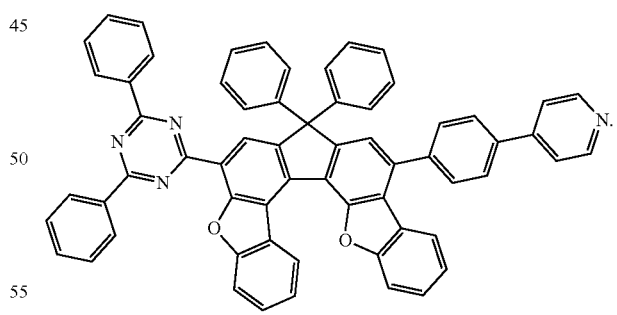

In accordance with another aspect thereof, the present disclosure addresses an organic light-emitting diode, comprising: a first electrode; a second electrode facing the first electrode; and an organic layer interposed between the first electrode and the second electrode, wherein the organic layer includes at least one of the organic compounds according to the present disclosure.

As used herein, the expression "(the organic layer) includes at least one of the organic compounds" is construed to mean that the organic layer may include one or two or more different organic compounds that fall within the scope of the present disclosure.

In this regard, the organic layer including the organic compound of the present disclosure may comprise at least one of a hole injection layer, a hole transport layer, a functional layer capable of both hole injection and hole transport, a light-emitting layer, an electron transport layer, and an electron injection layer.

For use as a material in a hole transport layer, an electron donating molecule having a low ionization potential is used. Predominantly, diamine, triamine or tetraamine derivatives having a triphenylamine skeleton are employed, as exemplified by N,N'-bis(3-methylphenyl)-N,N'-diphenyl-[1,1-biphenyl]-4,4'-diamine (TPD) and N,N'-di(naphthalen-1-yl)-N,N'-diphenylbenzidine (a-NPD).

A hole injection layer (HIL) may be further deposited beneath the hole transport layer. So long as it is typically used in the art, any material can be applied to the HIL without particular limitations imparted thereto. Examples of such typical compounds for use in a hole injection layer include 2-TNATA [4,4',4''-tris(2-naphthylphenyl-phenylamino)-triphenylamine], NPD[N,N'-di(1-naphthyl)-N,N'-diphenylbenzidine)], TPD[N,N'-diphenyl-N,N'-bis(3-methylphenyl)-1,1'-biphenyl-4,4'-diamine], and DNTPD [N,N'-diphenyl-N,N'-bis-[4-(phenyl-m-tolyl-amino)-phenyl]-biphenyl-4,4'-diamine], but are not limited thereto.

According to some particular embodiments of the present disclosure, the organic layer interposed between the first and the second electrode in the organic light-emitting diode may include an electron transport layer and a light-emitting layer. In this regard, the organic compound is used in the electron transport layer and the light-emitting layer may be composed of a host and a dopant.

For this, the host may include the compound represented by the following Chemical Formula 1A:

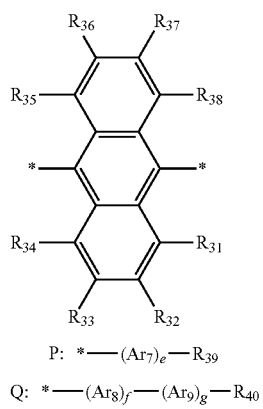

[Chemical Formula 1A]

wherein, $Ar_7$, $Ar_8$ and $Ar_9$, which may be the same or different, are each independently a single bond, a substituted or unsubstituted C5-C60 aromatic linking group, or a substituted or unsubstituted C2-C60 heteroaromatic linking group;

$R_{31}$ to $R_{40}$, which may be the same or different, are each independently selected from among a hydrogen atom, a deuterium atom, a halogen atom, a hydroxyl, a cyano, a nitro, an amino, an amino, an amidino, a hydrazine, a hydrazone, a carboxyl or a salt thereof, a sulfonic acid or a salt thereof, a phosphoric acid or a salt thereof, a substituted or unsubstituted alkyl of 1 to 60 carbon atoms, a substituted or unsubstituted akenyl of 2 to 60 carbon atoms, a substituted or unsubstituted alkynyl of 2 to 60 carbon atoms, a substituted or unsubstituted alkoxy of 1 to 60 carbon atoms, a substituted or unsubstituted alkylthio of 1 to 60 carbon atoms, a substituted or unsubstituted cycloalkyl of 3 to 60 carbon atoms, a substituted or unsubstituted aryl of 6 to 60 carbon atoms, a substituted or unsubstituted aryloxy of 6 to 60 carbon atoms, a substituted or unsubstituted arylthio of 6 to 60 carbon atoms, a substituted or unsubstituted heteroaryl of 2 to 60 carbon atoms, a substituted or unsubstituted (alkyl)amino of 1 to 60 carbon atoms, a di(substituted or unsubstituted alkyl)amino of 1 to 60 carbon atoms, a substituted or unsubstituted arylamino of 6 to 60 carbon atoms, a di(substituted or unsubstituted aryl)amino of 6 to 60 carbon atoms, a substituted or unsubstituted alkylsilyl of 1 to 40 carbon atoms, a substituted or unsubstituted arylsilyl of 6 to 30 carbon atoms, geramanium, phosphorous, and boron, wherein the substitutents may form a fused ring with adjacent groups;

e, f, and g, which may be the same or different, are each independently an integer of 0 to 4;

the two sites represented by * in the compound may be the same or different and each may be independently connected to the P or Q moiety to form an antracene derivative selected from among compounds represented by the following Chemical Formula 1Aa-1 to 1Aa-3:

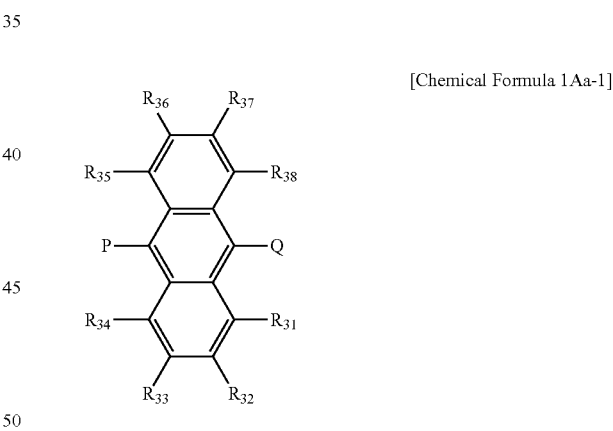

[Chemical Formula 1Aa-1]

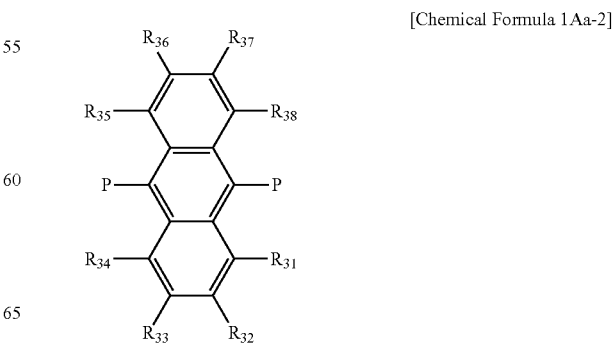

[Chemical Formula 1Aa-2]

[Chemical Formula 1Aa-3]

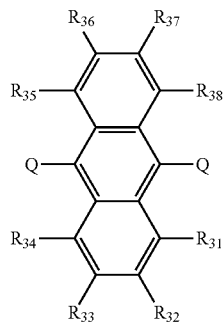

wherein the term 'substituted' in the expression 'substituted or unsubstituted' means having at least one substituent selected from the group consisting of a deuterium, a cyano, a halogen, a hydroxy, a nitro, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, a heteroaryl of 2 to 24 carbon atoms, a heteroarylalkyl of 2 to 24 carbon atoms, an alkoxy of 1 to 24 carbon atoms, an alkylamino of 1 to 24 carbon atoms, an arylamino of 6 to 24 carbon atoms, a heteroarylamino of 1 to 24 carbon atoms, an alkylsilyl of 1 to 24 carbon atoms, an arylsilyl of 6 to 24 carbon atoms, and an aryloxy of 6 to 24 carbon atoms.

In greater detail, the host may be represented by one selected from the group consisting of, but not limited to, the following [Compound 1] to [Compound 47]:

[Compound 1]

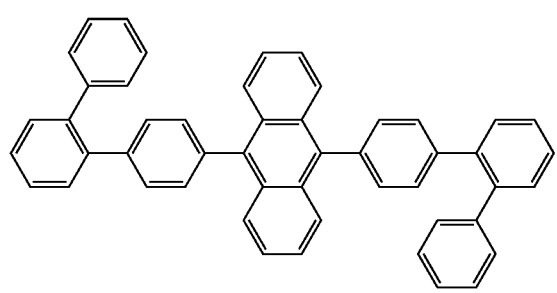

[Compound 2]

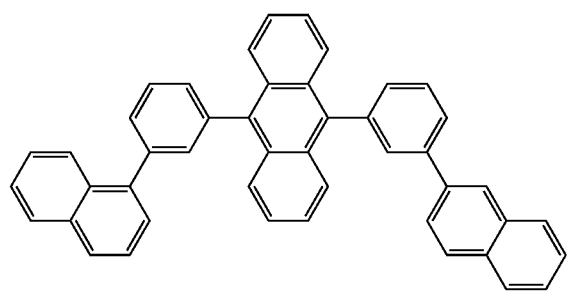

[Compound 3]

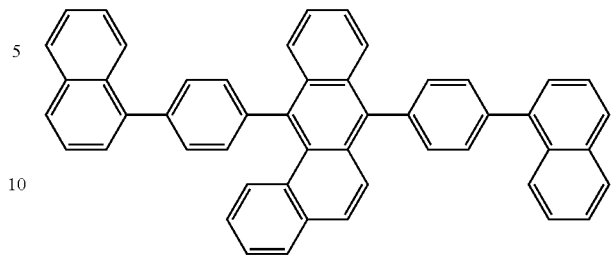

[Compound 4]

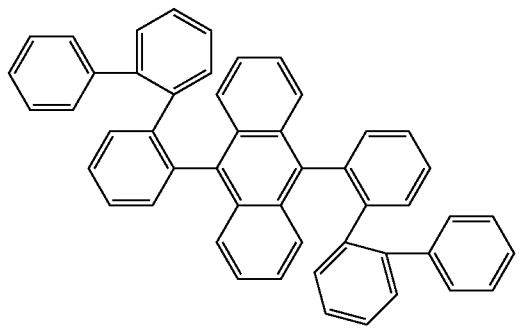

[Compound 5]

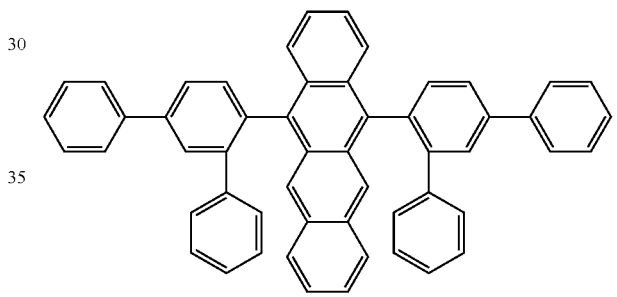

[Compound 6]

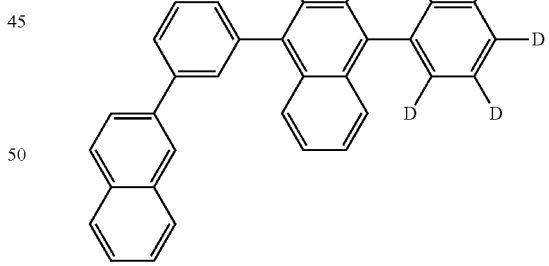

[Compound 7]

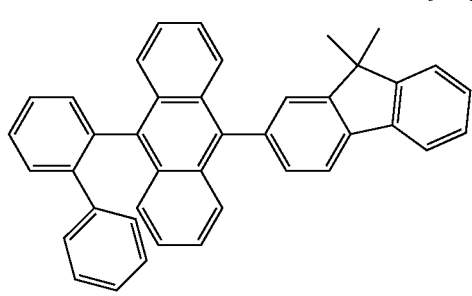

[Compound 8]
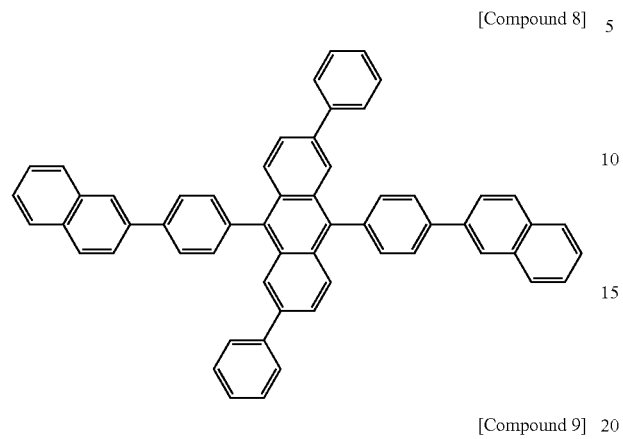
[Compound 12]
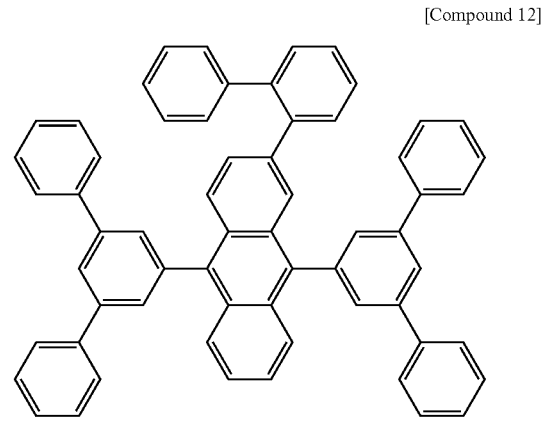
[Compound 9]
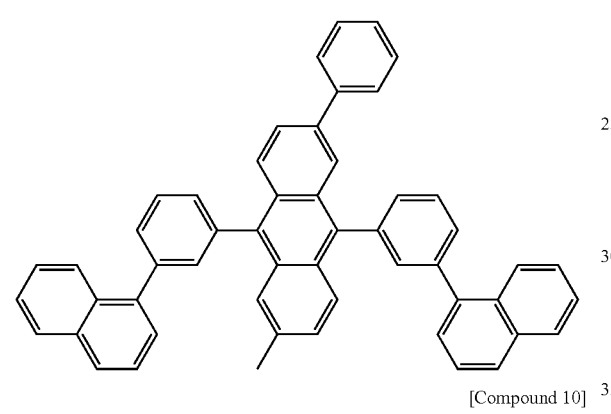
[Compound 13]
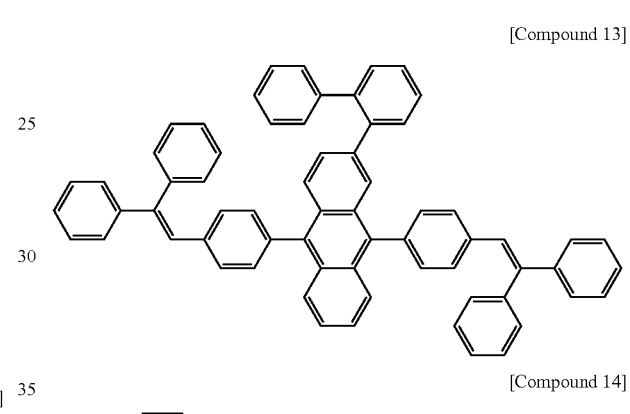
[Compound 10]
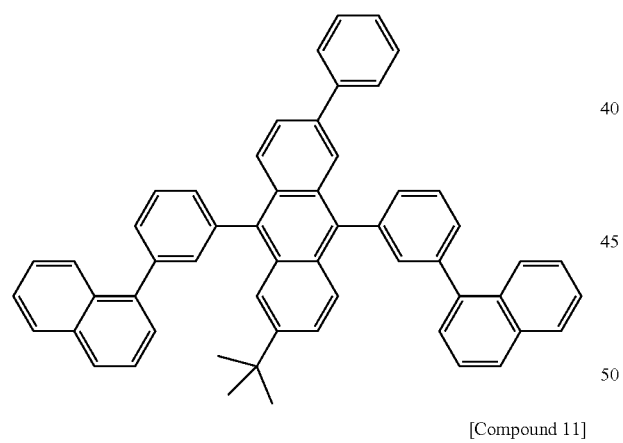
[Compound 14]
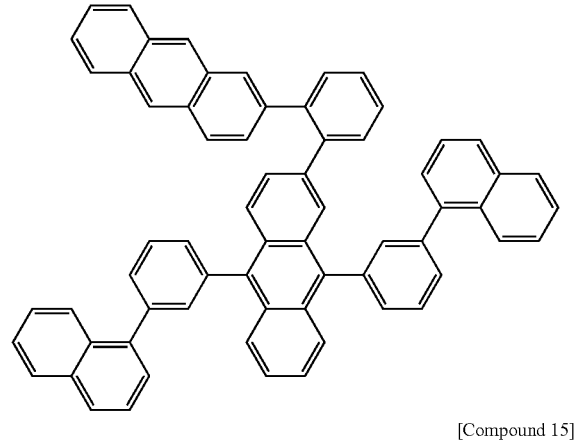
[Compound 11]
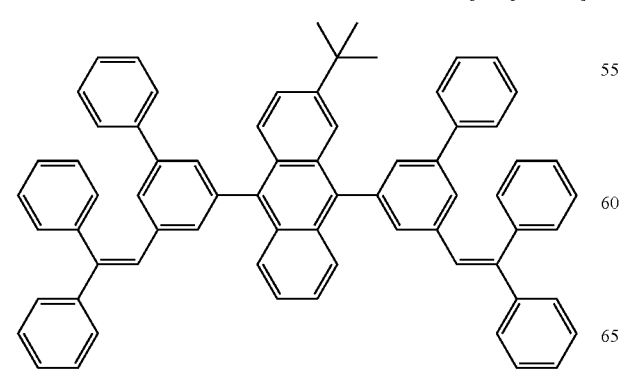
[Compound 15]

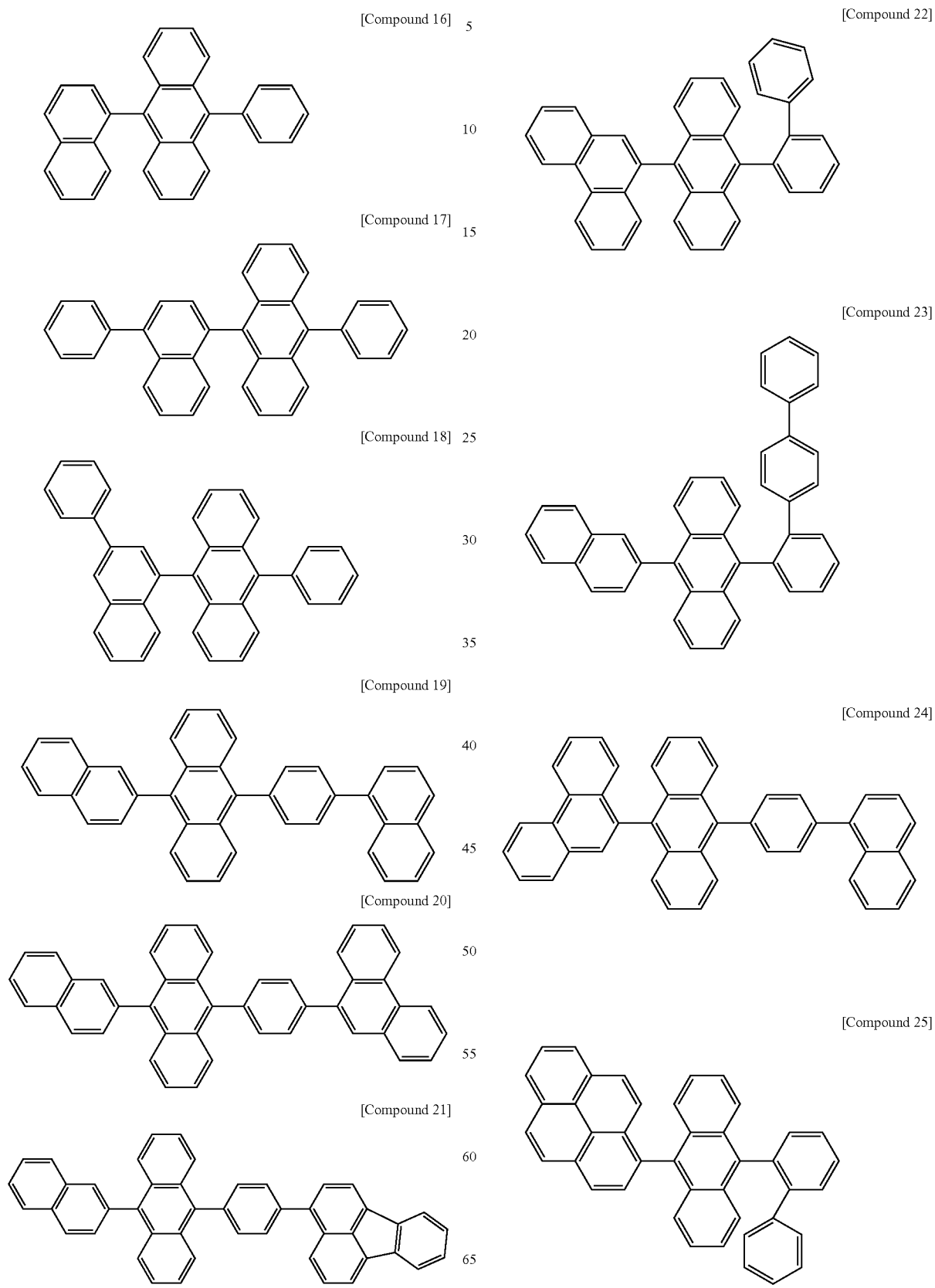

[Compound 26]
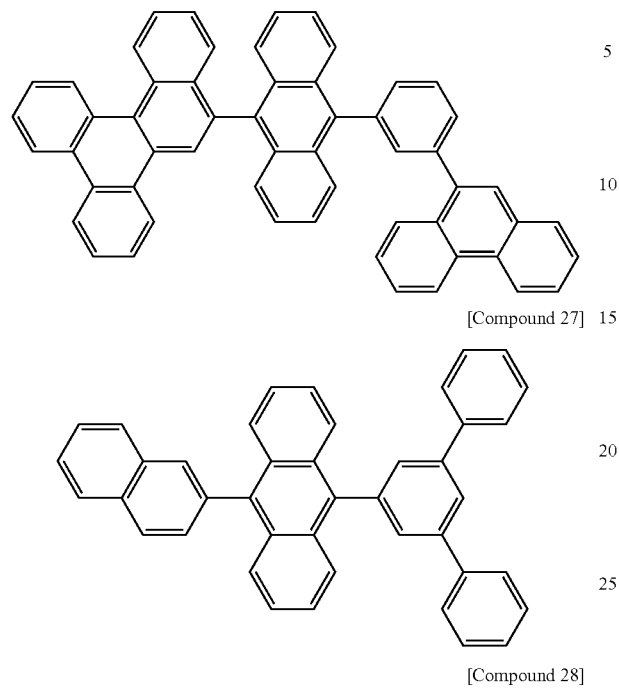
[Compound 27]
[Compound 28]
[Compound 29]
[Compound 30]
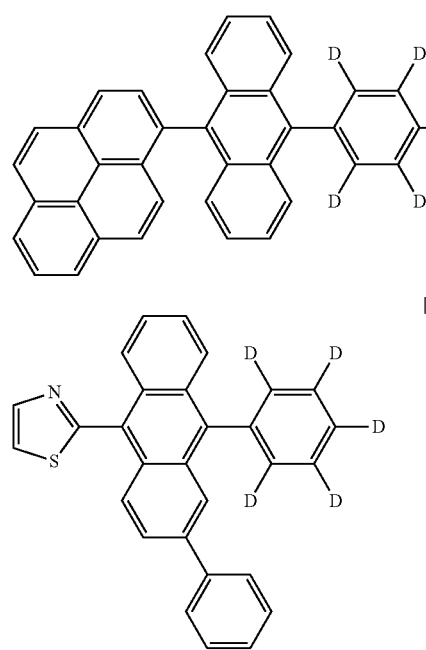
[Compound 31]
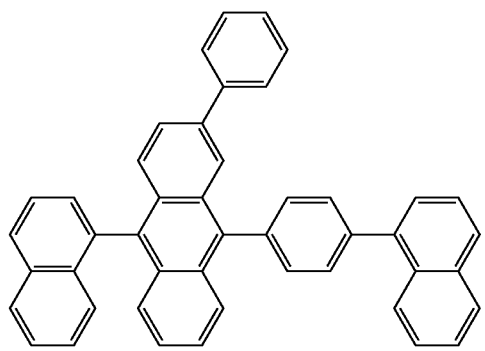
[Compound 32]
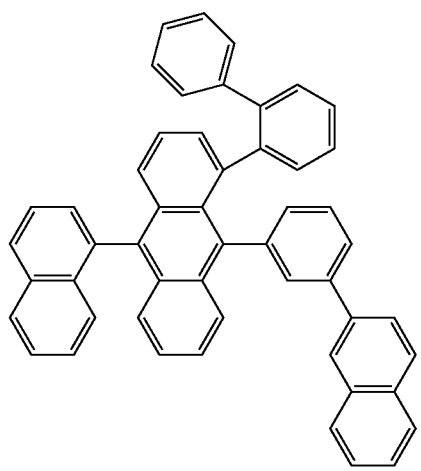
[Compound 33]
[Compound 34]
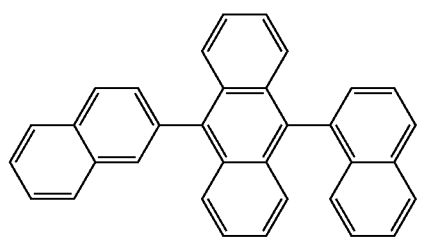

[Compound 35]
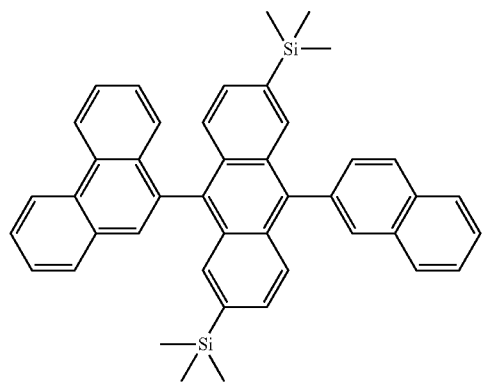
[Compound 36]
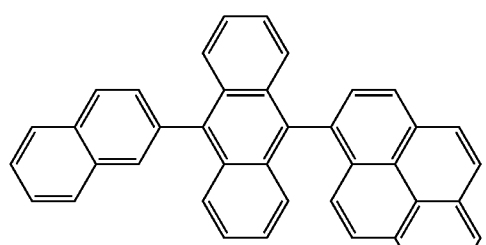
[Compound 37]
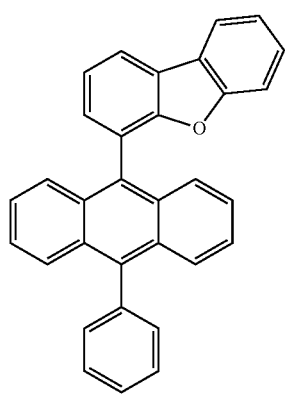
[Compound 38]
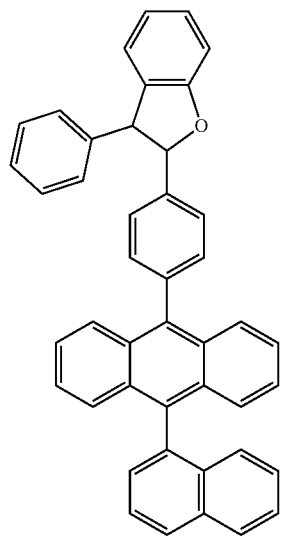
[Compound 39]
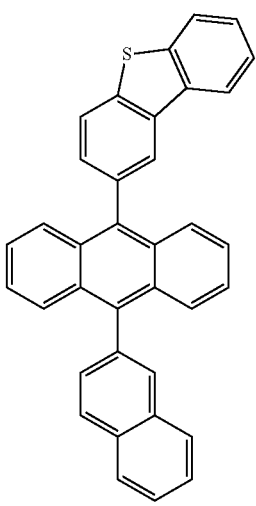
[Compound 40]
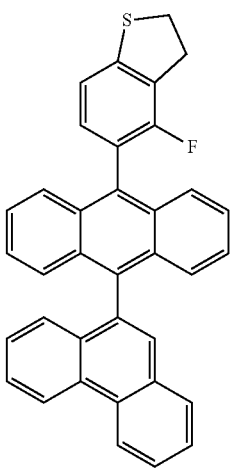
[Compound 41]
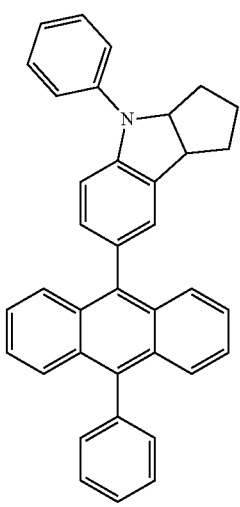

[Compound 42]
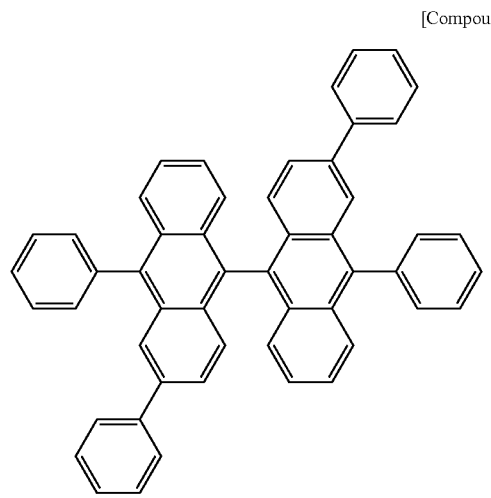

[Compound 46]
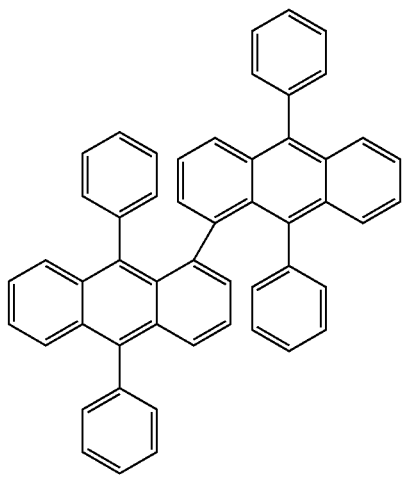

[Compound 43]
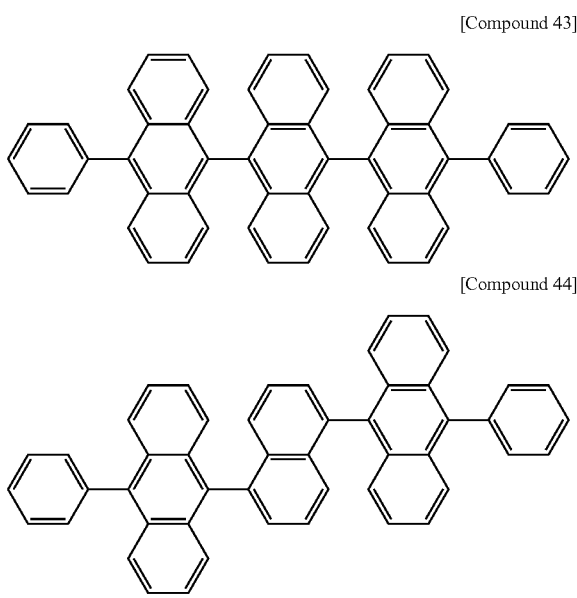

[Compound 47]
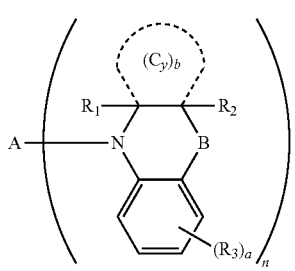

[Compound 44]
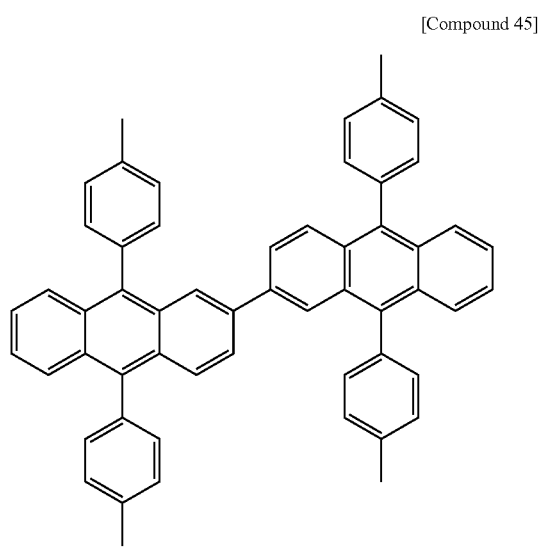

[Compound 45]

In addition, the dopant used in the light-emitting layer in accordance with the present disclosure may be a compound represented by the following Chemical Formula D1 or D2:

[Chemical Formula D1]
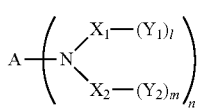

[Chemical Formula D2]

wherein,
A may be any one selected from among a substituted or unsubstituted aryl of 6 to 50 carbon atoms, a substituted or unsubstituted heteroaryl of 3 to 50 carbon atoms bearing O, N, or S as a heteroatom, a substituted or unsubstituted arylene of 6 to 60 carbon atoms, and a substituted or unsubstituted heteroarylene of 3 to 50 carbon atoms bearing O, N, or S as a heteroatom. In some particular embodiments, A may be one selected from among anthracene, pyrene, phenanthrene, indenophenanthrene, chrysene, naphthacene, picene, triphenylene, perylene, and pentacene, In this regard, A may be a compound represented by the following Chemical Formulas A1 to A10:

[Chemical Formula A1]

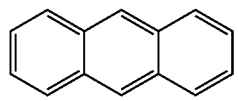

[Chemical Formula A2]

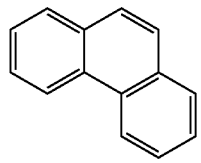

[Chemical Formula A3]

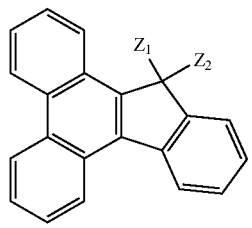

[Chemical Formula A4]

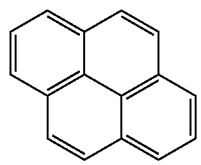

[Chemical Formula A5]

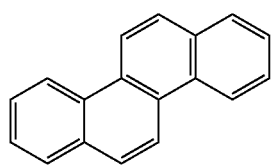

[Chemical Formula A6]

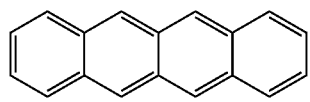

[Chemical Formula A7]

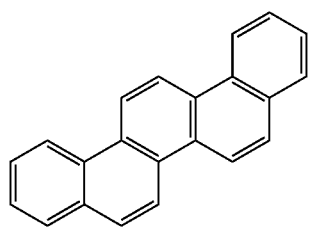

-continued

[Chemical Formula A8]

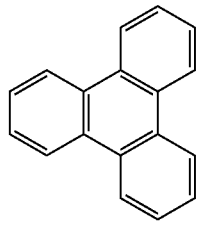

[Chemical Formula A9]

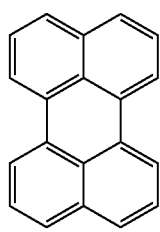

[Chemical Formula A10]

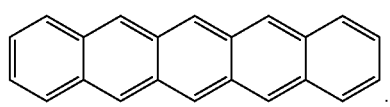

In Chemical Formula A3, $Z_1$ and $Z_2$ may be the same or different and are each independently selected from the group consisting of a hydrogen atom, a deuterium atom, a substituted or unsubstituted alkyl of 1 to 60 carbon atoms, a substituted or unsubstituted alkenyl of 2 to 60 carbon atoms, a substituted or unsubstituted alkynyl of 2 to 60 carbon atoms, a substituted or unsubstituted alkoxy of 1 to 60 carbon atoms, a substituted or unsubstituted alkylthio of 1 to 60 carbon atoms, a substituted or unsubstituted cycloalkyl of 3 to 60 carbon atoms, a substituted or unsubstituted aryl of 6 to 60 carbon atoms, a substituted or unsubstituted aryloxy of 6 to 60 carbon atoms, a substituted or unsubstituted arylthio of 6 to 60 carbon atoms, a substituted or unsubstituted heteroaryl of 2 to 60 carbon atoms, a substituted or unsubstituted (alkyl)amino of 1 to 60 carbon atoms, a di(substituted or unsubstituted alkyl)amino of 1 to 60 carbon atoms or a (substituted or unsubstituted aryl)amino of 6 to 60 carbon atoms, and a di(substituted or unsubstituted aryl)amino of 6 to 60 carbon atoms, with the proviso that $Z_1$ and $Z_2$ may each form a fused ring with an adjacent radical.

In Chemical Formula D1, $X_1$ and $X_2$ may each be independently a substituted or unsubstituted arylene of 6 to 30 carbon atoms or a single bond, with the proviso that $X_1$ and $X_2$ may bond to each other, $Y_1$ and $Y_2$ may be the same or different and are each independently selected from the group consisting of a substituted or unsubstituted aryl of 6 to 24 carbon atoms, a substituted or unsubstituted heteroaryl of 2 to 24 carbon atoms, a substituted or unsubstituted alkyl of 1 to 24 carbon atoms, a substituted or unsubstituted heteroalkyl of 1 to 24 carbon atoms, a substituted or unsubstituted cycloalkyl of 3 to 24 carbon atoms, a substituted or unsubstituted alkoxy of 1 to 24 carbon atoms, a cyano, a halogen, a substituted or unsubstituted aryloxy of 6 to 24 carbon atoms, a substituted or unsubstituted alkylsilyl of 1 to 40 carbon atoms, a substituted or unsubstituted arylsilyl of 6 to 30 carbon atoms, a germanium, a phosphorus, a boron, a deuterium, and a hydrogen, with the proviso that $Y_1$ and $Y_2$ may each form with an aliphatic, aromatic, heteroaliphatic, or heteroaromatic fused ring with an adjacent radical, l and m are each an integer of 1 to 20, and n is an integer of 1 to 4.

In Chemical Formula D2, $C_y$ is a substituted or unsubstituted cycloalkyl of 3 to 8 carbon atoms and b is an integer of 1 to 4, with the proviso that when b is an integer of 2 or greater, the corresponding cycloalkanes may be the same or different and may each be in a fused form having a deuterium or an alkyl as a substituent;

B is a single bond or —[C($R_5$)($R_6$)]$_p$— wherein p is an integer of 1 to 3, with the proviso that when p is 2 or greater, the corresponding two or more $R_5$'s are the same or different and the corresponding two or more $R_6$'s are the same or different;

$R_1$, $R_2$, $R_3$, $R_4$, and $R_6$ may each be independently selected from among a hydrogen atom, a deuterium atom, a halogen atom, a hydroxyl, a cyano, a nitro, an amino, an amidino, a hydrazine, a hydrazone, a carboxyl or a salt thereof, a sulfonic acid or a salt thereof, a phosphoric acid or a salt thereof, a substituted or unsubstituted alkyl of 1 to 60 carbon atoms, a substituted or unsubstituted alkenyl of 2 to 60 carbon atoms, a substituted or unsubstituted alkynyl of 2 to 60 carbon atoms, a substituted or unsubstituted alkoxy of 1 to 60 carbon atoms, a substituted or unsubstituted alkylthio of 1 to 60 carbon atoms, a substituted or unsubstituted cycloalkyl of 3 to 60 carbon atoms, a substituted or unsubstituted aryl of 6 to 60 carbon atoms, a substituted or unsubstituted aryloxy of 6 to 60 carbon atoms, a substituted or unsubstituted arylthio of 6 to 60 carbon atoms, a substituted or unsubstituted heteroaryl of 2 to 60 carbon atoms, a substituted or unsubstituted alkylamino of 1 to 60 carbon atoms, a di(substituted or unsubstituted alkyl)amino of 1 to 60 carbon atoms or a (substituted or unsubstituted aryl)amino of 6 to 60 carbon atoms, a di(substituted or unsubstituted aryl)amino of 6 to 60 carbon atoms, a substituted or unsubstituted alkylsilyl of 1 to 40 carbon atoms, and a substituted or unsubstituted arylsilyl of 6 to 30 carbon atoms;

a is an integer of 1 to 4, with the proviso that when a is 2 or greater, the corresponding plural $R_3$'s may be the same or different and may each be in a fused form, and n is an integer of 1 to 4.

The amine radical of Chemical Formulas D1 and D2, which is linked to A, may be represented by any one selected from among, but not limited to, the following Substituents 1 to 52:

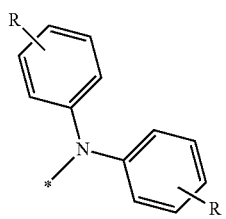

[Substituent1]

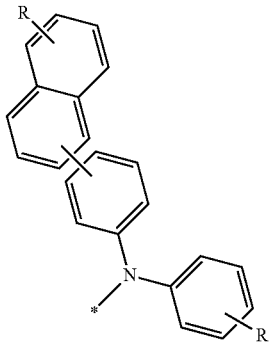

[Substituent2]

[Substituent3]

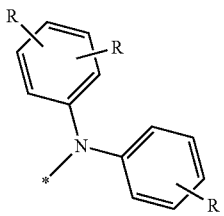

[Substituent4]

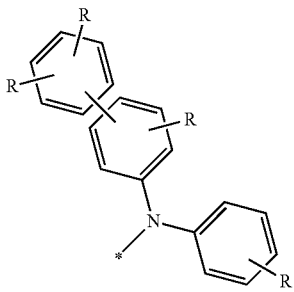

[Substituent5]

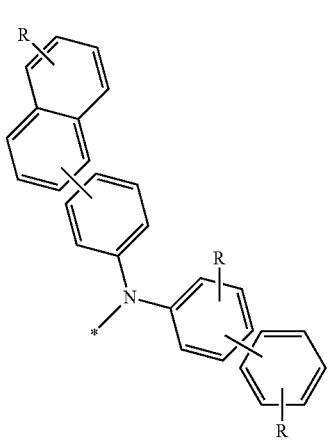

[Substituent6]

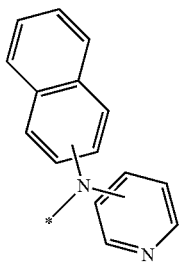

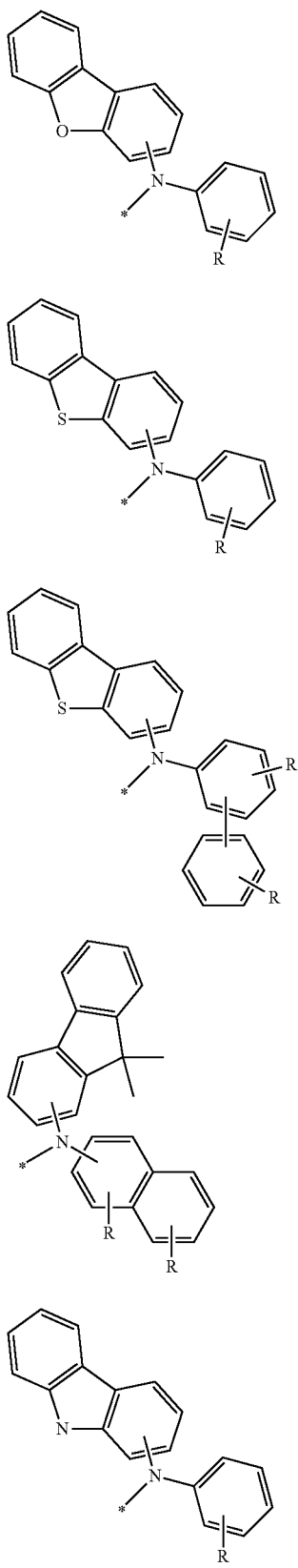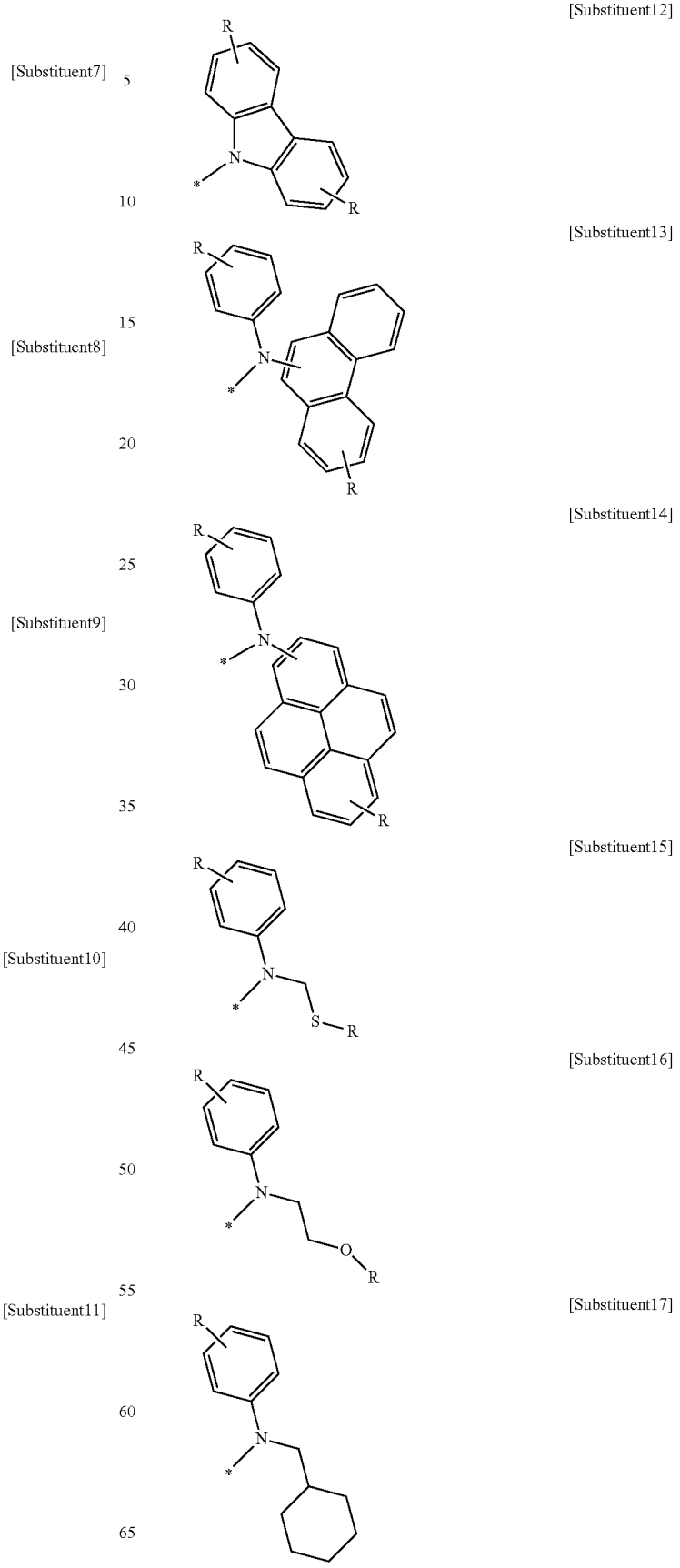

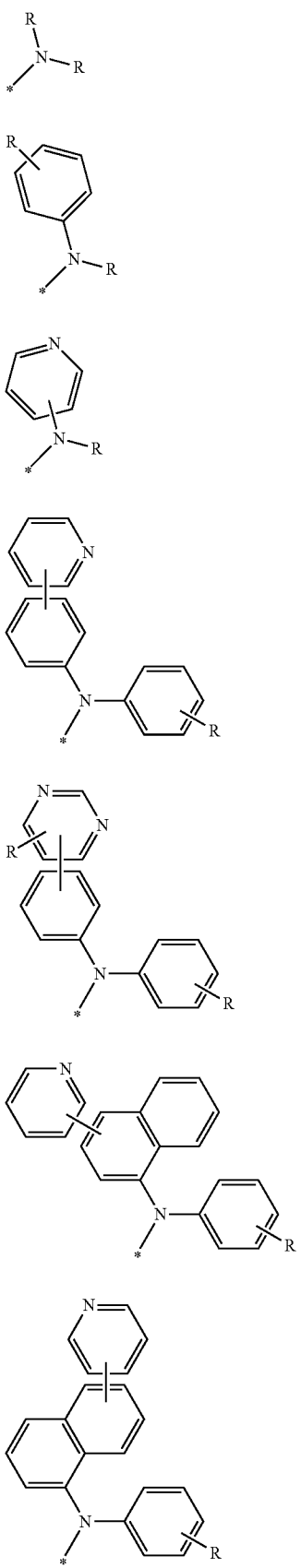
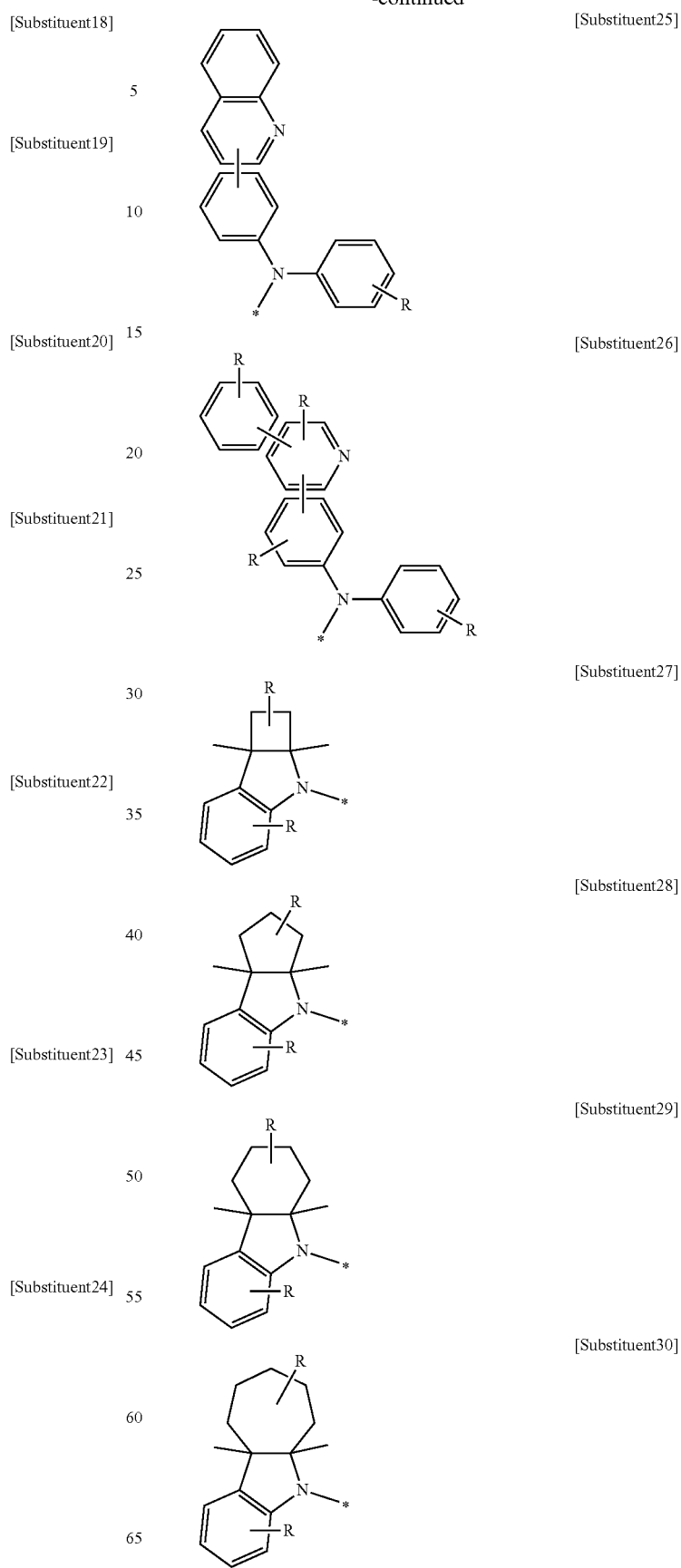

63
-continued
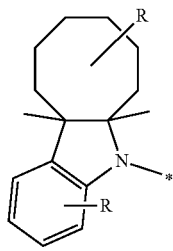
[Substituent31]
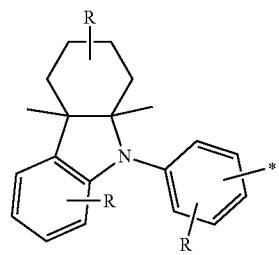
[Substituent37]
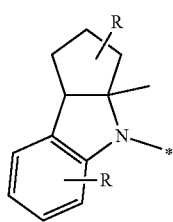
[Substituent32]
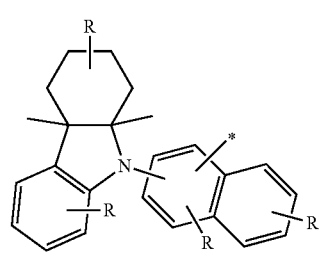
[Substituent38]
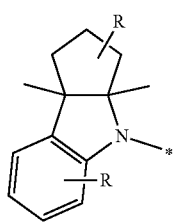
[Substituent33]
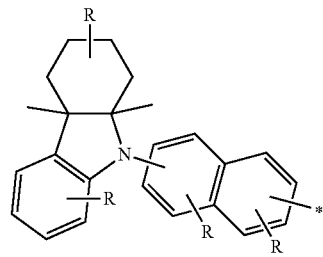
[Substituent39]
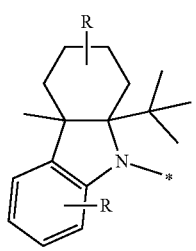
[Substituent34]
[Substituent35]
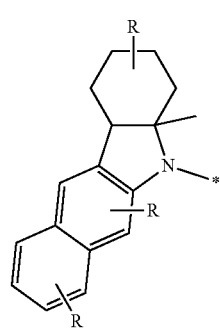
[Substituent40]
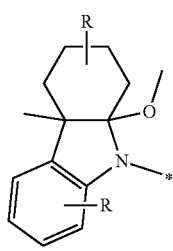
[Substituent36]
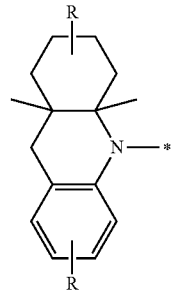
[Substituent41]
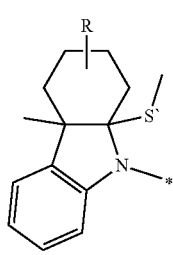
64
-continued

[Substituent42]
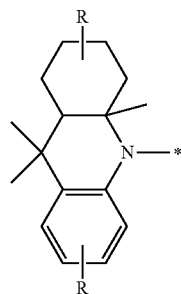
[Substituent43]
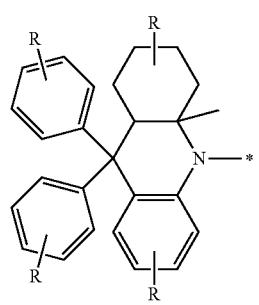
[Substituent44]
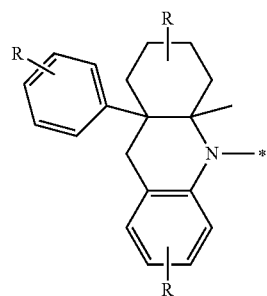
[Substituent45]
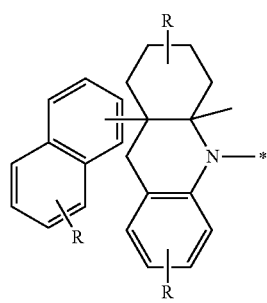
[Substituent46]
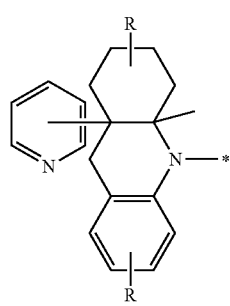
[Substituent47]
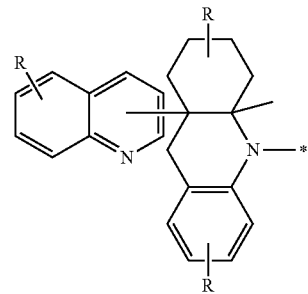
[Substituent48]
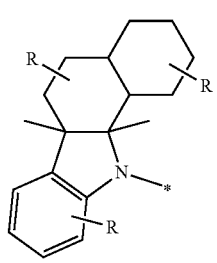
[Substituent49]
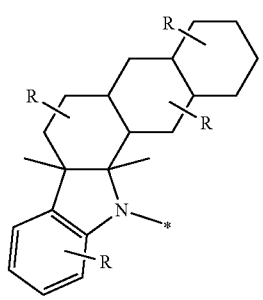
[Substituent50]
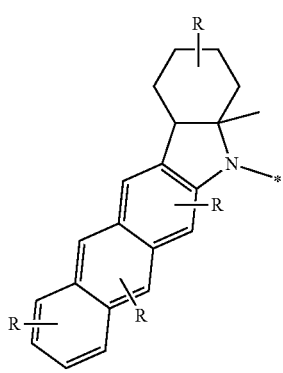
[Substituent51]
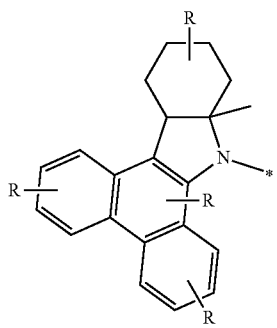

-continued

[Substituent52]

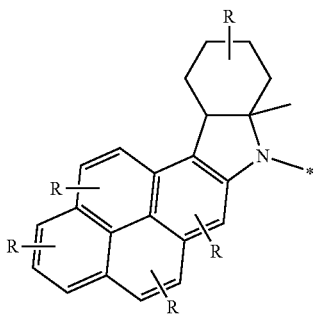

wherein R's, which may be the same or different, are each independently selected from among a hydrogen atom, a deuterium atom, a halogen atom, a hydroxyl, a cyano, a nitro, an amino, an amidino, a hydrazine, a hydrazone, a carboxyl or a salt thereof, a sulfonic acid or a salt thereof, a phosphoric acid or a salt thereof, a substituted or unsubstituted alkyl of 1 to 60 carbon atoms, a substituted or unsubstituted alkenyl of 2 to 60 carbon atoms, a substituted or unsubstituted alkynyl of 2 to 60 carbon atoms, a substituted or unsubstituted alkoxy of 1 to 60 carbon atoms, a substituted or unsubstituted alkylthio of 1 to 60 carbon atoms, a substituted or unsubstituted cycloalkyl of 3 to 60 carbon atoms, a substituted or unsubstituted aryl of 6 to 60 carbon atoms, a substituted or unsubstituted aryloxy of 6 to 60 carbon atoms, a substituted or unsubstituted arylthio of 6 to 60 carbon atoms, a substituted or unsubstituted heteroaryl of 2 to 60 carbon atoms, a substituted or unsubstituted (alkyl)amino of to 60 carbon atoms, a di(substituted or unsubstituted alkyl)amino of 1 to 60 carbon atoms or a (substituted or unsubstituted aryl)amino of 6 to 60 carbon atoms, a di(substituted or unsubstituted aryl)amino of 6 to 60 carbon atoms, a substituted or unsubstituted alkylsilyl of 1 to 40 carbon atoms, a substituted or unsubstituted arylsilyl of 6 to 30 carbon atoms, a germanium, a phosphorus, and a boron, may each have 1 to 12 substituents, and may each form a fused ring with an adjacent radical.

The light-emitting layer may contain various host and dopant materials in addition to the aforementioned dopant and host materials.

When the light-emitting layer contains a host and a dopant, the content of the dopant in the light-emitting layer may range from about 0.01 to 20 parts by weight, based on 100 parts by weight of the host, but is not limited thereto.

According to some particular embodiments of the present disclosure, the light-emitting layer has a thickness of 50 to 2,000 Å.

In addition, the organic metal compound represented by Chemical Formula F may be used, either alone or in combination with the aforementioned material, as a compound for an electron transport layer in the present disclosure:

$Y_m$-M-(OA)$_n$ [Chemical Formula F]

wherein,

Y is a ligand that contains two moieties respectively responsible for forming a single bond through a direct bond to M and for forming a coordinate bond with M, each moiety being selected from among C, N, O and S, and which is chelated by the single bond and the coordinate bond; M is an alkali metal, an alkaline earth metal, an aluminum (Al) atom, or a boron (B) atom, with the proviso that:

when M is an alkali metal, m=1 and n=0;

when M is an alkaline earth metal, m=1 and n=1, or m=2 and n=0; or when M is aluminum or a boron, m is an integer of 1 to 3 and n is an integer of 0 to 2, satisfying the relationship m+n=3; and OA is a monodentate ligand capable of forming a single bond or a coordinate bond with M, wherein O is oxygen, and A is selected from among a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, and a substituted or unsubstituted heteroaryl of 2 to 50 carbon atoms bearing O, N, or S as a heteroatom.

In the present disclosure, Y's may be the same or different and may each be one selected from among, but not limited to, the following [Structural Formula C1] to [Structural Formula C39]:

[Structural FormulaC1]

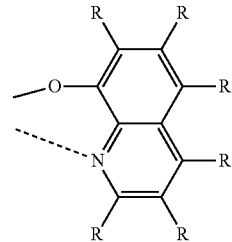

[Structural FormulaC2]

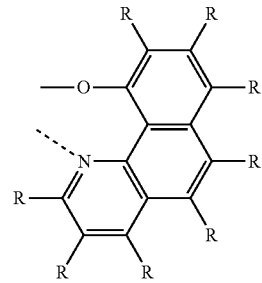

[Structural FormulaC3]

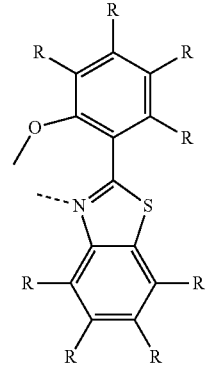

[Structural FormulaC4]
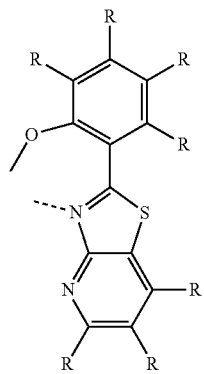
[Structural FormulaC5]
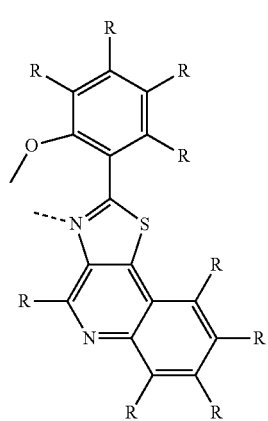
[Structural FormulaC6]
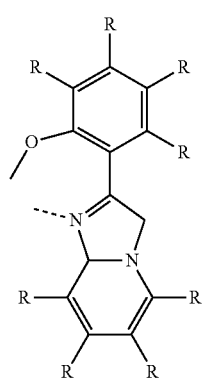
[Structural FormulaC7]
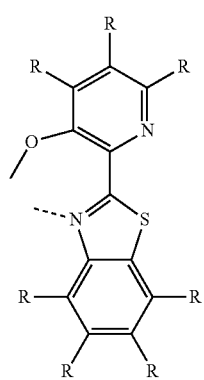
[Structural FormulaC8]
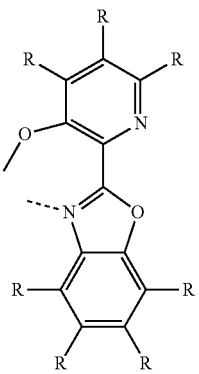
[Structural FormulaC9]
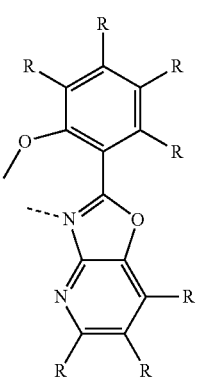
[Structural FormulaC10]
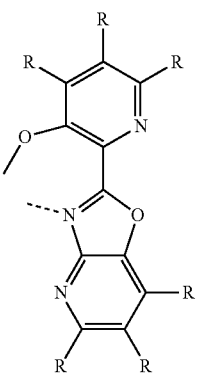
[Structural FormulaC11]
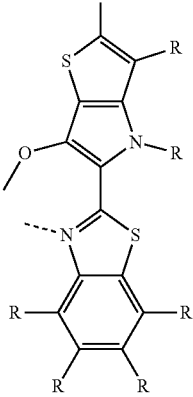

[Structural FormulaC12]
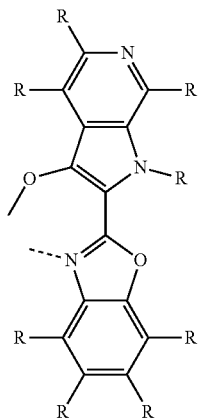
[Structural FormulaC13]
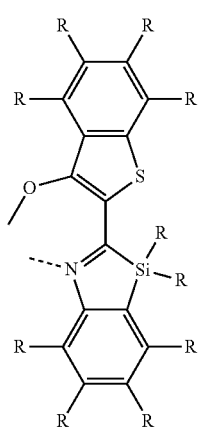
[Structural FormulaC14]
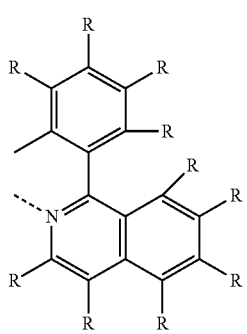
[Structural FormulaC15]
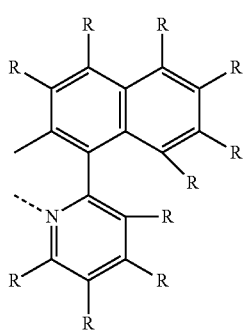
[Structural FormulaC16]
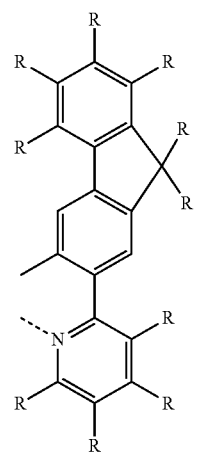
[Structural FormulaC17]
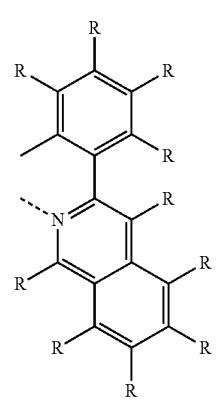
[Structural FormulaC18]
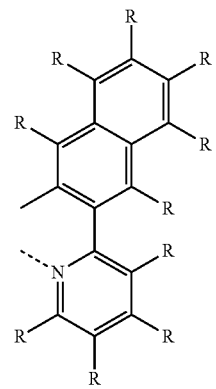
[Structural FormulaC19]
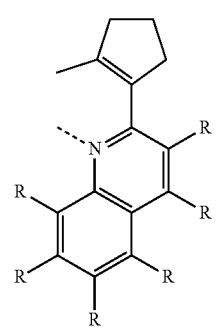

[Structural FormulaC20]
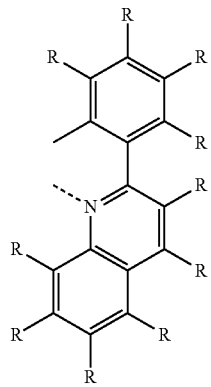
[Structural FormulaC21]
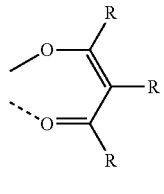
[Structural FormulaC22]
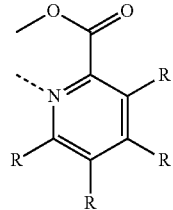
[Structural FormulaC23]
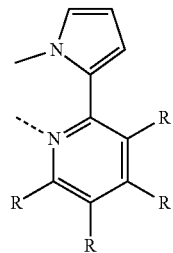
[Structural FormulaC24]
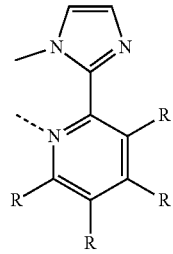
[Structural FormulaC25]
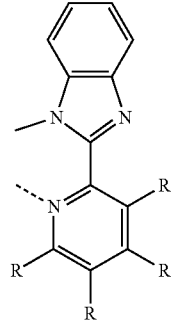
[Structural FormulaC26]
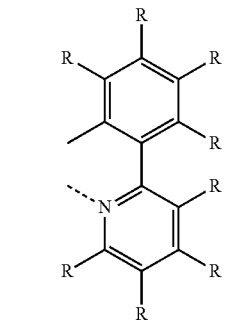
[Structural FormulaC27]
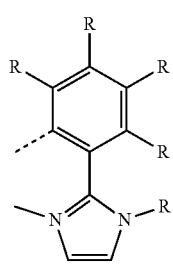
[Structural FormulaC28]
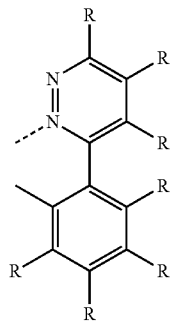
[Structural FormulaC29]
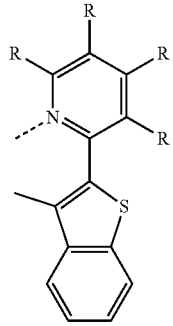
[Structural FormulaC30]
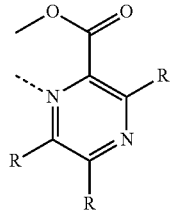

[Structural FormulaC31]

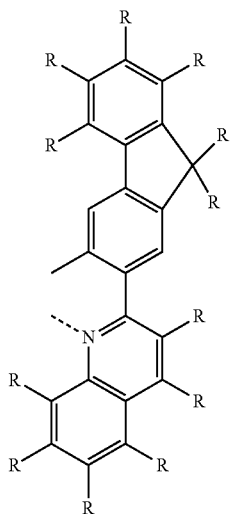

[Structural FormulaC32]

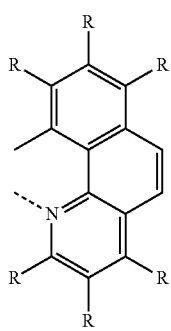

[Structural FormulaC33]

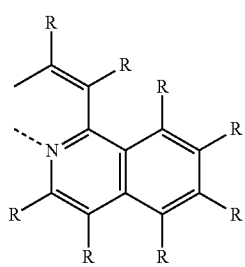

[Structural FormulaC34]

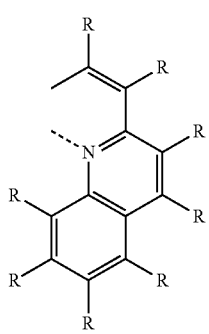

[Structural FormulaC35]

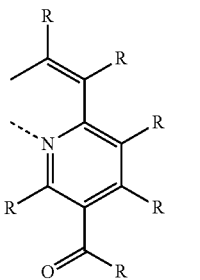

[Structural FormulaC36]

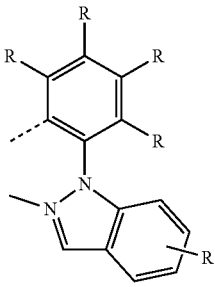

[Structural FormulaC37]

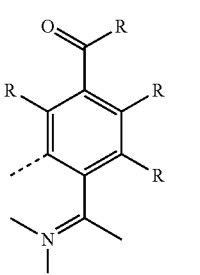

[Structural FormulaC38]

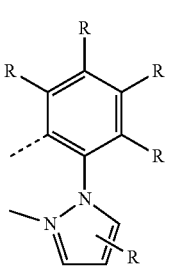

[Structural FormulaC39]

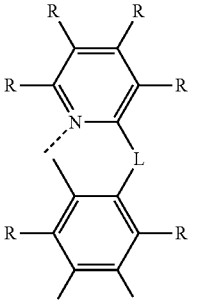

wherein,

R's, which may be the same or different, are each independently selected from among a hydrogen atom, a deuterium atom, a halogen, a cyano, a substituted or unsubstituted alkyl of 1 to 30 carbon atoms, a substituted or unsubstituted aryl of 6 to 30 carbon atoms, a substituted or unsubstituted heteroaryl of 3 to 30 carbon atoms, a substituted or unsubstituted alkoxy of 1 to 30 carbon atoms, a substituted or unsubunsubstituted cycloalkyl of 3 to 30 carbon atoms, a substituted or unsubstituted alkenyl of 2 to 30 carbon atoms, a substituted or unsubstituted alkylamino of 1 to 30 carbon atoms, a substituted or unsubstituted alkylsilyl of 1 to 30 carbon atoms, a substituted or unsubstituted arylamino of 6 to 30 carbon atoms, and a substituted or unsubstituted arylsilyl of 6 to 30 carbon atoms, and may form a spiro or fused ring with an adjacent substituent via an alkylene or alkenylene linker. Here, the term "substituted" in the expression "substituted or unsubstituted" means having at least one substituent selected from the group consisting of a deuterium atom, a cyano, a halogen, a hydroxy, a nitro, an alkyl, an alkoxy, an alkylamino, an arylamino, a heteroarylamino, an alkylsilyl, an arylsilyl, an aryloxy, an aryl, a heteroaryl, a germanium, a phosphorus, and a boron.

An electron injection layer (EIL) that functions to facilitate electron injection from the cathode, thus improving the power efficiency of the diode, may be further deposited on the electron transport layer. So long as it is conventionally used in the art, any material can be available for the electron injection layer without particular limitations. Examples include LiF, NaCl, CsF, $Li_2O$, and BaO.

A material for the electron injection layer may be any well-known material, as exemplified by CsF, NaF, LiF, NaCl, Li2O, BaO, etc. Deposition conditions for the electron injection layer may vary, depending on compounds used, but may be generally selected from condition scopes that are almost the same as for the formation of hole injection layers.

The electron injection layer may range in thickness from about 1 Å to about 100 Å, and particularly from about 3 Å to about 90 Å. Given the thickness range for the electron injection layer, the diode can exhibit satisfactory electron injection properties without actually elevating a driving voltage.

Here, the cathode may be made of lithium (Li), magnesium (Mg), aluminum (Al), aluminum-lithium (Al—Li), calcium (Ca), magnesium-indium (Mg—In), or magnesium-silver (Mg—Ag). For a top-emitting OLED, a transparent cathode made of ITO or IZO may be employed.

In another embodiment, the light-emitting device of the present disclosure may further comprise a light-emitting layer, made of a blue light-emitting material, a green light-emitting material, or a red light-emitting material, which can emit light in a wavelength range of 380 nm to 800 nm. That is, the light-emitting layer in the organic light-emitting device of the present disclosure may have a multilayer structure in which the additional blue, green, and/or red light-emitting layer may be made of a fluorescent or phosphorescent material.

Further, one or more layers selected from among a hole injection layer, a hole transport layer, a functional layer capable of both hole injection and hole transport, a light-emitting layer, an electron transport layer, and an electron injection layer may be deposited using a deposition process or a solution process.

Here, the deposition process is a process by which a material is vaporized and deposited in a vacuum or at a low pressure to form a layer, and the solution process is a method in which a material is dissolved in a solvent and applied for the formation of a thin film by means of inkjet printing, roll-to-roll coating, screen printing, spray coating, dip coating, spin coating, etc.

Also, the organic light-emitting diode of the present disclosure may be applied to a device selected from among flat display devices, flexible display devices, monochrome or grayscale flat illumination devices, and monochrome or grayscale flexible illumination devices.

Below, the organic light-emitting diode of the present disclosure is explained with reference to FIG. 1.

FIG. 1 is a schematic cross-sectional view of the structure of an organic light-emitting diode according to some embodiments of the present disclosure. The organic light-emitting diode includes an anode 20, a hole transport layer 40, an organic light-emitting layer 50, an electron transport layer 60, and a cathode 80, and optionally a hole injection layer 30 or an electron injection layer 70. In addition, one or two intermediate layers may be further formed in the organic light-emitting diode. A hole barrier layer or an electron barrier layer may be also further established.

Reference is made to FIG. 1 with regard to the organic light-emitting diode of the present disclosure and the fabrication thereof. First, a substrate 10 is coated with an anode electrode material to form an anode 20. So long as it is used in a typical organic EL device, any substrate may be used as the substrate 10. Preferable is an organic substrate or transparent plastic substrate that exhibits excellent transparency, surface smoothness, ease of handling, and waterproofness. As the anode electrode material, indium tin oxide (ITO), indium zinc oxide (IZO), tin oxide ($SnO_2$), or zinc oxide (ZnO), which are transparent and superior in terms of conductivity, may be used.

A hole injection layer material is applied on the anode electrode 20 by thermal deposition in a vacuum or by spin coating to form a hole injection layer 30. Subsequently, using thermal deposition in a vacuum or spin coating, a hole transport layer material is applied to the hole injection layer 30 to form a hole transport layer 40.

Then, an organic light-emitting layer 50 is deposited on the hole transport layer 40, optionally followed by the formation of a hole barrier layer (not shown) on the organic light-emitting layer 50 by deposition in a vacuum or by spin coating. When holes traverse the organic light-emitting layer and are introduced into the cathode, the efficiency and lifespan of the diode are deteriorated. Formed of a material with a low HOMO (Highest Occupied Molecular Orbital) level, the hole barrier layer serves to prevent the introduction of holes into the cathode. Any material that has a higher ionization potential than the light-emitting compound and which is also able to carry electrons may be used for the hole barrier layer without limitation. Representative among hole barrier materials are BAlq, BCP, and TPBI.

Using a vacuum deposition method or a spin-coating method, an electron transport layer 60 may be deposited on the hole barrier layer and may then be overlaid with an electron injection layer 70. A cathode metal is deposited on the electron injection layer 70 by thermal deposition in a vacuum to form a cathode 80, thus obtaining an organic EL diode. Here, the cathode may be made of lithium (Li), magnesium (Mg), aluminum (Al), aluminum-lithium (Al—Li), calcium (Ca), magnesium-indium (Mg—In), or magnesium-silver (Mg—Ag). For a top-emitting OLED, a transparent cathode made of ITO or IZO may be employed.

A better understanding of the light-emitting diode according to the present disclosure may be obtained through the following examples which are set forth to illustrate, but are not to be construed as limiting the present disclosure.

EXAMPLES

Synthesis Example 1: Synthesis of Compound of Chemical Formula 1

Synthesis Example 1-(1): Synthesis of Intermediate 1-a

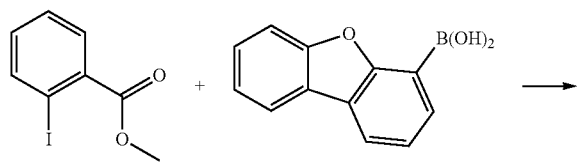

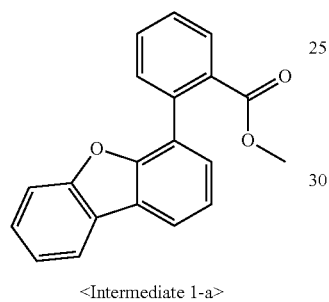

<Intermediate 1-a>

In a 500-mL round-bottom flask reactor, methyl 5-iodo-2-iodobenzoate (19.1 g, 73 mmol), 4-dibenzofuran boronic acid (18.7 g, 88 mmol), tetrakis (triphenylphosphine)palladium (1.7 g, 0.15 mmol), and potassium carbonate (20.2 g, 146.7 mmol) stirred together with toluene (125 mL), tetrahydrofuran (125 mL), and water (50 mL) for 10 hrs at 80° C. After completion of the reaction, the reaction mixture was cooled to room temperature and extracted with ethyl acetate. The organic layer thus formed was separated, concentrated in a vacuum, and purified by column chromatography to afford <Intermediate 1-a>. (9.5 g, 43%).

Synthesis Example 1-(2): Synthesis of Intermediate 1-b

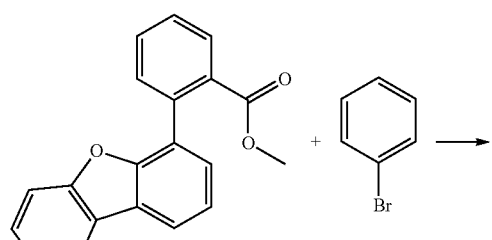

<Intermediate 1-a>

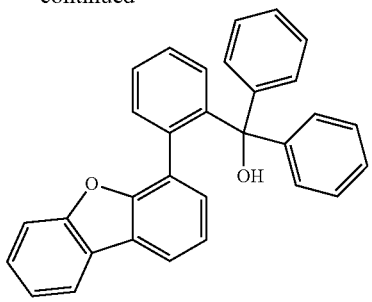

<Intermediate 1-b>

In a 2-L round-bottom flask reactor, bromobenzene (13.2 g, 83.97 mmol), tetrahydrofuran (250 ml) was stirred at a low temperature in a nitrogen atmosphere. At −78° C., n-butyl lithium (ca. 58 ml) was dropwise added over 2 hrs, followed by <Intermediate 1-a> (9.4 g 31.1 mmol). After completion of the reaction, the reaction mixture was stirred, together with water (100 ml), for 30 min, and extraction gave <Intermediate 1-b>. (3.2 g, 24%)

Synthesis Example 1-(3): Synthesis of Intermediate 1-c

<Intermediate 1-b>

<Intermediate 1-c>

In a 2-L round-bottom flask reactor, <Intermediate 1-b> (55.0 g, 129 mmol), acetic acid (500 ml), and sulfuric acid (10 ml) were stirred together for 5 hrs under reflux. After completion of the reaction, the reaction mixture was cooled to room temperature, and the precipitates were filtered and washed with methanol to afford <Intermediate 1-c>. (50 g, 95%)

Synthesis Example 1-(4): Synthesis of Intermediate 1-d

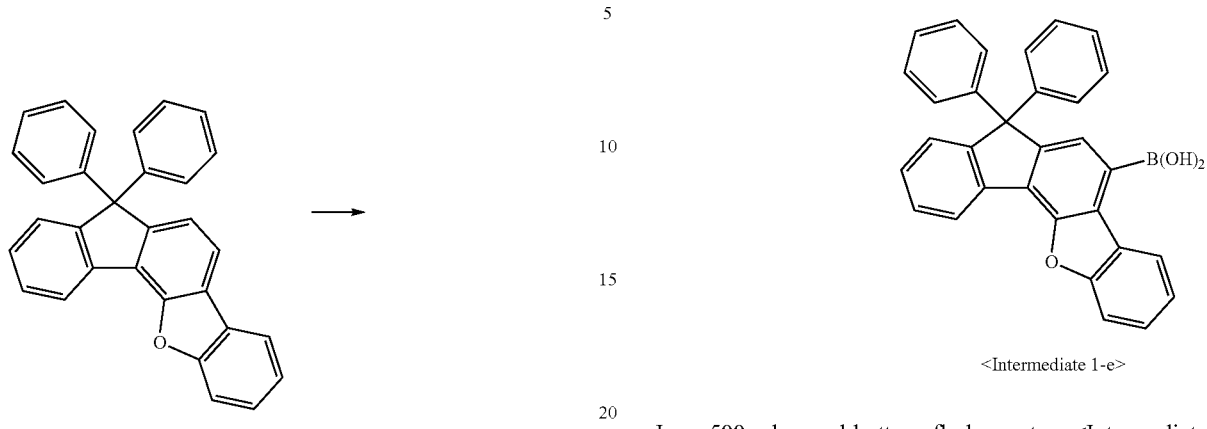

<Intermediate 1-c>

<Intermediate 1-d>

In a 2-L round-bottom flask reactor, <Intermediate 1-c> (50 g, 122 mmol) was stirred together with dichloromethane (600 ml), at room temperature. A dilution of bromine (13.7 ml, 85 mmol) in dichloromethane (50 ml) was dropwise added, followed by stirring for about 3 hrs. Recrystallization in methanol afforded <Intermediate 1-d>. (45 g, 76%)

Synthesis Example 1-(5): Synthesis of Intermediate 1-e

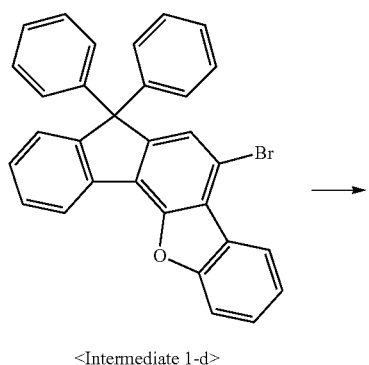

<Intermediate 1-d>

<Intermediate 1-e>

In a 500-ml round-bottom flask reactor, <Intermediate 1-d>(39.5 g, 81 mmol), bis(pinacolato)diboron (26.7 g, 105 mmol), [1,1'-bis(diphenylphosphino)ferrocene]dichloropalladium (1.3 g, 0.002 mol), potassium acetate (19.9 g, 0.202 mmol), and 1,4-dioxane (200 ml) were stirred together for 10 hrs under reflux. Thereafter, concentration in a vacuum and then purification by column chromatography were conducted. The resulting isolate was recrystallized in dichloromethane and heptane to afford <Intermediate 1-e>. (23.4 g, 68%)

Synthesis Example 1-(6): Synthesis of Compound of Chemical Formula 1

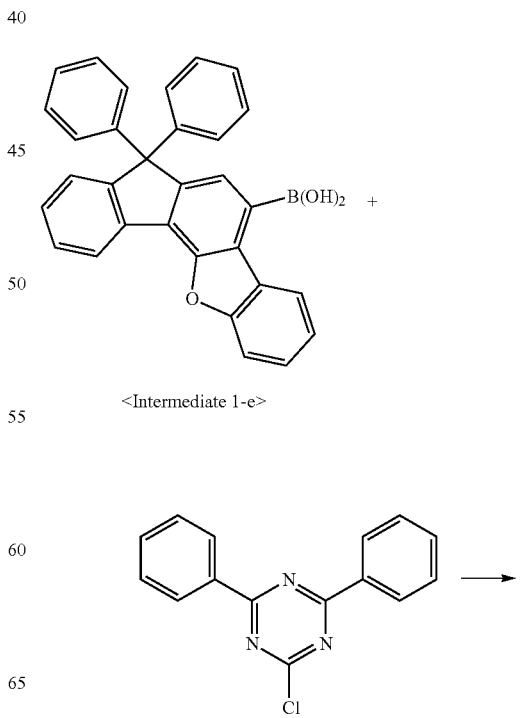

<Intermediate 1-e>

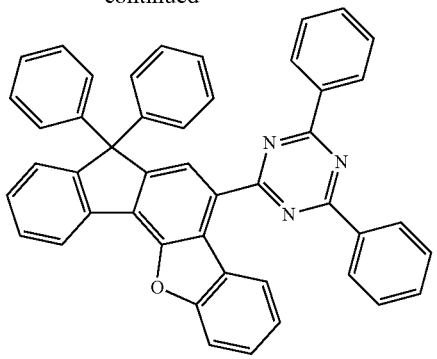

<Chemical Formula 1>

In a 300-mL reactor, 2-chloro-4,6-diphenyl-1,3,5-triazine (12.3 g, 46 mmol), <Intermediate 1-e> (24.8 g, 55 mmol), potassium carbonate (15.2 g, 91 mmol), tetrakistriphenylphosphine palladium (5.6 g, 9 mmol), water (80 mL), toluene (150 mL), and 1,4-dioxane (150 mL) were stirred for hrs under reflux. After completion of the reaction, the reaction mixture was subjected to layer separation and the organic layer thus obtained was concentrated at a reduced pressure. Purification by column chromatography afforded the compound of Chemical Formula 1. (18.8 g. 64%)

MS (MALDI-TOF): m/z 639.23 [M$^+$]

Synthesis Example 2: Synthesis of Compound of Chemical Formula 4

Synthesis Example 2-(1): Synthesis of Intermediate 2-a

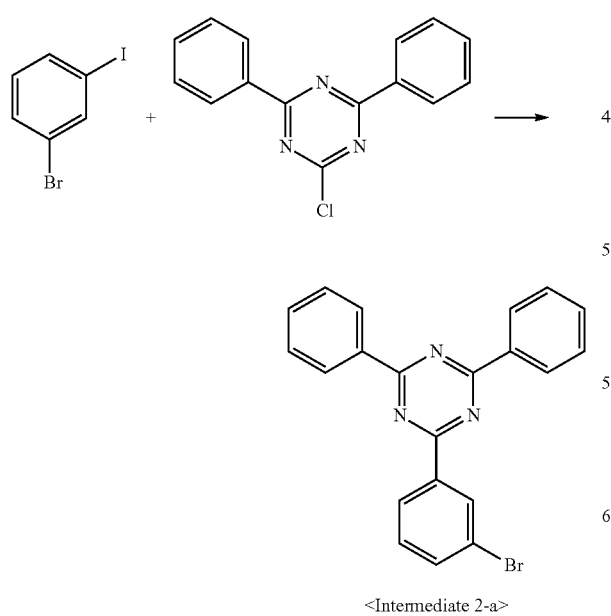

<Intermediate 2-a>

In a round-bottom, 1-bromo-3-iodobenzene (60.0 g, 212 mmol) and tetrahydrofuran (480 mL) were placed and cooled to −78° C. in a nitrogen atmosphere. After 30 min, drops of 1.6 M n-butyl lithium (126 ml, 202 mmol) was slowly added. After one hour, a solution of 2-chloro-4,6-diphenyl-1,3,5-triazine (62.4 g, 233 mmol) in tetrahydrofuran (250 mL) was slowly added in a dropwise manner and stirred for 30 min. The mixture was warmed to room temperature, stirred at room temperature for about 1 hr, and acidified with 2N HCl. Subsequent to extraction, column chromatographic purification afforded <Intermediate 2-a>. (24.7 g, 30%)

Synthesis Example 2-(2): Synthesis of Compound of Chemical Formula 4

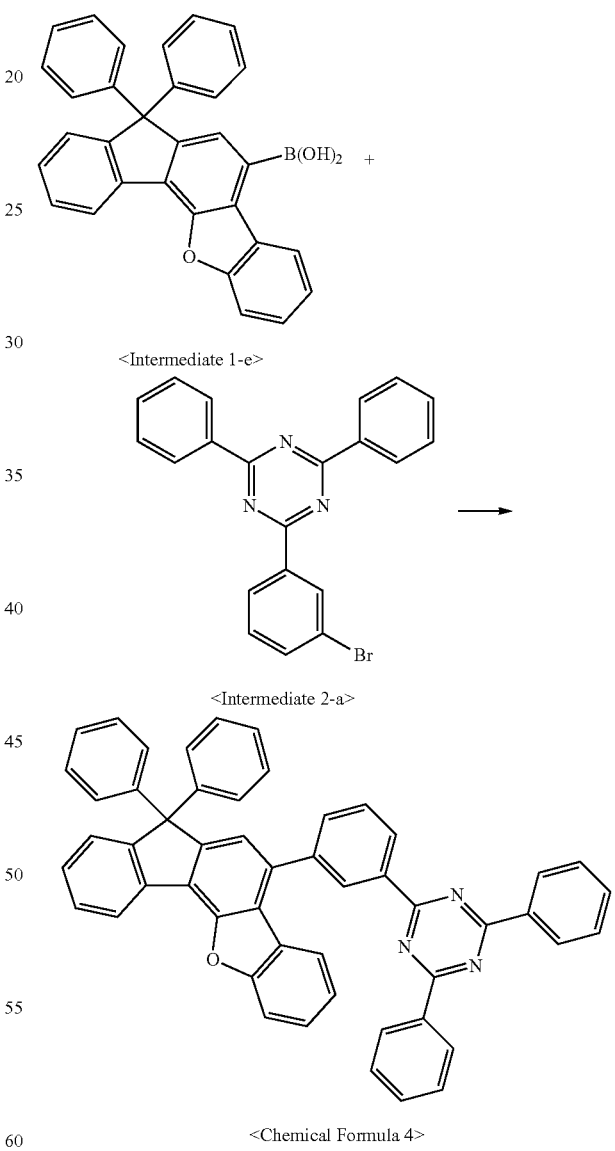

<Chemical Formula 4>

The same procedure as in Synthesis Example 1-(6) was conducted, with the exception of using <Intermediate 2-a> instead of 2-chloro-4,6-diphenyl-1,3,5-triazine, to afford <Chemical Formula 4>. (14.8 g, 57%)

MS (MALDI-TOF): m/z 715.26 [M$^+$]

Synthesis Example 3: Synthesis of Compound of Chemical Formula 46

Synthesis Example 3-(1): Synthesis of Intermediate 3-a

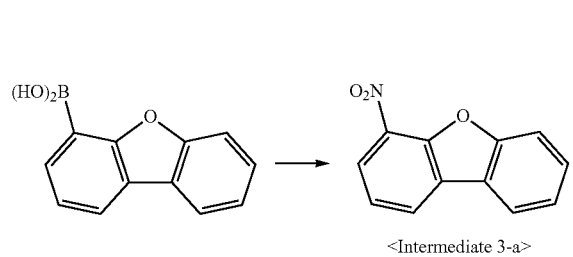 [SMILES: OB(O)c1cccc2c1oc1ccccc12 ; O=[N+]([O-])c1cccc2c1oc1ccccc12]

<Intermediate 3-a>

In a 2-L round-bottom flask reactor, 4-dibenzofuran boronic acid (85.0 g, 401 mmol), bismuth (III) nitrate pentahydrate (99.2 g, 200 mmol), and toluene (400 ml) were stirred together at 70° C. for 3 hrs in a nitrogen atmosphere. After completion of the reaction, the reaction mixture was cooled to room temperature and the solid thus formed was filtered and washed with toluene to afford <Intermediate 3-a>. (61.5 g, 72%)

Synthesis Example 3-(2): Synthesis of Intermediate 3-b

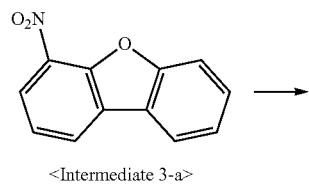

<Intermediate 3-a>

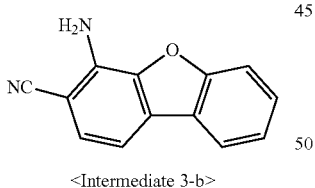

<Intermediate 3-b>

In a 2-L round-bottom flask reactor, ethyl cyanoacetate (202.9 g, 1.794 mol) and dimethyl formamide (500 ml) were placed. Potassium hydroxide (67.10 g, 1.196 mol) and potassium cyanide (38.95 g, 0.598 mol) were added, followed by dimethyl formamide (200 ml). The resulting mixture was stirred at room temperature, added with <Intermediate 3-a> (127 g, 0.737 mol) little by little, and then stirred at 50° C. for 72 hrs. After completion of the reaction, an aqueous sodium hydroxide solution (25%, 200 ml) was added and stirred for 3 hrs under reflux. After cooling to room temperature, extraction with ethyl acetate and water was conducted. The organic layer thus formed was separated, and concentrated in a vacuum. Purification by column chromatography afforded <Intermediate 3-b>. (20.0 g, 16%)

Synthesis Example 3-(3): Synthesis of Intermediate 3-c

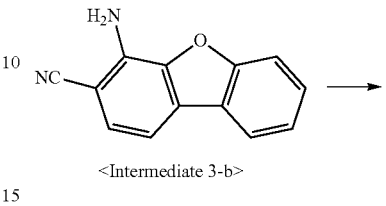

<Intermediate 3-b>

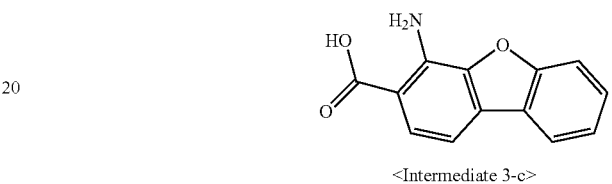

<Intermediate 3-c>

In a 2-L round-bottom flask reactor, a mixture of <Intermediate 3-b> (20.0 g, 96 mmol), ethanol (600 ml), and an aqueous potassium hydroxide solution (170 ml, 142.26 g, 2.53 mol) was stirred for 12 hrs under reflux. After completion of the reaction mixture was cooled to room temperature, and then acidified with 6 N HCl (400 ml). Stirring for 20 min was followed by filtration. The solid thus obtained was washed with ethanol to afford <Intermediate 3-c>. (17.0 g, 88.5%)

Synthesis Example 3-(4): Synthesis of Intermediate 3-d

<Intermediate 3-c>

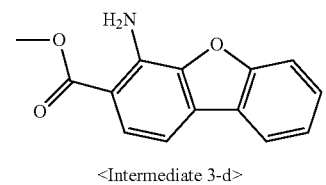

<Intermediate 3-d>

In a 2-L round-bottom flask reactor, a mixture of <Intermediate 3-c> (17.0 g, 75 mmol) and sulfuric acid (15 ml) was stirred for 72 hrs under reflux. After completion of the reaction, the reaction mixture was extracted with ethyl acetate and water. The organic layer was separated and washed with an aqueous sodium hydrogen carbonate solution. An excess of methanol was added during the vacuum concentration of the organic layer, followed by filtration to afford <Intermediate 3-d>. (14.0 g, 77.6%)

Synthesis Example 3-(5): Synthesis of Intermediate 3-e

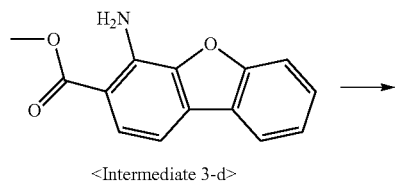

<Intermediate 3-d>

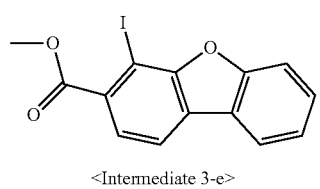

<Intermediate 3-e>

In a 500-mL round-bottom flask reactor, <Intermediate 3-d> (12 g, 50 mmol), HCl (15 ml), and water (75 ml) were stirred together for 1 hr at 0° C. At the same temperature, an aqueous solution (38 ml) of sodium nitrite (5.6 g, 81 mmol) was dropwise added to the reaction mixture and then stirred for 1 hr. An aqueous solution (38 ml) of potassium iodide (22.4 g, 135 mmol) was dropwise added with care not to increase the temperature of the reaction solution above 5° C. Stirring was continued for 5 hrs at room temperature, and after completion of the reaction, the reaction mixture was washed with an aqueous sodium thiosulfate solution and extracted with ethylacetate and water. The organic layer was separated and concentrated in a vacuum. Purification through column chromatography gave <Intermediate 3-e>. (11 g, 91%)

Synthesis Example 3-(6): Synthesis of Intermediate 3-f

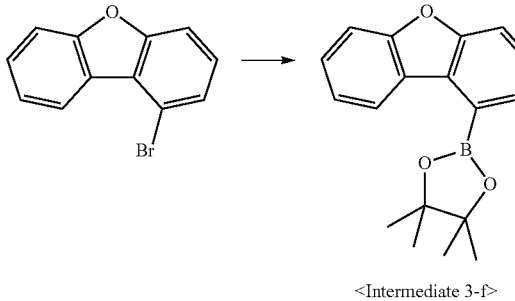

<Intermediate 3-f>

In a 500-mL round-bottom flask reactor, 1-bromodibenzofuran (20.0 g, 81 mmol), bis(pinacolato)diboron (26.7 g, 105 mmol), [1,1'-bis(diphenylphosphino)ferrocene]dichloropalladium (1.3 g, 0.002 mol), potassium acetate (19.9 g, 202 mmol), and 1,4-dioxane (200 ml) were stirred together for 10 hrs under reflux. Concentration in a vacuum was followed by column chromatographic purification. Recrystallization in dichloromethane and heptane afforded <Intermediate 3-f> (17.0 g, 70%).

Synthesis Example 3-(7): Synthesis of Intermediate 3-g

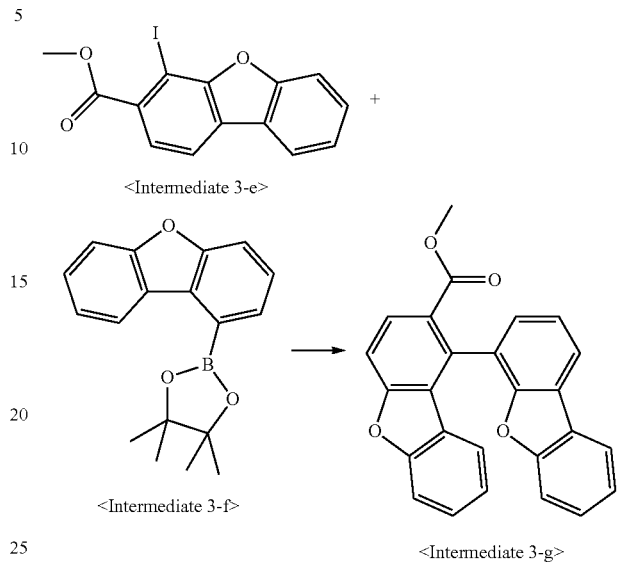

The same procedure was conducted as in Synthesis Example 1-(1), with the exception of using <Intermediate 3-e> and <Intermediate 3-f> instead of methyl 2-iodobenzoate and 4-dibenzofuran boronic acid, respectively, to synthesize <Intermediate 3-g> (10.1 g, 75%).

Synthesis Example 3-(8): Synthesis of Intermediate 3-h

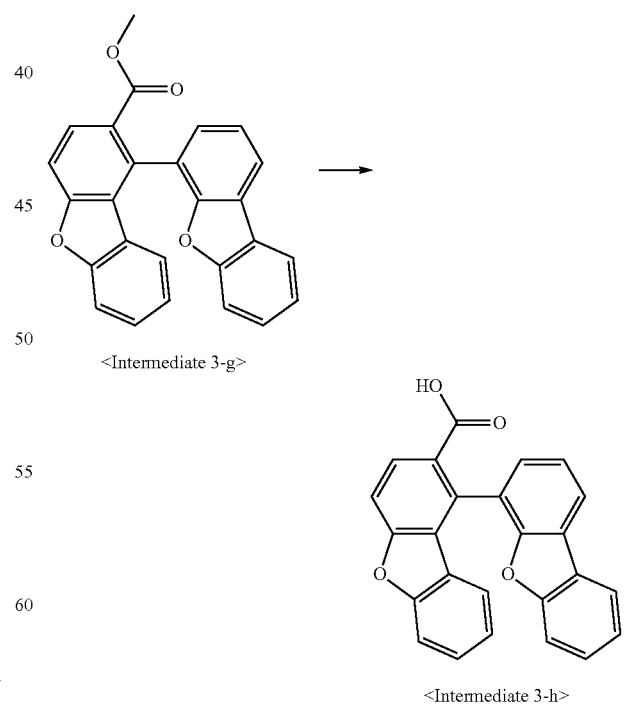

In a 500-mL round-bottom flask reactor, <Intermediate 3-g> (10.0 g, 25 mmol), sodium hydroxide (1.1 g, 28 mmol), and ethanol (80 ml) were stirred together for 48 hrs under reflux. After the completion of the reaction was confirmed by thin layer chromatography, the reaction mixture was cooled to room temperature. The chilled solution was acidified with drops of 2-N HCl, followed by stirring for 30 min. The solid thus formed was filtered, and recrystallized in dichloromethane and hexane to afford <Intermediate 3-h>. (7.3 g, 77%)

Synthesis Example 3-(9): Synthesis of Intermediate 3-i

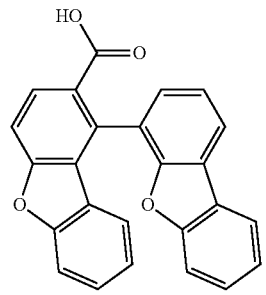

<Intermediate 3-h>

In a 250-mL round-bottom flask reactor, <Intermediate 3-h> (7 g, 18 mmol) and methanesulfonic acid (72 ml) were stirred together for 3 hrs at 80° C. After the completion of the reaction was confirmed by thin layer chromatography, the reaction mixture was cooled to room temperature and dropwise added to ice water (75 ml). After stirring for 30 min, the solid thus formed was filtered and washed with water and methanol to afford <Intermediate 3-i>. (6.1 g, 94%)

Synthesis Example 3-(10): Synthesis of Intermediate 3-j

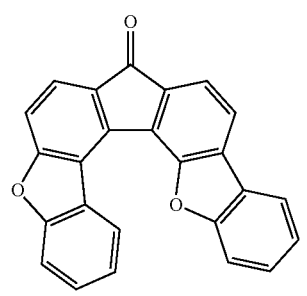

<Intermediate 3-i>

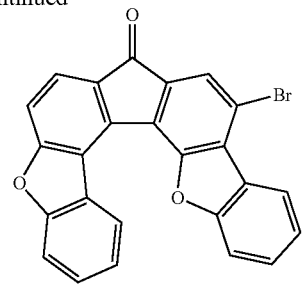

<Intermediate 3-j>

<Intermediate 3-j> was synthesized in the same manner as in Synthesis Example 1-(4), with the exception that <Intermediate 3-i> was used instead of <Intermediate 1-c>. (4.3 g, 85.3%)

Synthesis Example 3-(11): Synthesis of Intermediate 3-k

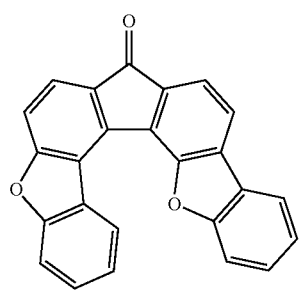

<Intermediate 3-j>

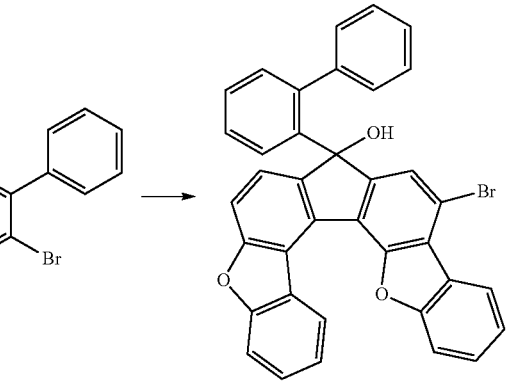

<Intermediate 3-k>

In a 250-ml round-bottom flask reactor, 2-bromobiphenyl (3.2 g, 13.7 mmol) and tetrahydrofuran (40 ml) were chilled at −78° C. in a nitrogen atmosphere. At the same temperature, n-butyl lithium (8 ml, 12 mmol) was dropwise added to the reaction solution which was then stirred for 2 hrs. Thereafter, <Intermediate 3-j> (4 g, 9.1 mmol) was added little by little to the reaction solution and stirred at room temperature. When the reaction mixture started to change color, the reaction was monitored via TLC. After the reaction was stopped with $H_2O$ (20 ml), extraction was conducted with ethyl acetate and water. The organic layer was separated, concentrated in a vacuum, and recrystallized in acetonirile to afford <intermediate 3-k>. (4 g, 74%)

Synthesis Example 3-(12): Synthesis of Intermediate 3-l

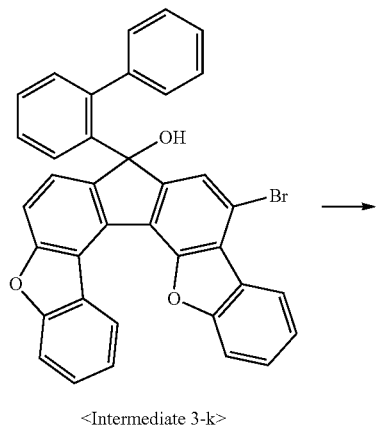

<Intermediate 3-k>

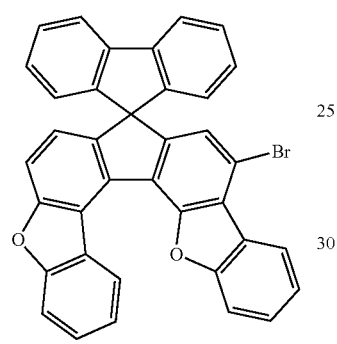

<Intermediate 3-l>

In a 250-ml round-bottom flask reactor, a mixture of <Intermediate 3-k> (4.0 g, 7 mmol), acetic acid (30 ml), and sulfuric acid (1 ml) was stirred for 5 hrs under reflux. When a precipitate was formed, the completion of the reaction was monitored using thin layer chromatography. The reaction mixture was then cooled to room temperature. The solid thus formed was filtered, washed with $H_2O$ and methanol and then dissolved in monochlorobenzene. Following silica gel chromatography, the fraction was concentrated and cooled to room temperature to give <Intermediate 3-l>. (3.5 g, 86%)

Synthesis Example 3-(13): Synthesis of Intermediate 3-m

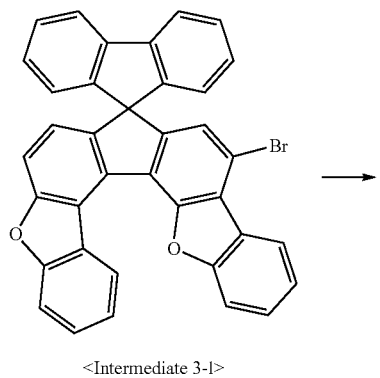

<Intermediate 3-l>

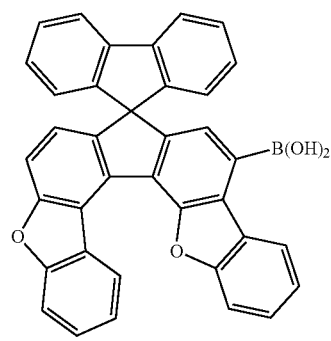

<Intermediate 3-m>

The same procedure as in Synthesis Example 1-(5) was conducted, with the exception of using <Intermediate 3-l> instead of <Intermediate 1-d>, to afford <Intermediate 3-m>. (3.9 g, 61%)

Synthesis Example 3-(14): Synthesis of <Intermediate 3-n>

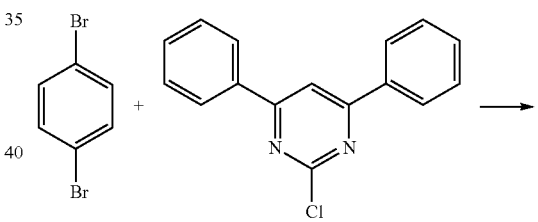

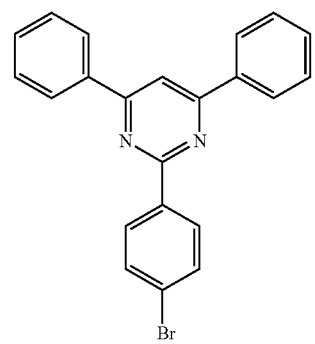

<Intermediate 3-n>

The same procedure as in Synthesis Example 2-(1) was conducted, with the exception of using 1,4-dibromobenzene and 2-chloro-4,6-diphenylpyrimidine instead of 1-bromo-3-iodobenzene and 2-chloro-4,6-diphenyl-1,3,5-triazine, respectively, to afford <Intermediate 3-n>. (14.8 g, 34%)

Synthesis Example 3-(15): Synthesis of Compound of Chemical Formula 46

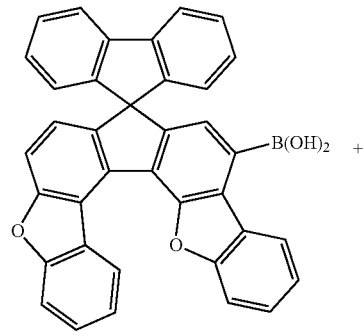

+

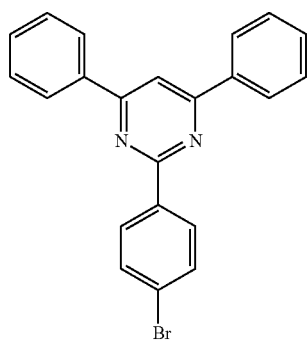

→

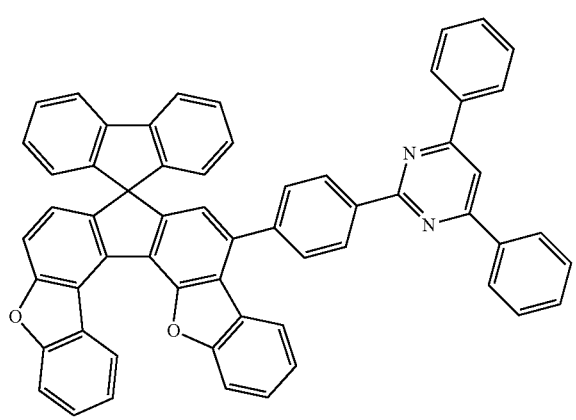

<Chemical Formula 46>

The same procedure as in Synthesis Example 1-(6) was conducted, with the exception of using <Intermediate 3-m> and <Intermediate 3-n> instead of <Intermediate 1-e> and 2-chloro-4,6-diphenyl-1,3,5-triazine, respectively, to afford <Chemical Formula 46>. (8.0 g, 51.8%)

MS (MALDI-TOF): m/z 802.26 [M⁺]

Synthesis Example 4: Synthesis of Compound of Chemical Formula 95

Synthesis Example 4-(1): Synthesis of Intermediate 4-a

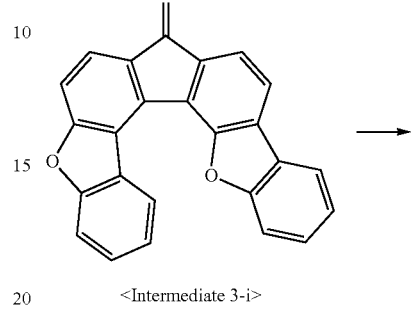

<Intermediate 3-i>

→

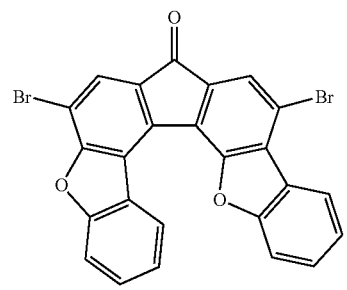

<Intermediate 4-a>

In a 100-mL round-bottom flask, <Intermediate 3-i> (3.8 g, 11 mmol) and dichloromethane (40 ml) were stirred together at room temperature. A dilution of bromine (1.1 ml, 22 mmol) in dichloromethane (10 ml) was dropwise added, followed by stirring at room temperature for 8 hrs. After completion of the reaction, the reaction mixture was stirred together with acetone (20 ml). The solid thus formed was filtered and washed with acetone. Recrystallization in monochlorobenzene afforded <Intermediate 4-a> (3.0 g, 55%).

Synthesis Example 4-(2): Synthesis of Intermediate 4-b

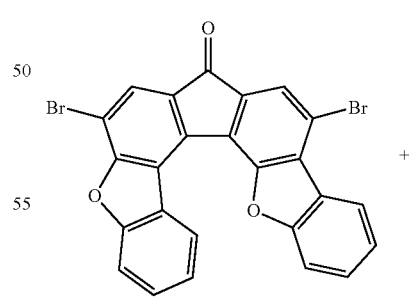

<Intermediate 4-a>

+

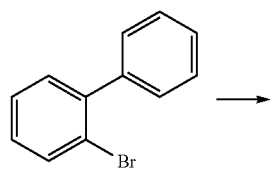

→

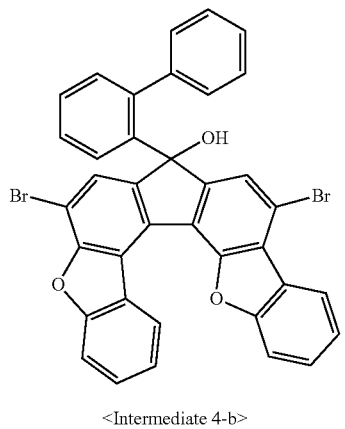

<Intermediate 4-b>

In a 100-ml round-bottom flask reactor, 2-bromobiphenyl (2.1 g, 0.009 mol) and tetrahydrofuran (30 ml) were cooled at −78° C. in a nitrogen atmosphere. At the same temperature, n-butyl lithium (4.8 ml, 0.008 mol) was dropwise added to the reaction solution, which was then stirred for 2 hrs. Thereafter, <Intermediate 4-a> (3.0 g, 0.006 mol) was added little by little to the reaction solution and stirred at room temperature. When the reaction mixture started to change color, the reaction was monitored via TLC. After the reaction was stopped with $H_2O$ (10 ml), extraction was conducted with ethyl acetate and water. The organic layer was separated, concentrated in a vacuum, and recrystallized in acetonirile to afford <Intermediate 4-b> as a solid. (2.5 g, 64%)

Synthesis Example 4-(3): Synthesis of Intermediate 4-c

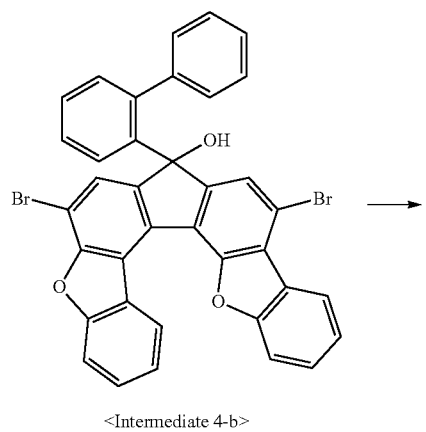

<Intermediate 4-b>

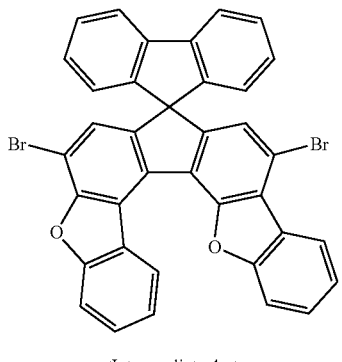

<Intermediate 4-c>

In a 100-ml round-bottom flask, a mixture of <Intermediate 4-b> (2.5 g, 0.04 mol), acetic acid (25 ml), and sulfuric acid (0.5 ml) was stirred for 5 hrs under reflux. When a precipitate was formed, the completion of the reaction was monitored using thin-layer chromatography. The reaction mixture was then cooled to room temperature and filtered. The filtrate was washed with $H_2O$ and methanol and dissolved in monochlorobenzene. Following silica gel chromatography, the fraction was concentrated and cooled to room temperature to give <Intermediate 4-c> (2.2 g, 90%).

Synthesis Example 4-(4): Synthesis of Intermediate 4-d

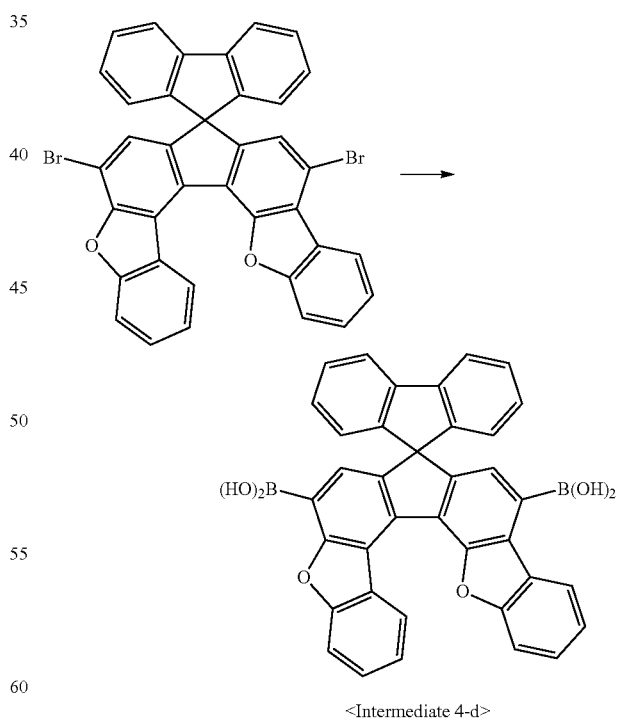

<Intermediate 4-d>

The same procedure as in Synthesis Example 1-(5) was conducted, with the exception of using <Intermediate 4-c> instead of <Intermediate 1-d>, to afford <Intermediate 4-d>. (yield 72%)

Synthesis Example 4-(5): Synthesis of Compound of Chemical Formula 95

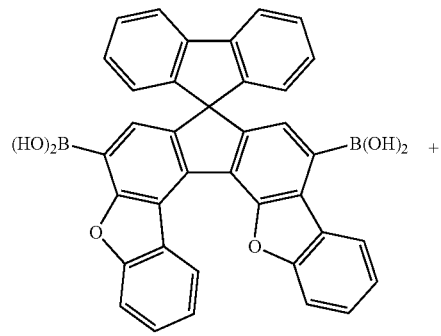

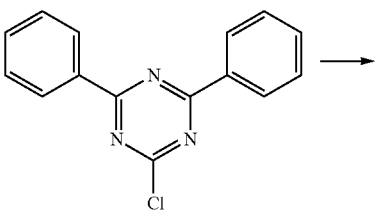

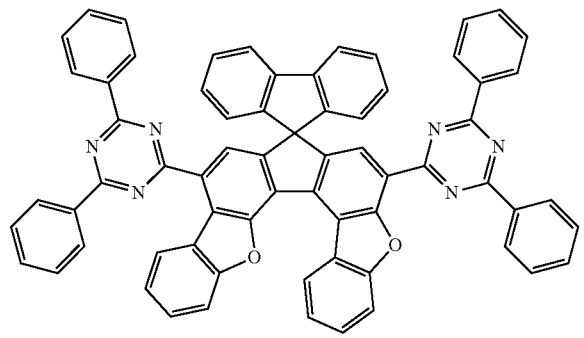

<Chemical Formula 95>

The same procedure as in Synthesis Example 1-(6) was conducted, with the exception of using <Intermediate 4-d> instead of <Intermediate 1-e>, to afford <Chemical Formula 95>. (yield 64%)

MS (MALDI-TOF): m/z 958.31 [M$^+$]

Examples 1 TO 4: Fabrication of Organic Light-Emitting Diode

An ITO glass substrate was patterned to have a luminescent area of 2 mm×2 mm and cleansed. The substrate was mounted in a vacuum chamber, which was then set to have a base pressure of 1×10$^{-6}$ torr. On the ITO glass substrate, films of HATCN (50 Å), NPD (650 Å), [BH]+blue dopant (BD) 5% (200 Å), a compound prepared according to the present invention as listed in Table 1, below (300 Å), Liq (10 Å), and Al (1,000 Å) were formed in that order. The organic light-emitting device thus obtained was measured at 10 mA/cm$^2$ for luminescence properties. Structures of [HATCN], [NPD], [BD], [BH], and [Liq] are as follows:

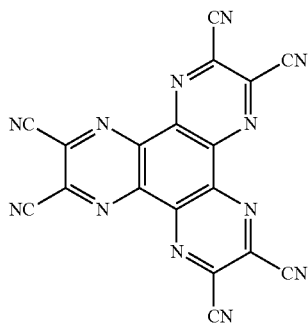

[HATCN]

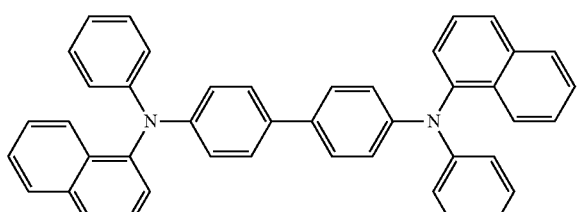

[NPD]

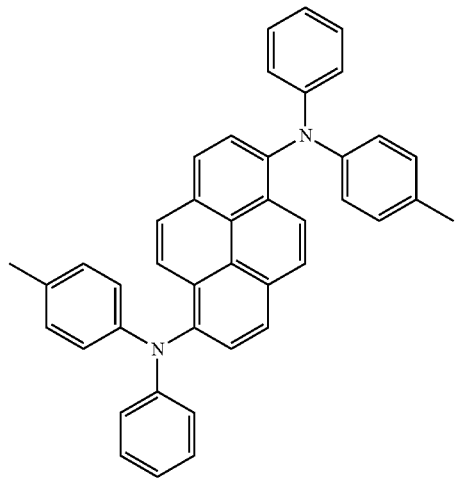

[BD]

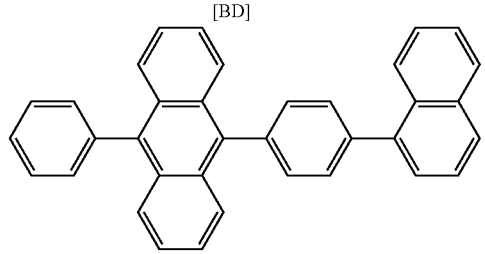

[BH]

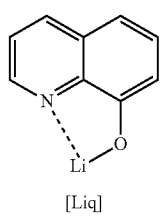

[Liq]

Comparative Example 1

An organic light-emitting diode of Comparative Example 1 was fabricated in the same manner as in the Examples, with the exception that ET, a conventional material for an electron transport layer, was used instead of the compounds prepared according to the present disclosure. The structure of ET is as follows:

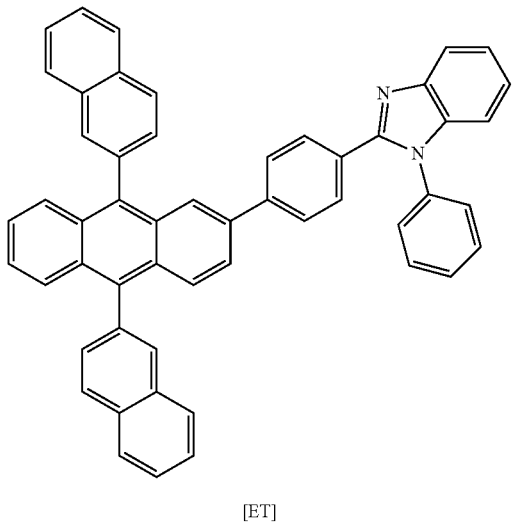 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1]

[ET]

The organic electroluminescent devices fabricated according to Examples 1 to 4 and Comparative Example 1 were measured for voltage, luminance, color coordinate, and lifespan, and the results are summarized in Table 1, below. In Table 1, $T_{95}$ refers to the time taken for luminance to decrease to 95% of the initial luminance (2000 cd/m$^2$).

TABLE 1

|  | ETL | V Driving Volt | Cd/A | Color Coordinate CIEx | CIEy | $T_{95}$ (Hrs) |
|---|---|---|---|---|---|---|
| C. Ex. 1 | ET | 4.2 | 5.2 | 0.135 | 0.114 | 24 |
| Ex. 1 | Chemical Formula 1 | 3.8 | 7.4 | 0.135 | 0.111 | 52 |
| Ex. 2 | Chemical Formula 4 | 3.9 | 7.2 | 0.136 | 0.112 | 60 |
| Ex. 3 | Chemical Formula 46 | 3.8 | 7.3 | 0.135 | 0.112 | 55 |
| Ex. 4 | Chemical Formula 95 | 3.9 | 7.2 | 0.135 | 0.113 | 50 |

As is understood from the data of Table 1, the organic compounds according to the present disclosure allow for lower driving voltages and more outstanding luminance efficiency, compared to the conventional compound of Example 1 and thus is highly likely to find applications in organic light-emitting diodes

INDUSTRIAL APPLICABILITY

Because the organic compounds according to the present disclosure exhibit more improved device characteristics and are available for the fabrication of stable and excellent devices, the present invention is industrially applicable.

The invention claimed is:
1. An organic compound, represented by the following Chemical Formula A or B:

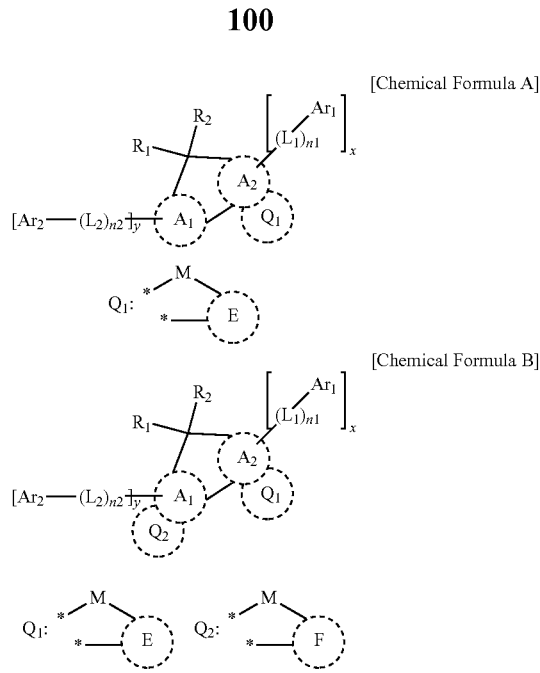

[Chemical Formula A]

[Chemical Formula B]

wherein,
A1, A2, E, and F may be the same or different and are each independently a substituted or unsubstituted aromatic hydrocarbon ring of 6 to 50 carbon atoms or a substituted or unsubstituted heteroaromatic ring of 2 to 40 carbon atoms, wherein two adjacent carbon atoms of the aromatic ring Al and two adjacent carbon atoms of the aromatic ring A2 form a 5-membered fused ring together with a carbon atom connected to both substituents R1 and R2;
linkers L1 and L2 may be the same or different and are each independently selected from among a direct bond, a substituted or unsubstituted alkylene of 1 to 60 carbon atoms, a substituted or unsubstituted alkenylene of 2 to 60 carbon atoms, a substituted or unsubstituted alkynylene of 2 to 60 carbon atoms, a substituted or unsubstituted cycloalkylene of 3 to 60 carbon atoms, a substituted or unsubstituted heterocycloalkylene of 2 to 60 carbon atoms, a substituted or unsubstituted arylene of 6 to 60 carbon atoms, and a substituted or unsubstituted heteroarylene of 2 to 60 carbon atoms;
M is any one selected from among N—R3, CR4R5, SiR6R7, GeR8R9, O, S, and Se;
Ar1 and Ar2 may be the same or different and are each independently a substituted or unsubstituted heteroaryl of 2 to 50 carbon atoms bearing at least one nitrogen atom,
n1 and n2 are each independently an integer of 1 to 3, with the proviso that when each of them is two or greater, the corresponding respective L1's and L2's are the same or different,
x is 1 and y is 0, or x and y are each 1,
R1 to R9 may be the same or different and are each independently any one selected from among a hydrogen atom, a deuterium atom, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted alkylsilyl of 1 to 30 carbon atoms, a substituted or unsubstituted arylsilyl of 6 to 30 carbon atoms, a substituted or unsubstituted alkylgermanium of 1 to 30 carbon atoms, a substituted or unsubstituted arylgermanium of 6 to 30 carbon atoms, a cyano, a nitro, and a halogen, with the proviso that R1 and R2 in Chemical Formula A are not bonded to each other, and R1 and R2 in Chemical Formula B may be bonded to each other to form a mono- or polycyclic aliphatic or aromatic ring, which may be a heterocyclic ring bearing at least one heteroatom selected from among N, O, P, Si, S, Ge, Se, and Te as a ring member;

two adjacent carbon atoms of the A2 ring moiety of Chemical Formula A may occupy respective positions * of Structural Formula Q1 to form a fused ring, and two adjacent carbon atoms of the A1 ring moiety of Chemical Formula B may occupy respective positions * of structural Formula Q2 to form a fused ring, and two adjacent carbon atoms of the A2 ring moiety of Chemical Formula B may occupy respective positions * of Structural Formula Q1 to form a fused ring;

wherein the term "substituted" in the expression "substituted or unsubstituted" used for Chemical Formulas A and B means having at least one substituent selected from the group consisting of a deuterium atom, a cyano, a halogen, a hydroxy, a nitro, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, a heteroaryl of 2 to 24 carbon atoms or a heteroarylalkyl of 2 to 24 carbon atoms, an alkoxy of 1 to 24 carbon atoms, an alkylamino of 1 to 24 carbon atoms, an arylamino of 6 to 24 carbon atoms, a heteroarylamino of 1 to 24 carbon atoms, an alkylsilyl of 1 to 24 carnon atoms, an arylsilyl of 6 to 24 carbon atoms, and an aryloxy of 6 to 24 carbon atoms.

2. The compound of claim 1, wherein $A_1$, $A_2$, E, and F in Chemical Formula A or B may be the same or different and are each independently a substituted or unsubstituted aromatic hydrocarbon ring of 6 to 50 carbon atoms.

3. The compound of claim 2, wherein the substituted or unsubstituted aromatic hydrocarbon ring of 6 to 50 carbon atoms may be independently selected from among compounds represented by Structural Formulas 10 to 21:

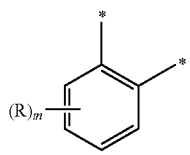

[Structural Formula 10]

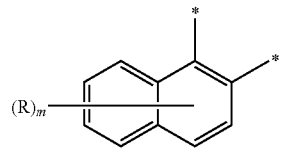

[Structural Formula 11]

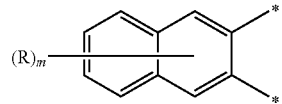

[Structural Formula 12]

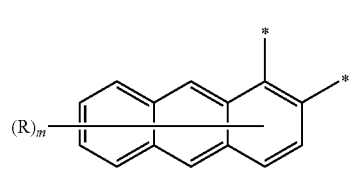

[Structural Formula 13]

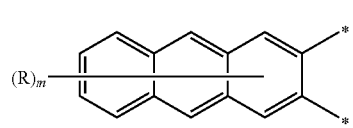

[Structural Formula 14]

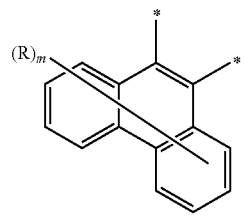

[Structural Formula 15]

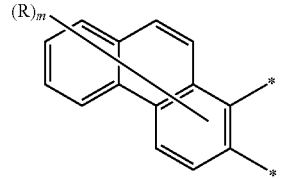

[Structural Formula 16]

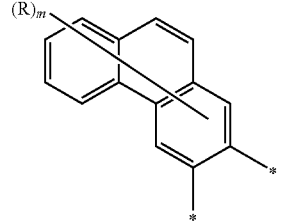

[Structural Formula 17]

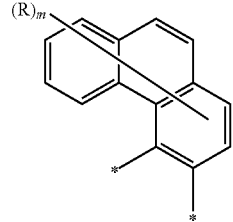

[Structural Formula 18]

[Structural Formula 19]

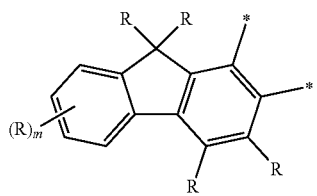

[Structural Formula 20]

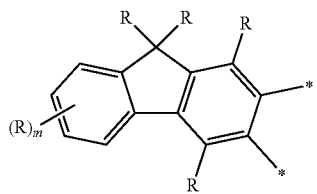

[Structural Formula 21]

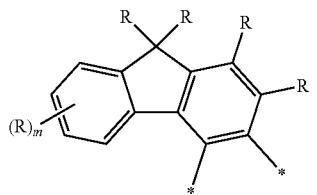

wherein,

"-*" denotes a bonding site for forming a 5-membered ring bearing the carbon atom connected to the substituents $R_1$ and $R_2$ or a bonding site for forming a 5-membered ring bearing M of Structural Formulas $Q_1$ and $Q_2$;

when one of the aromatic hydrocarbon rings of [Structural Formula 10] to [Structural Formula 21] for $A_1$ or $A_2$ is bonded to Structural Formula $Q_1$ or $Q_2$, two adjacent carbon atoms of the aromatic hydrocarbon ring occupy respective positions * of Structural Formula Qi or Q2 to form a fused ring;

R's are the same as defined in claim 1; and m is an integer of 1 to 8, with the proviso that when m is 2 or greater or two or more R's exist, the corresponding R's may be the same or different.

4. The compound of claim 1, wherein the linkers $L_1$ and $L_2$ in Chemical Formula A or B are each a single bond or one selected from among compounds represented by the following Structural Formulas 22 to 30, and n1 and n2 are each 1 or 2:

[Structural Formula 22]

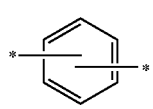

[Structural Formula 23]

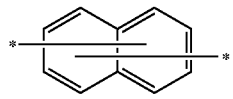

[Structural Formula 24]

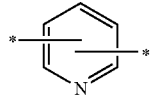

[Structural Formula 25]

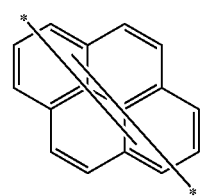

[Structural Formula 26]

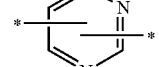

[Structural Formula 27]

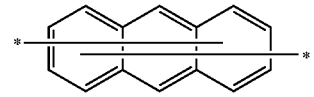

[Structural Formula 28]

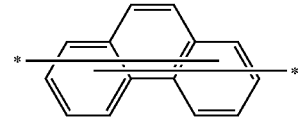

[Structural Formula 29]

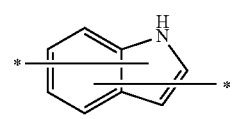

[Structural Formula 30]

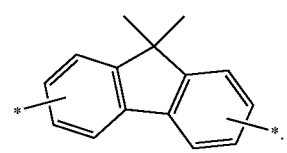

wherein each of the unsubstituted carbon atoms of the aromatic ring moiety is bound with a hydrogen atom or a deuterium atom.

5. The compound of claim 4, wherein x is 1 and y is 0 in Chemical Formulas A and B.

6. The compound of claim 1, wherein when substituents $Ar_1$ and $Ar_2$ in Chemical Formulas A and B are each a substituted or unsubstituted heteroaryl of 2 to 50 carbon atoms bearing at least one nitrogen atoms, the substituted or unsubstituted heteroaryl of 2 to 50 carbon atoms is any one selected from among the following Structural Formulas 1 to 3:

[Structural Formula 1]

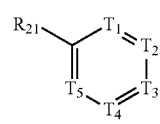

[Structural Formula 2]

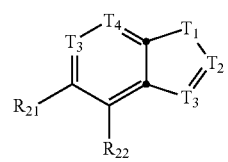

-continued

[Structural Formula 3]

wherein

T$_1$ to T$_6$ may be the same or different and are each independently one selected from among C(R$_{11}$), C(R$_{11}$)(R$_{12}$), N, N(R$_{13}$), O, and S; and R$_{11}$ to R$_{13}$, R$_{21}$, and R$_{22}$ may be the same or different and are each independently one selected from among a hydrogen atom, a deuterium atom, a substituted or unsubstituted alkyl of 1 to 30 carbon atoms, a substituted or unsubstituted aryl of 6 to 50 carbon atoms, a substituted or unsubstituted cycloalkyl of 3 to 30 carbon atoms, a substituted or unsubstituted aryl of 6 to 50 carbon atoms, and a substituted or unsubstituted heteroaryl of 2 to 50 carbon atoms bearing O, N, or S as a heteroatom, with the proviso that one of R$_{11}$ to R$_{13}$, R$_{21}$, and R$_{22}$ represents a single bond to the linker L$_1$ or L$_2$ in Chemical Formulas A and B.

7. The compound of claim 6, wherein the substituents Ar1 and Ar2 represented by Structural Formulas 1 to 3 are the substituted or unsubstituted heteroaryl of 2 to 50 carbon atoms wherein one to three nitrogen atoms, instead of carbon atoms, exist in the aromatic ring moiety.

8. The compound of claim 6, wherein Ar$_1$ and Ar$_2$ in Chemical Formulas A and B are each one of the following substituents 201 to 413:

[Substituent 201]

[Substituent 202]

[Substituent 203]

[Substituent 204]

[Substituent 205]

[Substituent 206]

[Substituent 301]

[Substituent 302]

[Substituent 303]

[Substituent 304]

[Substituent 305]

[Substituent 306]

[Substituent 307]

[Substituent 308]

[Substituent 401]

[Substituent 402]

[Substituent 403]

[Substituent 404]

-continued

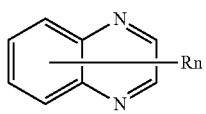
[Substituent 405]

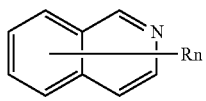
[Substituent 406]

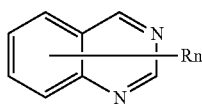
[Substituent 407]

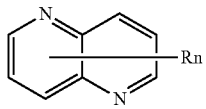
[Substituent 408]

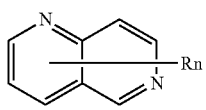
[Substituent 409]

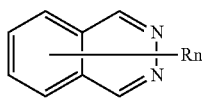
[Substituent 410]

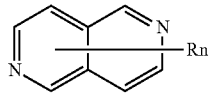
[Substituent 411]

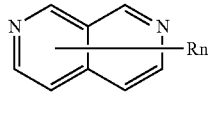
[Substituent 412]

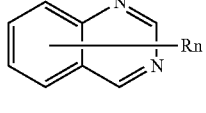
[Substituent 413]

wherein,
R's may be the same or different and are each independently selected from among a hydrogen atom, a deuterium atom, a halogen atom, a hydroxyl, a cyano, a nitro, an amino, an amidino, a hydrazine, a hydrazone, a carboxyl or a salt thereof, a sulfonic acid or a salt thereof, a phosphoric acid or a salt thereof, a substituted or unsubstituted alkyl of 1 to 20 carbon atoms, a substituted or unsubstituted akenyl of 2 to 20 carbon atoms, a substituted or unsubstituted alkynyl of 2 to 20 carbon atoms, a substituted or unsubstituted alkoxy of 1 to 20 carbon atoms, a substituted or unsubstituted alkylthio of 1 to 20 carbon atoms, a substituted or unsubstituted cycloalkyl of 3 to 20 carbon atoms, a substituted or unsubstituted aryl of 6 to 30 carbon atoms, a substituted or unsubstituted aryloxy of 6 to 30 carbon atoms, a substituted or unsubstituted arylthio of 6 to 30 carbon atoms, a substituted or unsubstituted heteroaryl of 2 to 30 carbon atoms, a substituted or unsubstituted (alkyl)amino of 1 to 20 carbon atoms, a di(substituted or unsubstituted alkyl)amino of 1 to 20 carbon atoms, a substituted or unsubstituted arylamino of 6 to 30 carbon atoms, a di(substituted or unsubstituted aryl)amino of 6 to 30 carbon atoms, a substituted or unsubstituted alkylsilyl of 1 to 30 carbon atoms, a substituted or unsubstituted arylsilyl of 6 to 30 carbon atoms, geramanium, phosphorous, and boron, wherein the substitutents may form a fused ring with adjacent groups;

n is an integer of 0 to 9;

the aromatic ring moieties within the heteroaryl radicals of Substituents 201 to 413 each have a hydrogen atom on the carbon members to which the substituent R is not bonded; and one of R's represents a single bond to $L_1$ or $L_2$ in Chemical Formula A or B.

9. The compound of claim 1, being selected from among the compounds represented by the following Chemical Formulas 1 to 82 and 84 to 101:

<Chemical Formula 1>

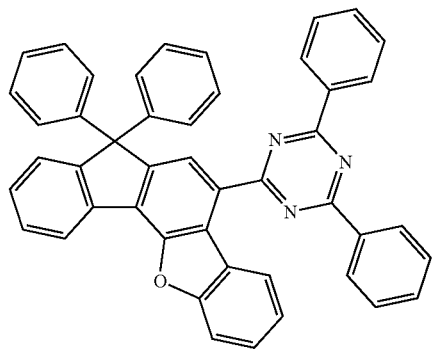

<Chemical Formula 2>

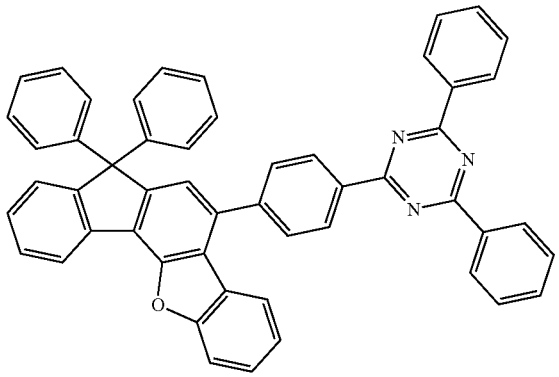

<Chemcial Formula 3>

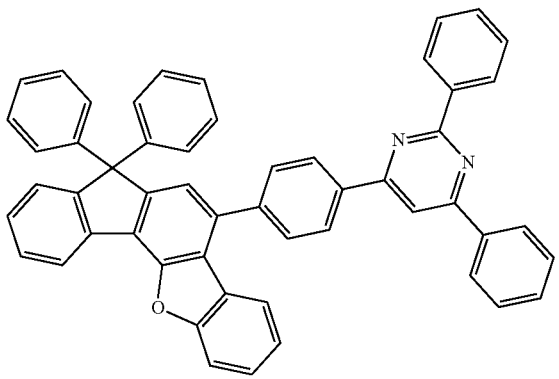

<Chemical Formula 4>
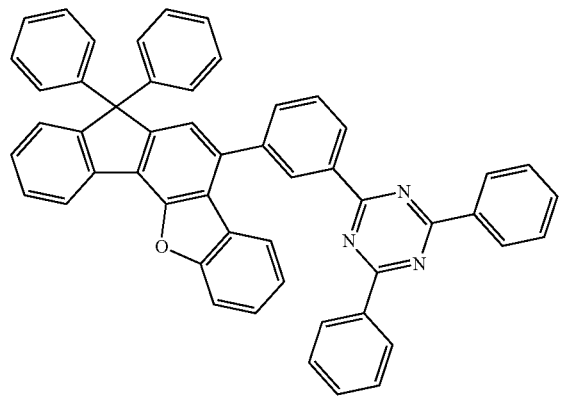
<Chemical Formula 5>
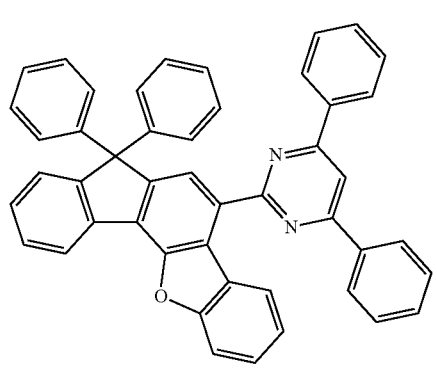
<Chemical Formula 6>
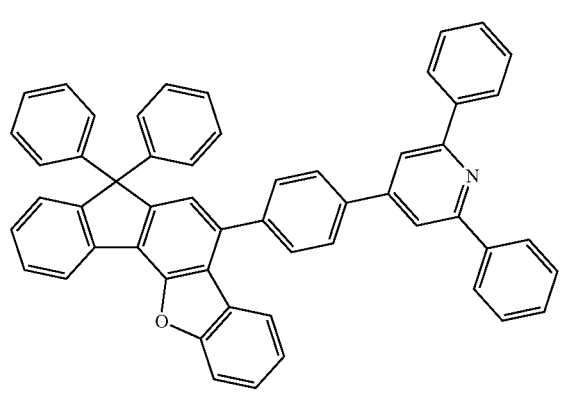
<Chemical Formula 7>
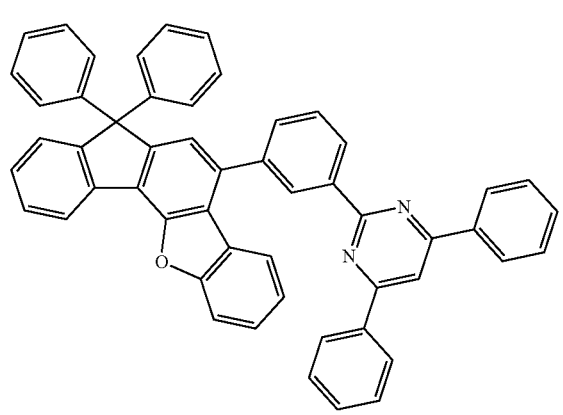
<Chemical Formula 8>
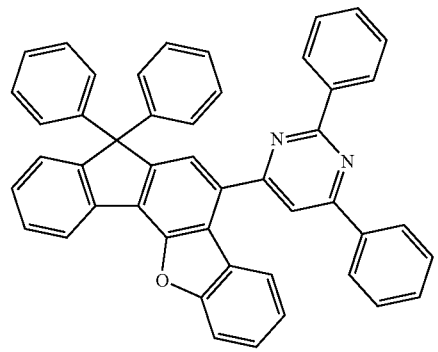
<Chemical Formula 9>
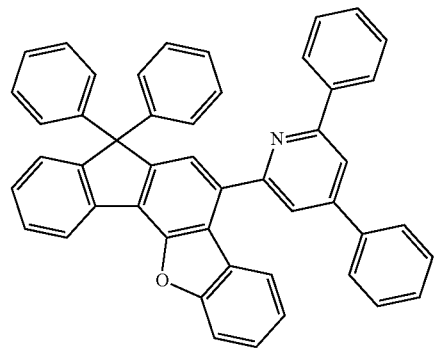
<Chemical Formula 10>
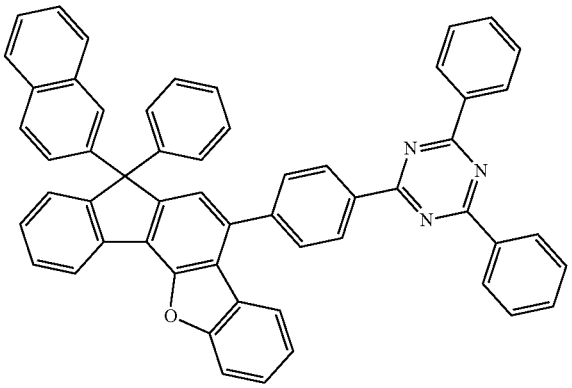
<Chemical Formula 11>
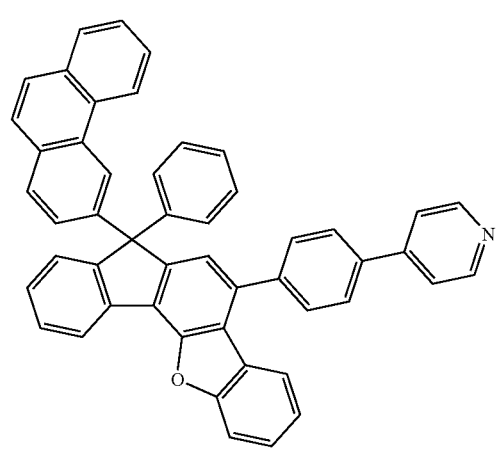

-continued
<Chemical Formula 12>
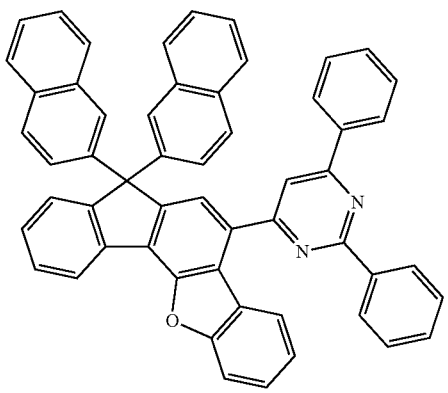
<Chemical Formula 13>
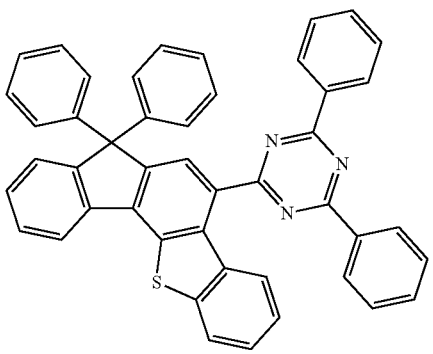
<Chemical Formula 14>
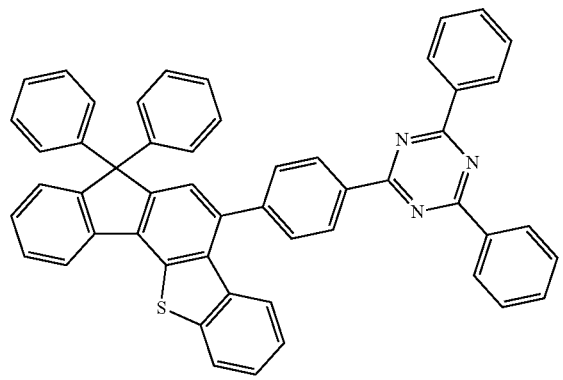
<Chemical Formula 15>
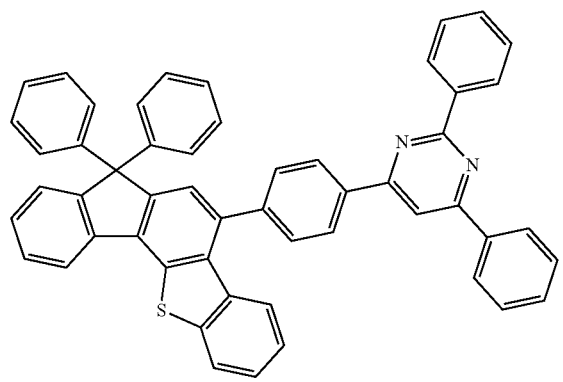
-continued
<Chemical Formula 16>
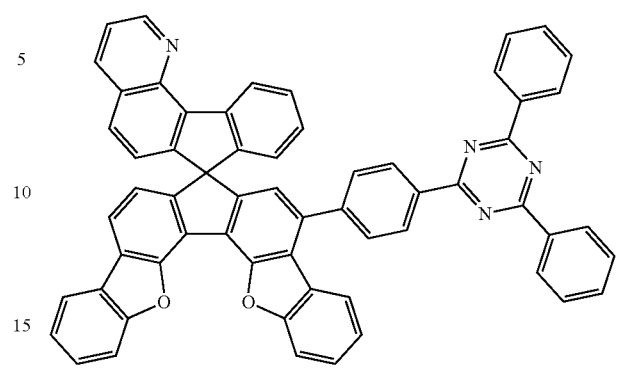
<Chemical Formula 17>
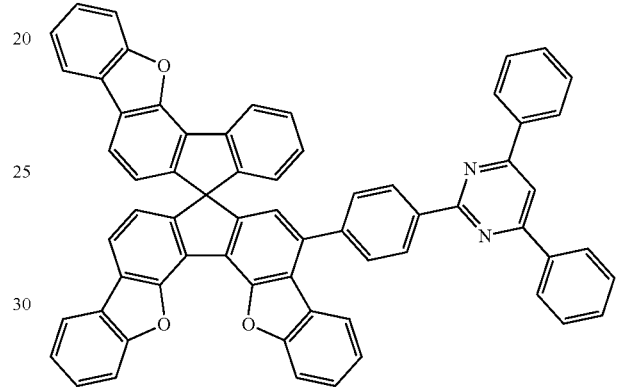
<Chemical Formula 18>
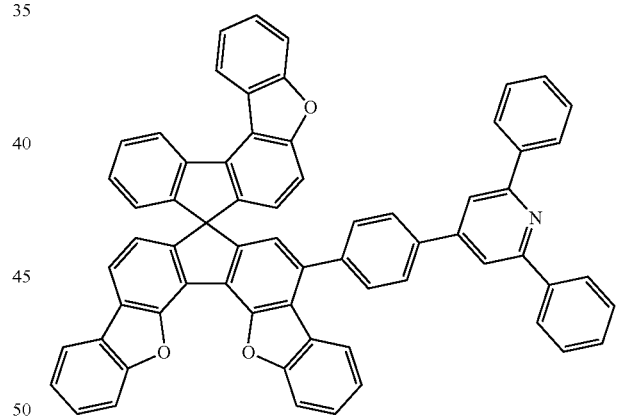
<Chemical Formula 19>
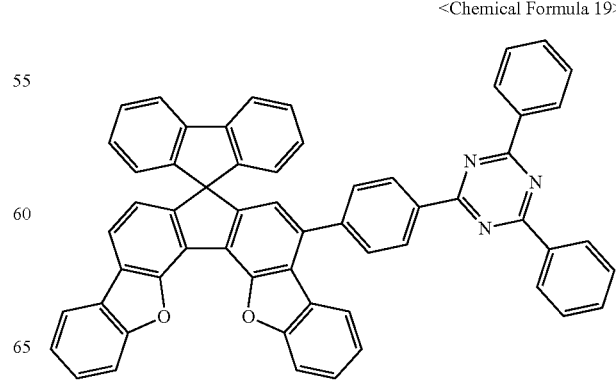

<Chemical Formula 20>
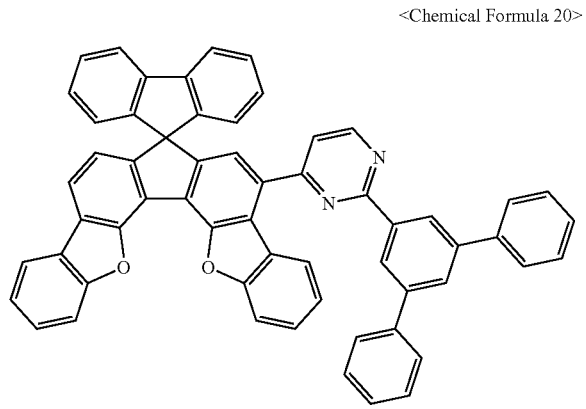
<Chemical Formula 21>
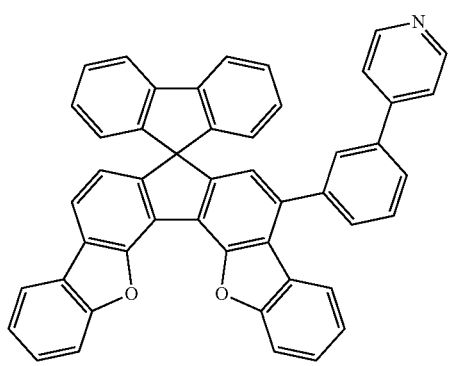
<Chemical Formula 22>
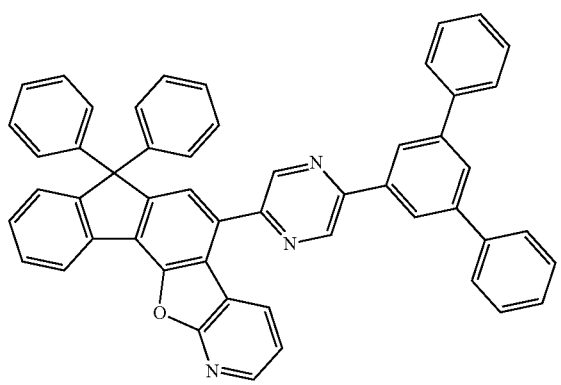
<Chemical Formula 23>
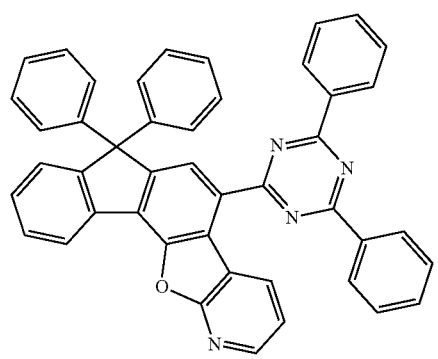
<Chemical Formula 24>
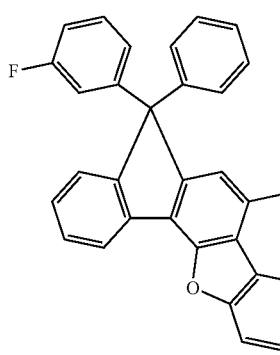
<Chemical Formula 25>
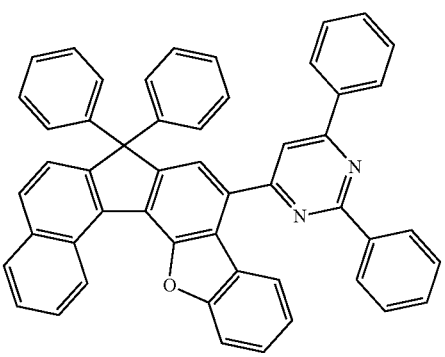
<Chemical Formula 26>
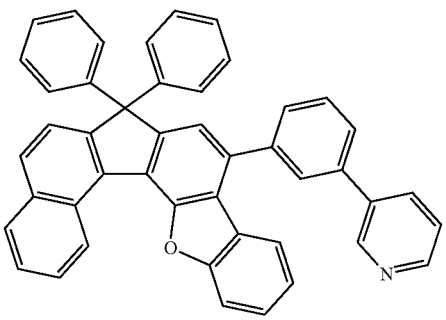
<Chemical Formula 27>
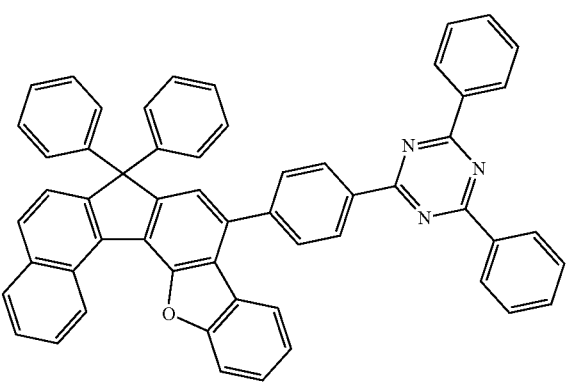

<Chemical Formula 28>
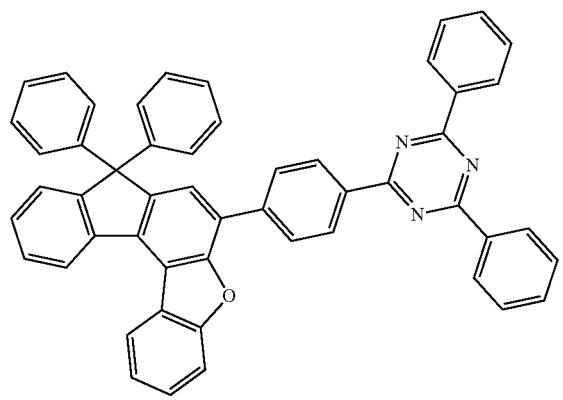
<Chemical Formula 29>
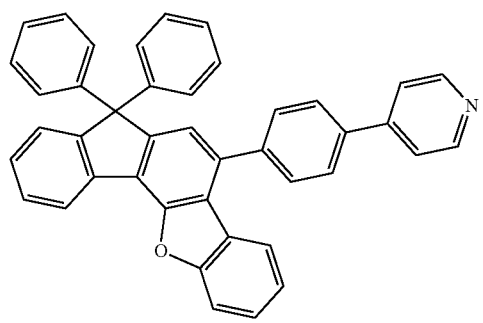
<Chemical Formula 30>
<Chemical Formula 31>
<Chemical Formula 32>
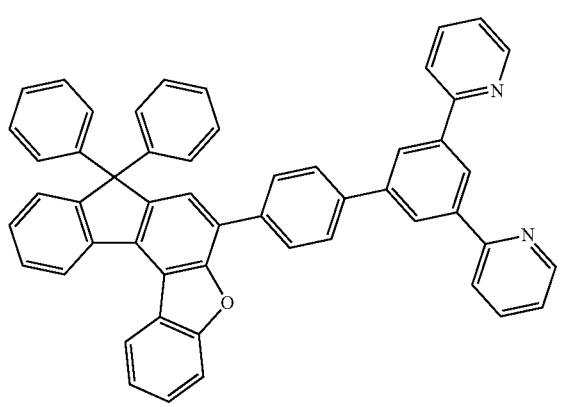
<Chemcial Formula 33>
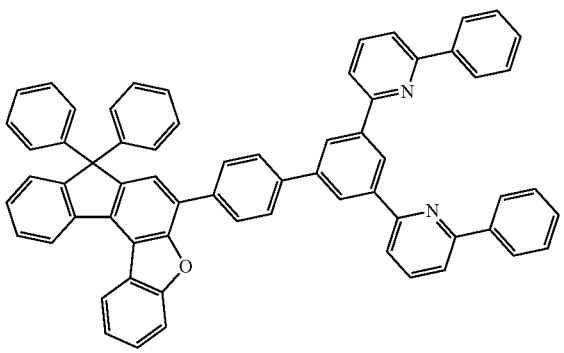
<Chemical Formula 34>
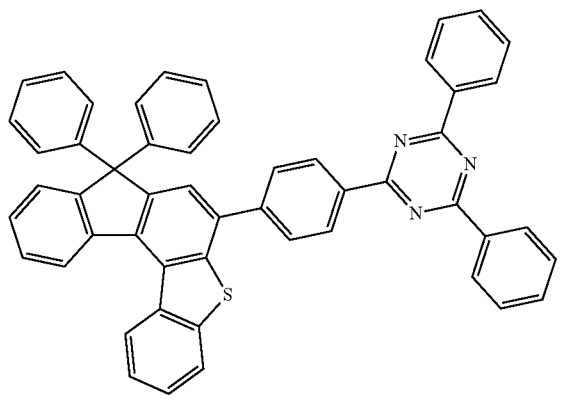
<Chemical Formula 35>
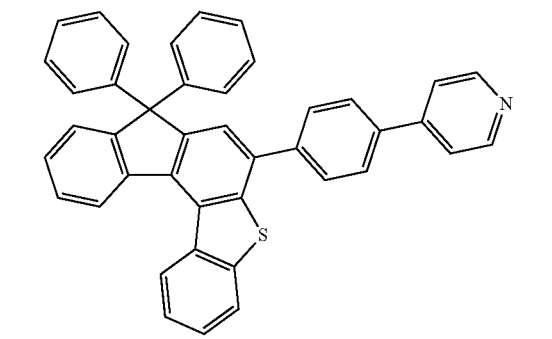

<Chemical Formula 36>
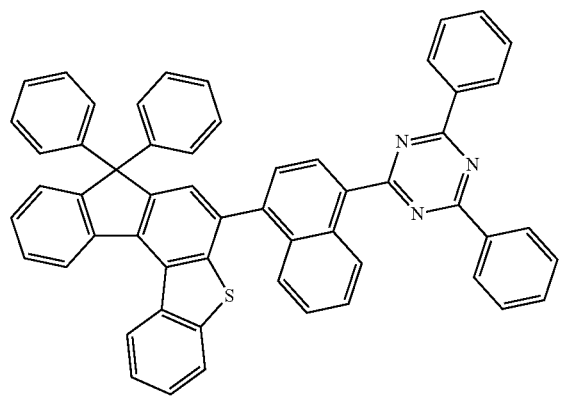
<Chemical Formula 37>
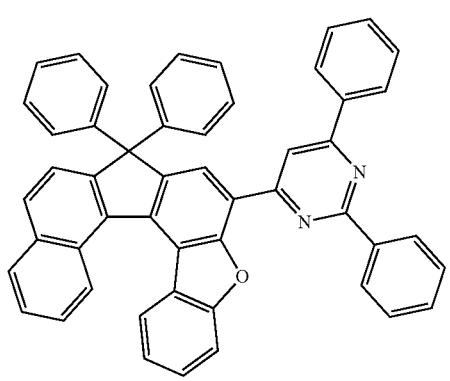
<Chemical Formula 38>
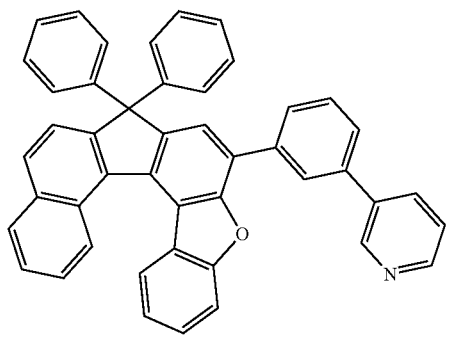
<Chemical Formula 39>
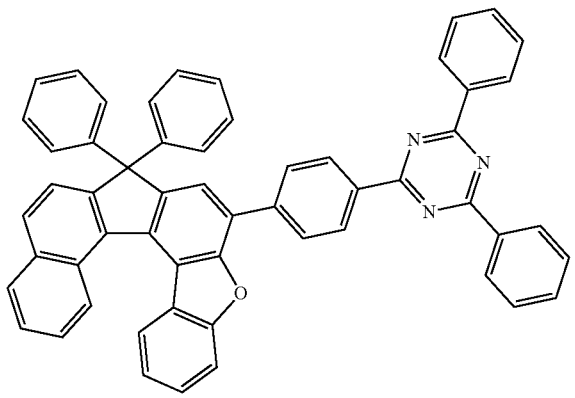
<Chemical Formula 40>
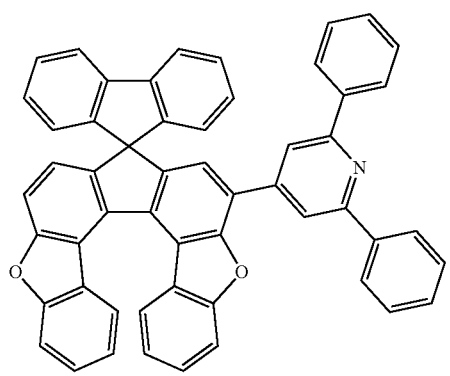
<Chemical Formula 41>
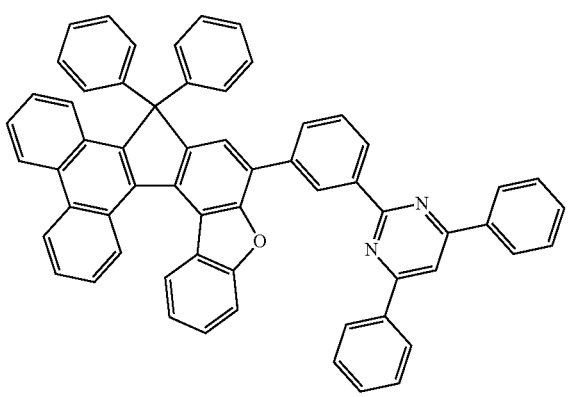
<Chemical Formula 42>
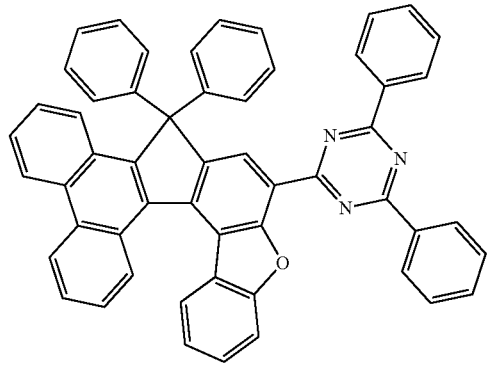
<Chemical Formula 43>
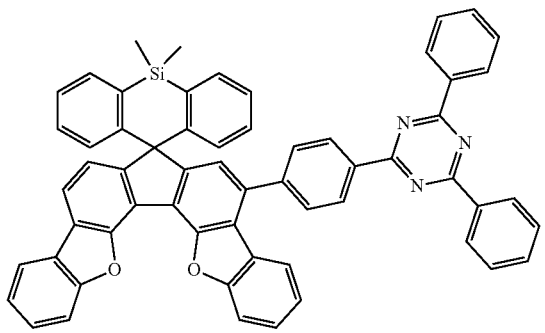

<Chemical Formula 44>
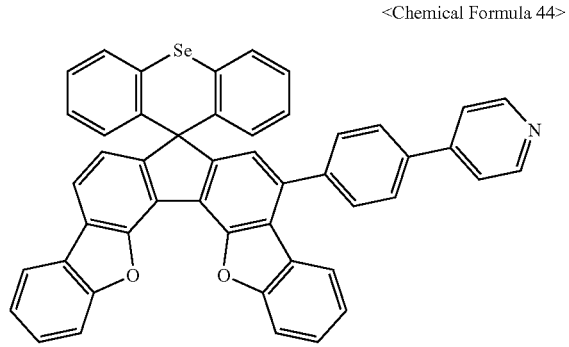
<Chemical Formula 45>
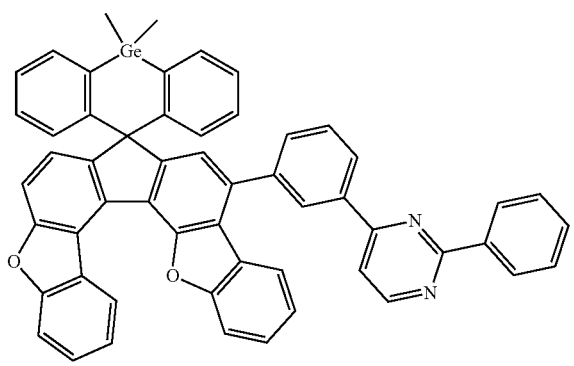
<Chemical Formula 46>
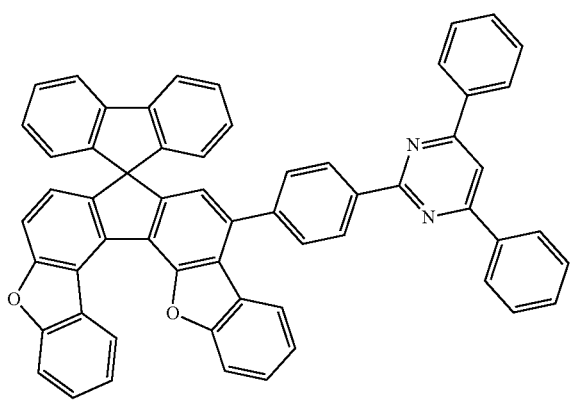
<Chemical Formula 47>
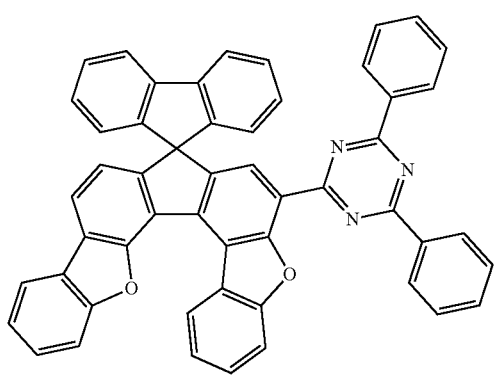
<Chemical Formula 48>
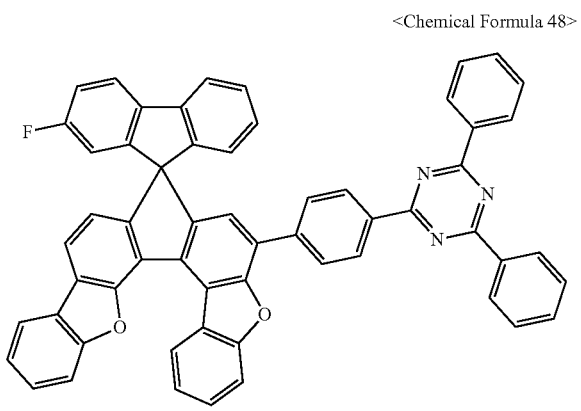
<Chemical Formula 49>
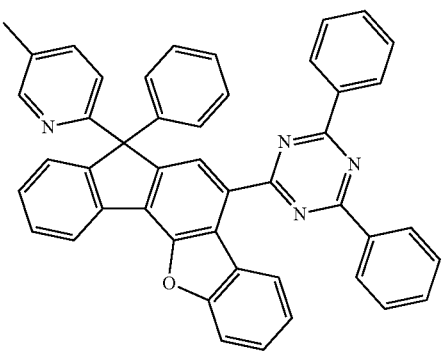
<Chemical Formula 50>
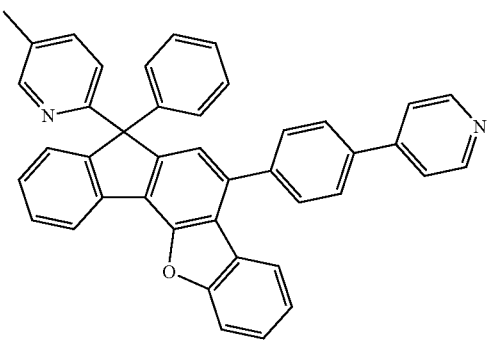
<Chemical Formula 51>
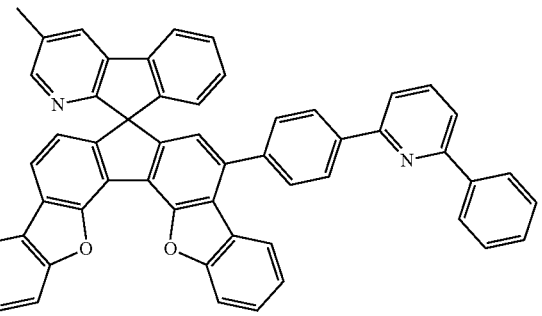

121
-continued
<Chemical Formula 52>
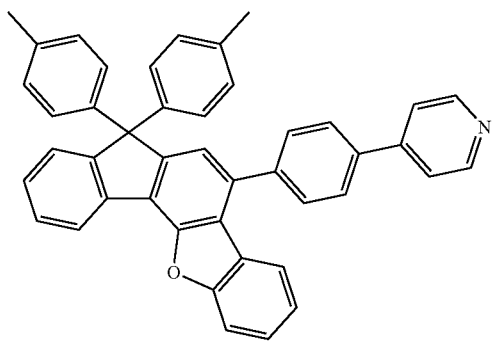
<Chemical Formula 53>
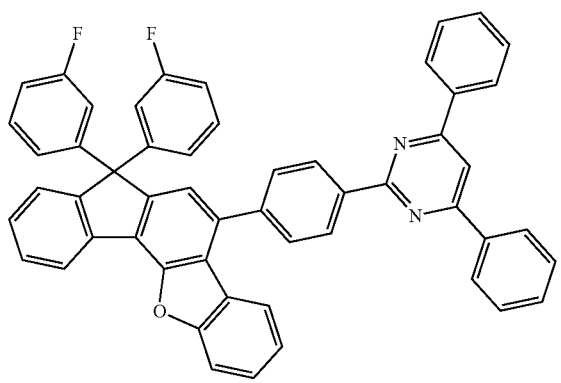
<Chemical Formula 54>
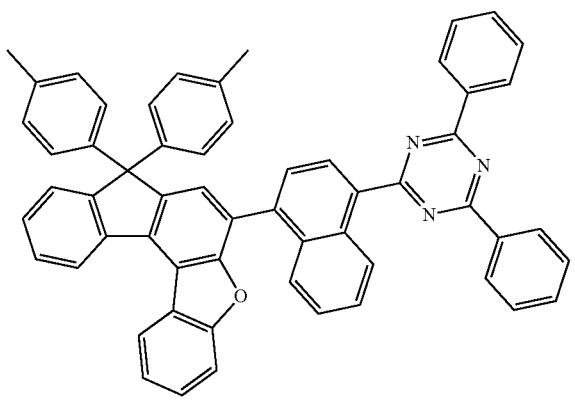
<Chemical Formula 55>
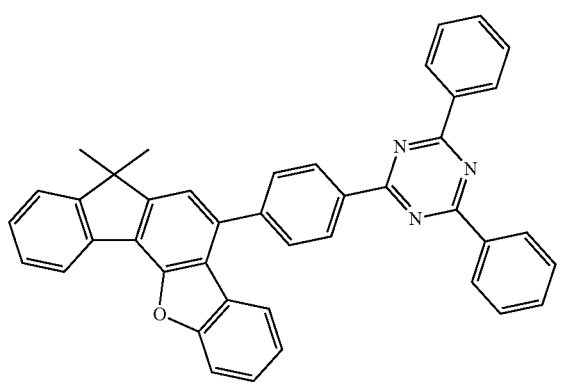
122
-continued
<Chemical Formula 56>
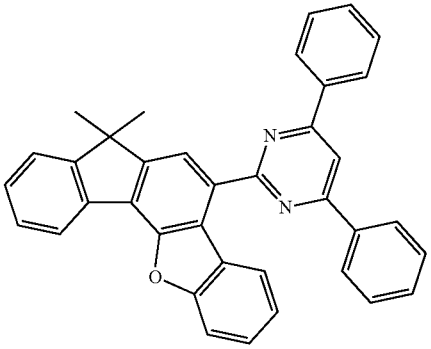
<Chemical Formula 57>
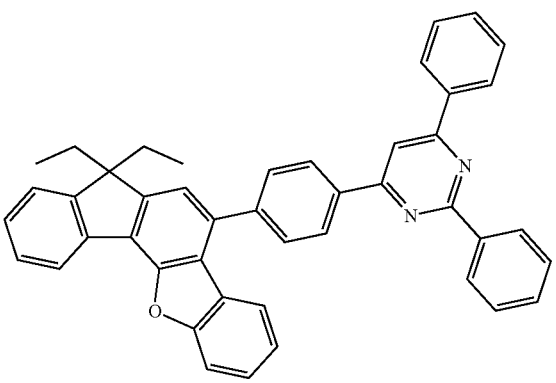
<Chemical Formula 58>
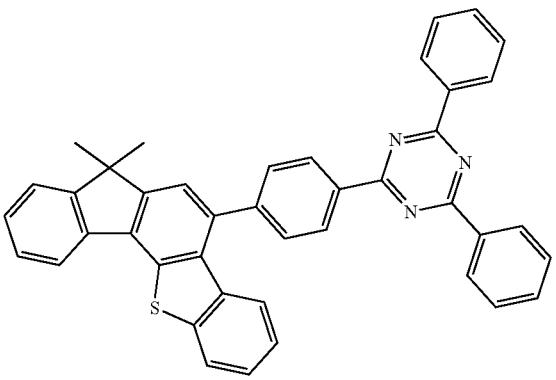
<Chemical Formula 59>
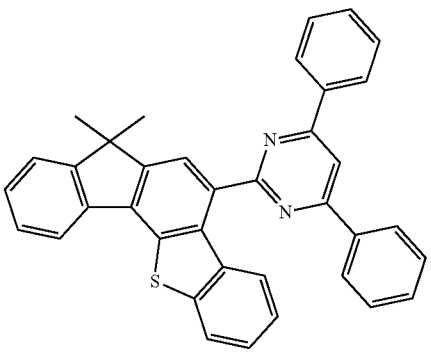

<Chemical Formula 60>
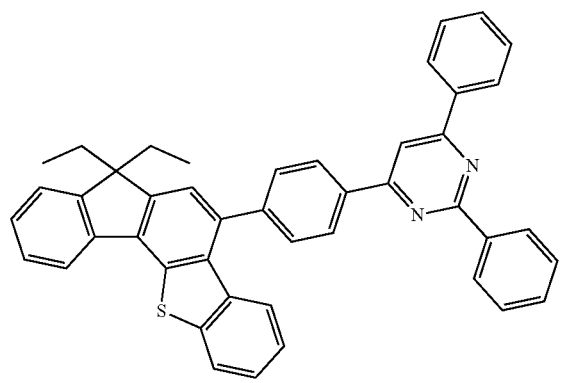
<Chemical Formula 61>
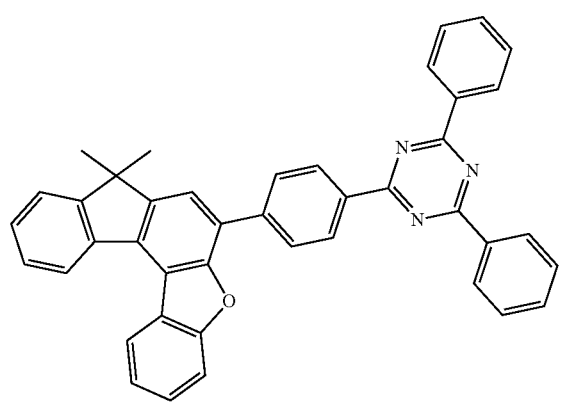
<Chemical Formula 62>
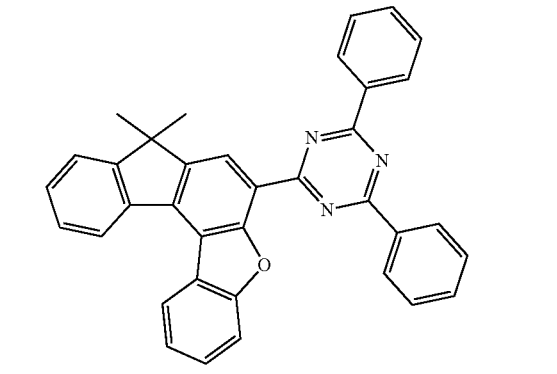
<Chemical Formula 63>
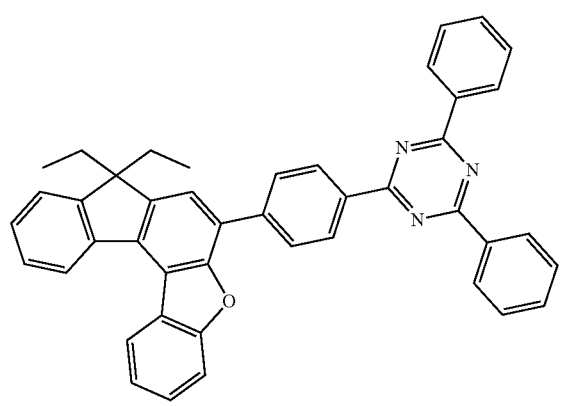
<Chemical Formula 64>
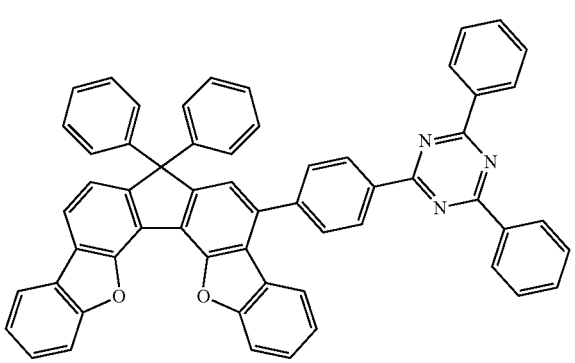
<Chemical Formula 65>
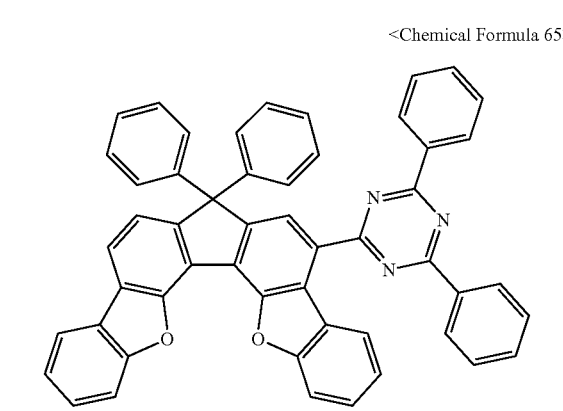
<Chemical Formula 66>
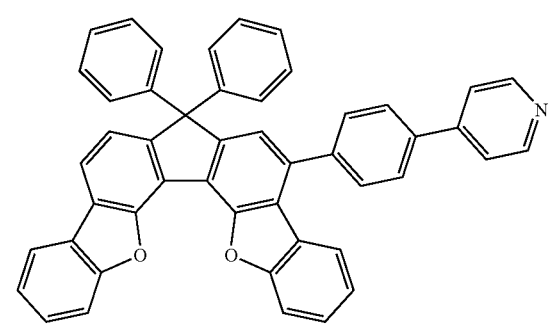
<Chemical Formula 67>
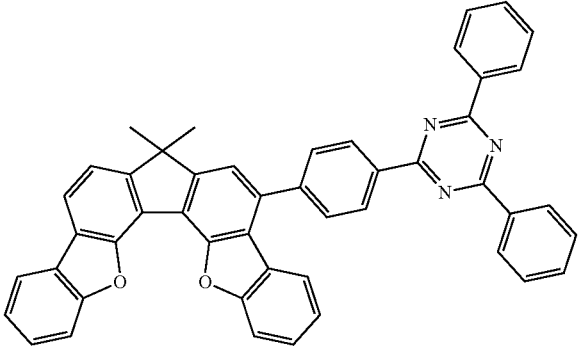

<Chemical Formula 68>
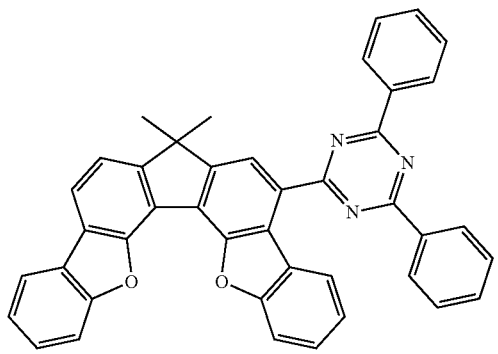
<Chemical Formula 69>
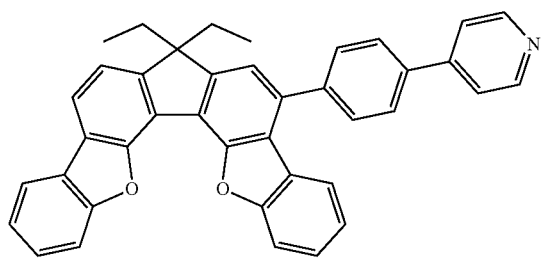
<Chemical Formula 70>
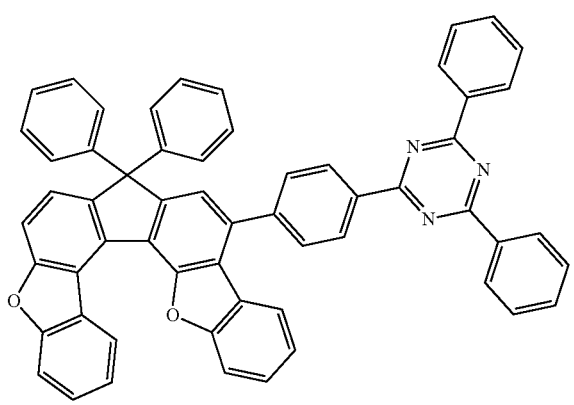
<Chemical Formula 71>
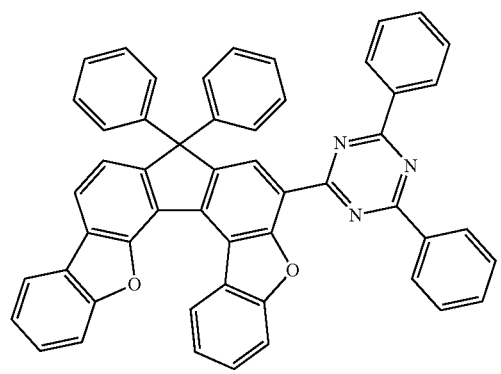
<Chemical Formula 72>
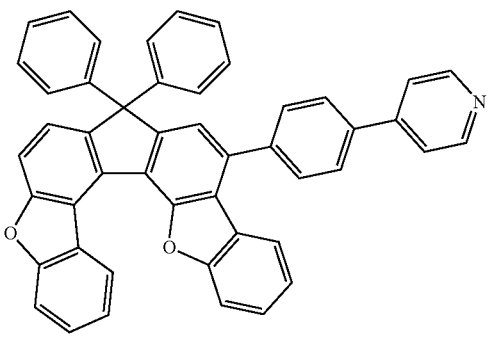
<Chemical Formula 73>
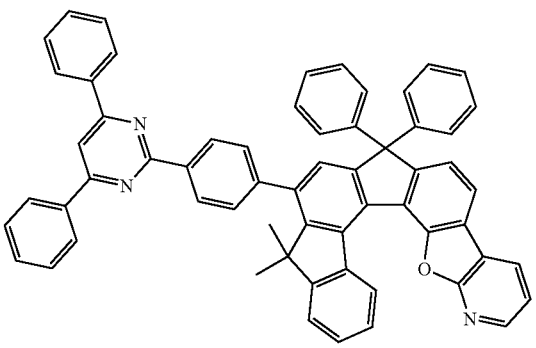
<Chemical Formula 74>
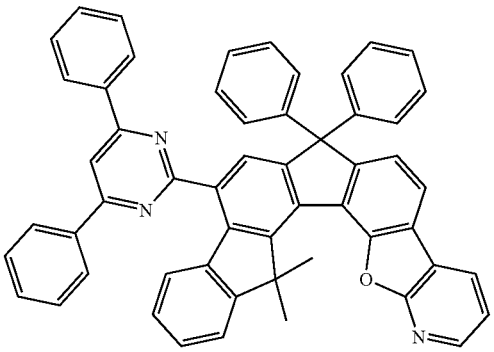
<Chemical Formula 75>
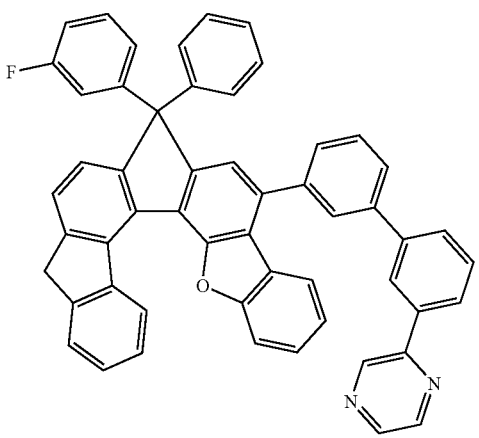

<Chemical Formula 76>
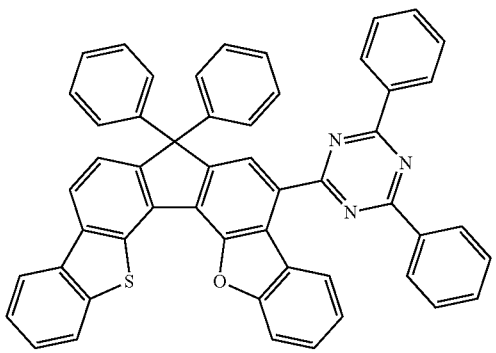
<Chemical Formula 77>
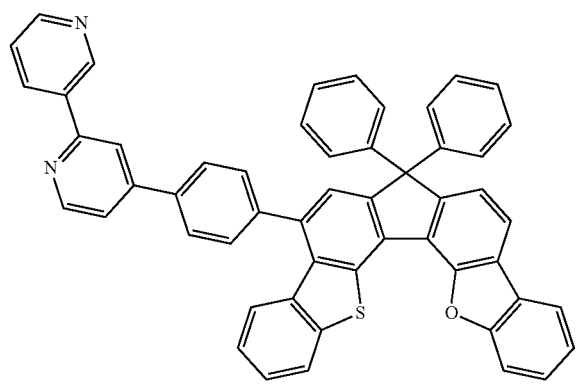
<Chemical Formula 78>
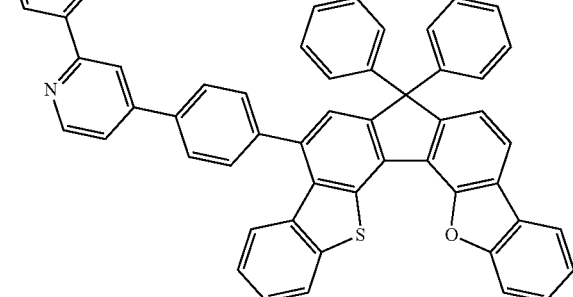
<Chemical Formula 79>
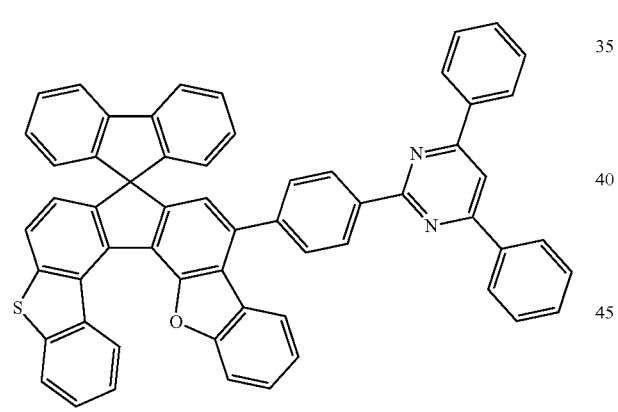
<Chemical Formula 80>
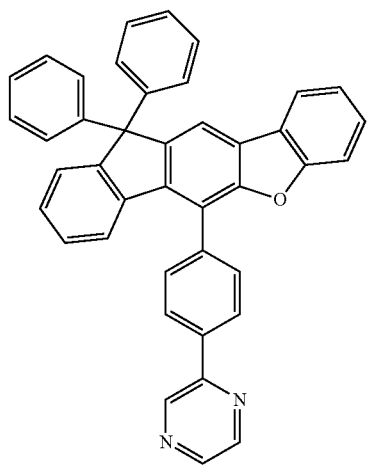
<Chemical Formula 81>
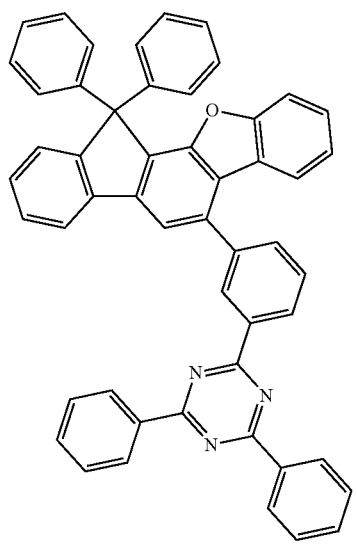
<Chemical Formula 82>
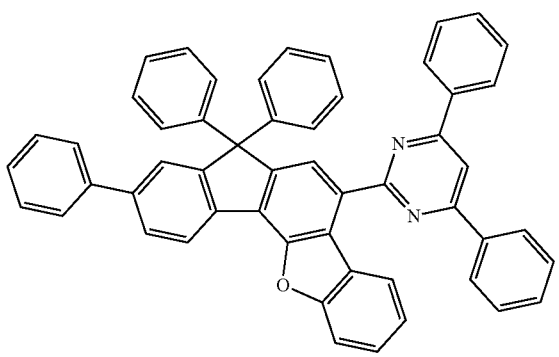

<Chemical Formula 84>
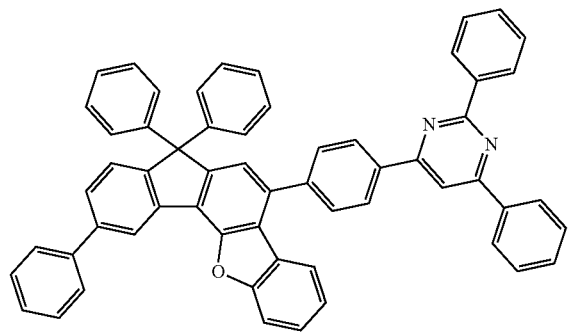
<Chemical Formula 85>
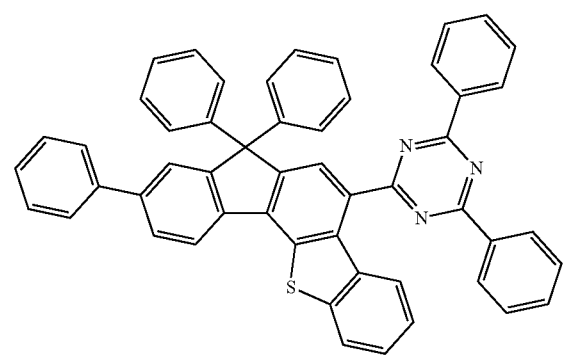
<Chemical Formula 86>
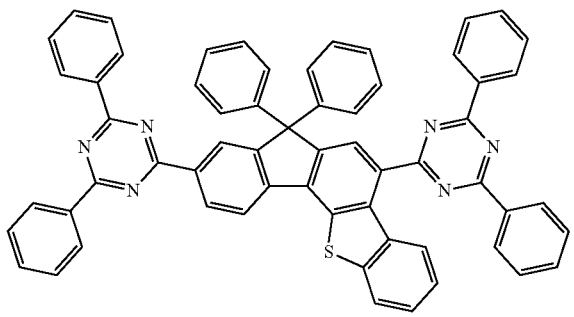
<Chemical Formula 87>
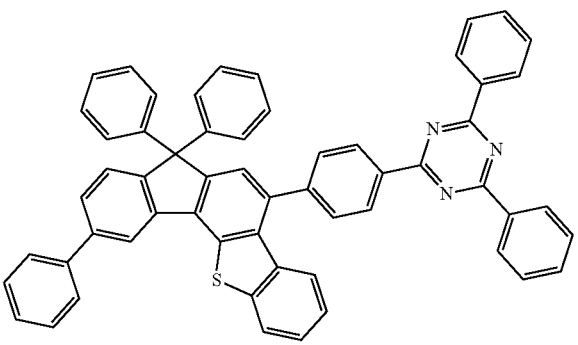
<Chemical Formula 88>
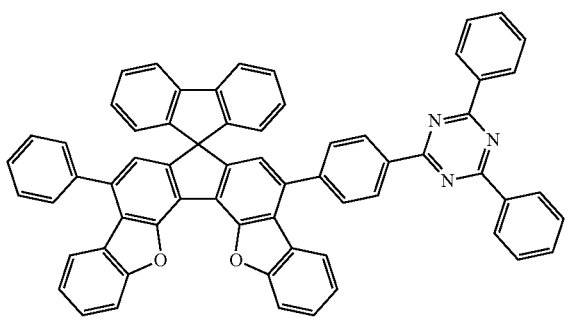
<Chemical Formula 89>
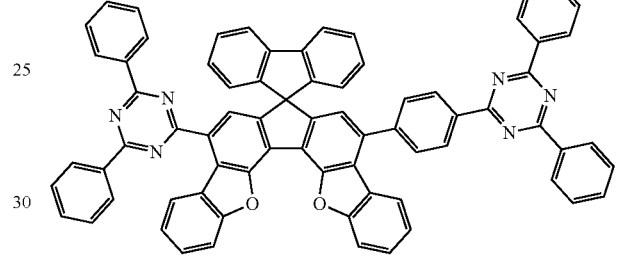
<Chemical Formula 90>
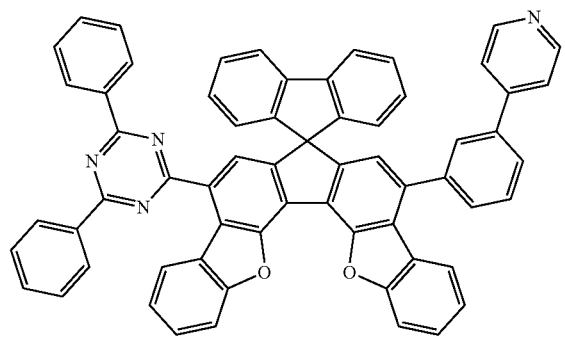
<Chemical Formula 91>
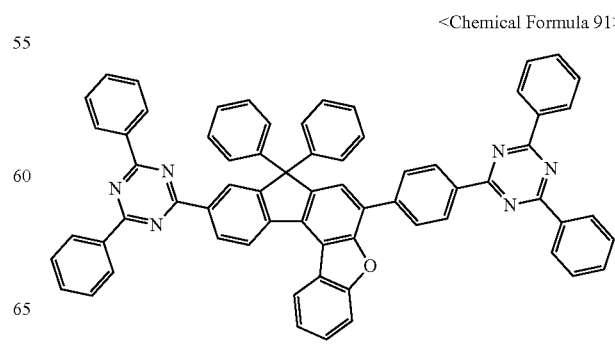

<Chemical Formula 92>
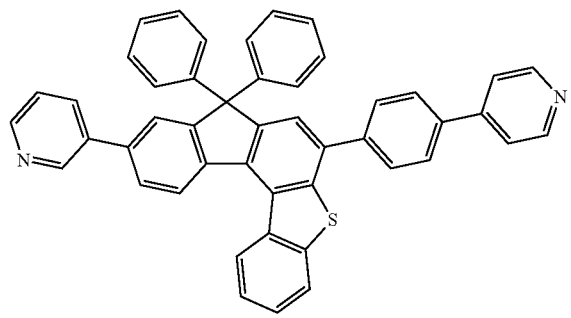
<Chemical Formula 93>
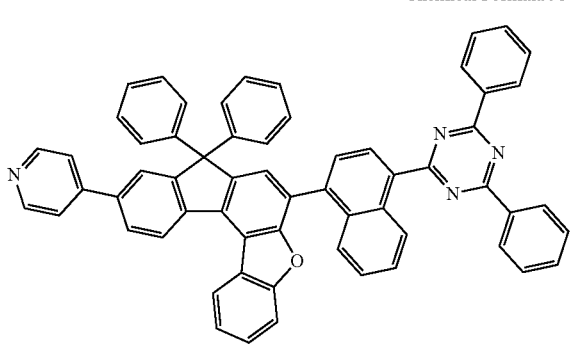
<Chemical Formula 94>
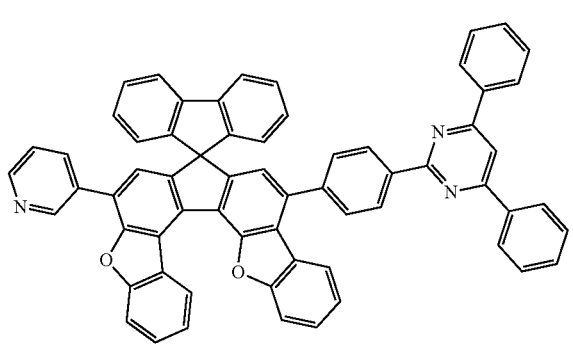
<Chemical Formula 95>
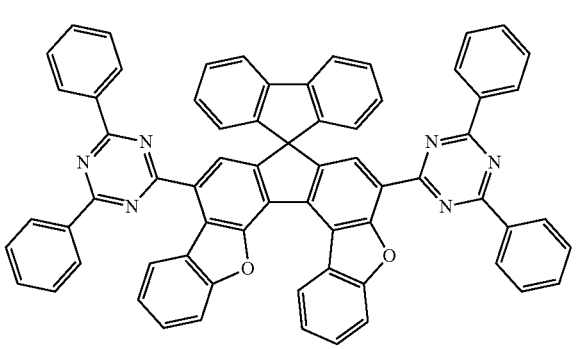
<Chemical Formula 96>
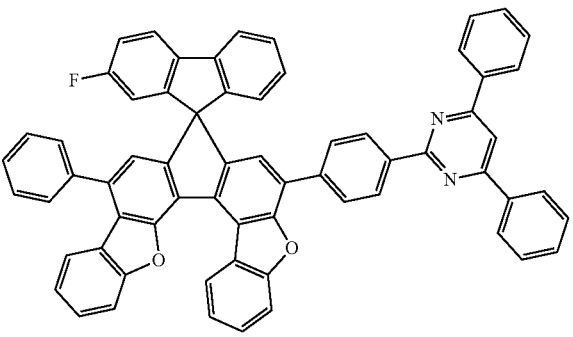
<Chemical Formula 97>
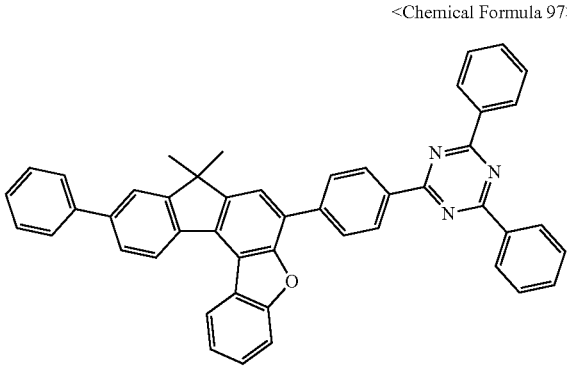
<Chemical Formula 98>
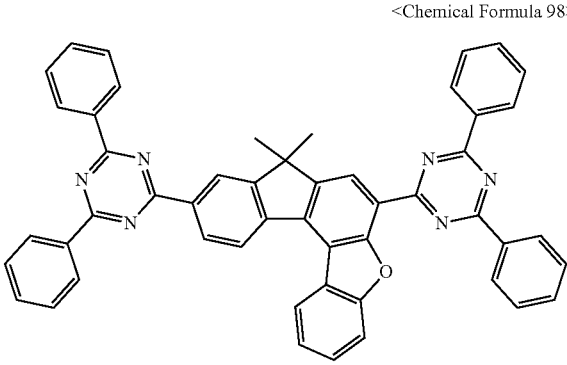
<Chemical Formula 99>
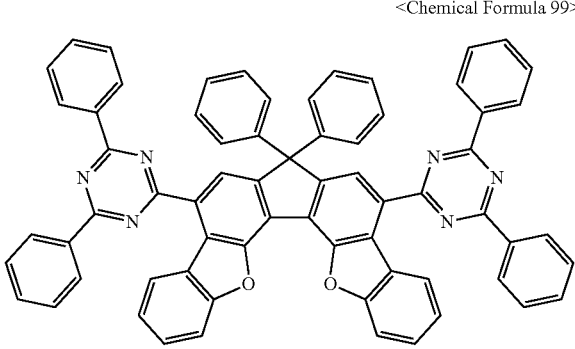

<Chemical Formula 100>

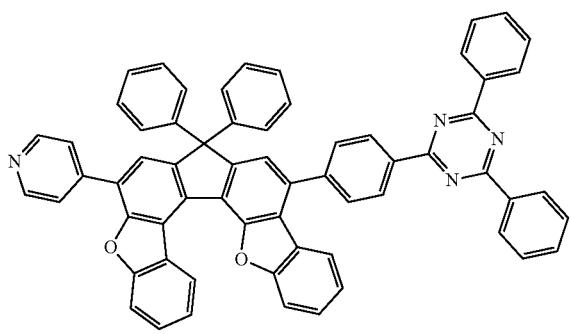

<Chemical Formula 101>

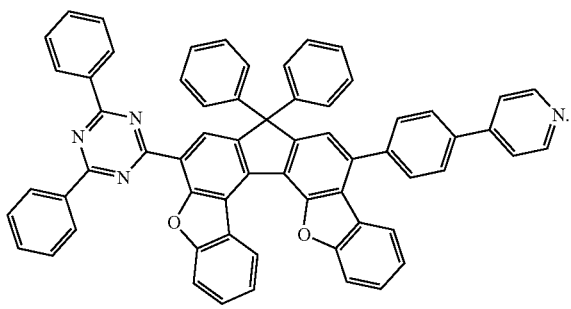

10. An organic light-emitting diode, comprising: a first electrode; a second electrode facing the first electrode; and an organic layer interposed between the first electrode and the second electrode, wherein the organic layer includes at least one of the organic compound of claim 1.

11. The organic light-emitting diode of claim 10, wherein the organic layer comprises at least one of a hole injection layer, a hole transport layer, a functional layer capable of both hole injection and hole transport, a light-emitting layer, an electron transport layer, and an electron injection layer.

12. The organic light-emitting diode of claim 11, wherein the organic layer interposed between the first electrodes and the second electrode includes the electron transport layer and the light-emitting layer wherein the organic compound is used in the electron transport layer and the light-emitting layer is composed of a host and a dopant.

13. The organic light-emitting diode of claim 11, wherein at least one selected from among the hole injection layer, the hole transport layer, the functional layer capable of both hole injection and hole transport, the light-emitting layer, the electron transport layer, and the electron injection layer is deposited using a deposition process or a solution process.

14. The organic light-emitting diode of claim 10, wherein the organic light-emitting diode is used for a device selected from among a flat display device; a flexible display device; a monochrome or grayscale flat illumination device; and a monochrome or grayscale flexible illumination device.

* * * * *